United States Patent
Donnely et al.

(10) Patent No.: US 8,884,023 B2
(45) Date of Patent: Nov. 11, 2014

(54) PYRANO [3,2-D][1,3]THIAZOLE AS GLYCOSIDASE INHIBITORS

(75) Inventors: Marianne Donnely, Reading, MA (US); Hui Qiu, Acton, MA (US); Henry Yu, Wellesley, MA (US); Lesley Liu-Bujalski, Bedford, MA (US); Andreas Goutopoulos, Boston, MA (US)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 14/131,471

(22) PCT Filed: Aug. 22, 2012

(86) PCT No.: PCT/US2012/051785
§ 371 (c)(1),
(2), (4) Date: May 2, 2014

(87) PCT Pub. No.: WO2013/028715
PCT Pub. Date: Feb. 28, 2013

(65) Prior Publication Data
US 2014/0243370 A1    Aug. 28, 2014

Related U.S. Application Data

(60) Provisional application No. 61/527,323, filed on Aug. 25, 2011.

(51) Int. Cl.
C07D 513/04 (2006.01)
A61K 31/429 (2006.01)
A61K 31/454 (2006.01)
A61K 31/4439 (2006.01)

(52) U.S. Cl.
CPC .......... *A61K 31/4439* (2013.01); *A61K 31/454* (2013.01); *A61K 31/429* (2013.01); *C07D 513/04* (2013.01)
USPC .......................................... 548/153; 514/367

(58) Field of Classification Search
USPC ........................................................ 548/153
See application file for complete search history.

(56) References Cited

FOREIGN PATENT DOCUMENTS

| WO | 2008/025170 A1 | 3/2008 |
|---|---|---|
| WO | 2011/140640 A1 | 11/2011 |
| WO | 2012/061927 A1 | 5/2012 |
| WO | 2012/062157 A1 | 5/2012 |
| WO | 2012/083435 A1 | 6/2012 |

OTHER PUBLICATIONS

Golub et al., Science, vol. 286, Oct. 15, 1999, pp. 531-537.*
Yoshida Masaru, et al.; Int. J. Pharm., 115, 61-67 (1995).
Wermuth CG, et al.; The Practice of Medicinal Chemistry Academic Press, Chapter 31: 671-696 (1996).
Bundgaard, H; A Textbook of Drug Design and Development, Harwood Academic Publishers, Chapter 5: 131-191, (1991).
Knapp, Spencer, et al.; Synlett, No. 5 Supp 1, 435-436 (1997).
Biscoe, Mark R., et al. JACS 130: 6686-6687 (2008).
Fors, Brett P., et al. JACS 130: 13552-13554 (2008).

* cited by examiner

*Primary Examiner* — Laura L. Stockton

(57) ABSTRACT

Novel compounds of formula (I)

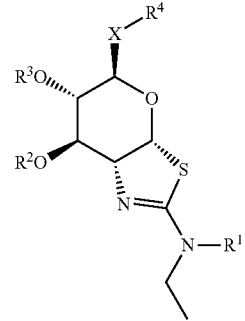

wherein $R^1$ to $R^4$ and X have the meaning according to the claims, are glucosidase inhibitors, and can be employed, inter alia, for the treatment of Alzheimer's disease.

15 Claims, No Drawings

PYRANO [3,2-D][1,3]THIAZOLE AS GLYCOSIDASE INHIBITORS

The present invention relates to compounds of formula (I)

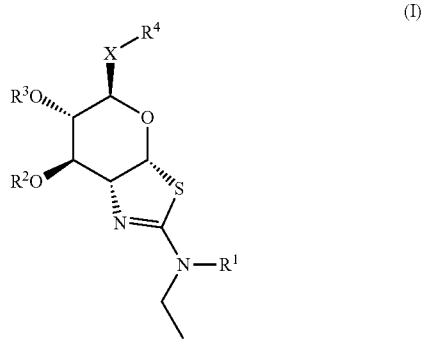

(I)

wherein $R^1$ to $R^4$ and X have the meaning according to the claims, and/or physiologically acceptable salts thereof. The compounds of formula (I) can be used as glycosidase inhibitors. Objects of the invention are also pharmaceutical compositions comprising the compounds of formula (I), and the use of the compounds of formula (I) for the treatment of Alzheimer's disease.

A wide range of cellular proteins, both nuclear and cytoplasmic, are post-translationally modified by the addition of the monosaccharide 2-acetamido-2-deoxy-β-D-glucopyranoside (β-N-acetyl glucosamine) which is attached via an O-glycosidic linkage. This modification is generally referred to as O-linked N-acetylglucosamine or O-GlcNAc. The enzyme responsible for post-translationally linking β-N-acetylglucosamine (GlcNAc) to specific serine and threonine residues of numerous nucleocytoplasmic proteins is O-GlcNAc transferase (OGTase). A second enzyme, known as O-GlcNAcase, removes this post-translational modification to liberate proteins making the O-GlcNAc-modification a dynamic cycle occurring several times during the lifetime of a protein.

O-GlcNAc-modified proteins regulate a wide range of vital cellular functions including, for example, transcription, proteasomal degradation and cellular signaling. O-GlcNAc is also found on many structural proteins. For example, it has been found on a number of cytoskeletal proteins, including neurofilament proteins, synapsins, synapsin-specific clathrin assembly protein AP-3 and Ankyrin-G. O-GlcNAc modification has been found to be abundant in the brain. It has also been found on proteins clearly implicated in the etiology of several diseases including Alzheimer's disease (AD) and cancer.

For example, it is well established that AD and a number of related tauopathies including Downs' syndrome, Pick's disease, Niemann-Pick Type C disease and amyotrophic lateral sclerosis (ALS) are characterized, in part, by the development of neurofibrillary tangles (NFTs). These NFTs are aggregates of paired helical filaments (PHFs) and are composed of an abnormal form of the cytoskeletal protein "tau". Normally, tau stabilizes a key cellular network of microtubules that is essential for distributing proteins and nutrients within neurons. In AD patients, however, tau becomes hyperphosphorylated, disrupting its normal function, forming PHFs and ultimately aggregating to form NFTs. Six isoforms of tau are found in the human brain. In AD patients, all six isoforms of tau are found in NFTs, and all are markedly hyperphosphorylated. Tau in healthy brain tissue bears only 2 or 3 phosphate groups, whereas those found in the brains of AD patients bear, on average, 8 phosphate groups. A clear parallel between NFT levels in the brains of AD patients and the severity of dementia strongly supports a key role for tau dysfunction in AD. The precise causes of this hyperphosphorylation of tau remain elusive. Accordingly, considerable effort has been dedicated toward: a) elucidating the molecular physiological basis of tau hyperphosphorylation; and b) identifying strategies that could limit tau hyperphosphorylation in the hope that these might halt, or even reverse, the progression of Alzheimer's disease. Several lines of evidence suggest that up-regulation of a number of kinases may be involved in hyperphosphorylation of tau, although very recently, an alternative basis for this hyperphosphorylation has been advanced.

In particular, it has recently emerged that phosphate levels of tau are regulated by the levels of O-GlcNAc on tau. The presence of O-GlcNAc on tau has stimulated studies that correlate O-GlcNAc levels with tau phosphorylation levels. The recent interest in this field stems from the observation that O-GlcNAc modification has been found to occur on many proteins at amino acid residues that are also known to be phosphorylated. Consistent with this observation, it has been found that increases in phosphorylation levels result in decreased O-GlcNAc levels and conversely, increased O-GlcNAc levels correlate with decreased phosphorylation levels. This reciprocal relationship between O-GlcNAc and phosphorylation has been termed the "Yin-Yang hypothesis" and has gained strong biochemical support by the recent discovery that the enzyme OGTase forms a functional complex with phosphatases that act to remove phosphate groups from proteins. Like phosphorylation, O-GlcNAc is a dynamic modification that can be removed and reinstalled several times during the lifespan of a protein. Suggestively, the gene encoding O-GlcNAcase has been mapped to a chromosomal locus that is linked to AD. Hyperphosphorylated tau in human AD brains has markedly lower levels of O-GlcNAc than are found in healthy human brains. Very recently, it has been shown that O-GlcNAc levels of soluble tau protein from human brains affected with AD are markedly lower than those from healthy brain. Furthermore, PHF from diseased brain was suggested to lack completely any O-GlcNAc modification whatsoever. The molecular basis of this hypoglycosylation of tau is not known, although it may stem from increased activity of kinases and/or dysfunction of one of the enzymes involved in processing O-GlcNAc. Supporting this latter view, in both PC-12 neuronal cells and in brain tissue sections from mice, a nonselective N-acetylglucosaminidase inhibitor was used to increase tau O-GlcNAc levels, whereupon it was observed that phosphorylation levels decreased. The implication of these collective results is that by maintaining healthy O-GlcNAc levels in AD patients, such as by inhibiting the action of O-GlcNAcase (OGA), one should be able to block hyperphosphorylation of tau and all of the associated effects of tau hyperphosphorylation, including the formation of NFTs and downstream effects. However, because the proper functioning of the lysosomal β-hexosaminidases is critical, any potential therapeutic intervention for the treatment of AD that blocks the action of O-GlcNAcase would have to avoid the concomitant inhibition of both lysosomal hexosaminidases A and B.

Consistent with the known properties of the hexosamine biosynthetic pathway, the enzymatic properties of O-GlcNAc transferase (OGTase), and the reciprocal relationship between O-GlcNAc and phosphorylation, it has been shown that decreased glucose availability in brain leads to tau hyperphosphorylation. The gradual impairment of glucose transport and metabolism leads to decreased O-GlcNAc and hyperphosphorylation of tau (and other proteins). Accordingly, the inhibition of O-GlcNAcase should compensate for the age-related impairment of glucose metabolism within the brains of health individuals as well as patients suffering from AD or related neurodegenerative diseases.

These results suggest that a malfunction in the mechanisms regulating tau O-GlcNAc levels may be vitally important in the formation of NFTs and associated neurodegeneration. Good support for blocking tau hyperphosphorylation as a therapeutically useful intervention comes from recent studies showing that when transgenic mice harboring human tau are treated with kinase inhibitors, they do not develop typical motor defects and, in another case, show decreased levels of insoluble tau. These studies provide a clear link between lowering tau phosphorylation levels and alleviating AD-like behavioral symptoms in a murine model of this disease.

There is also a large body of evidence indicating that increased levels of O-GlcNAc protein modification provides protection against pathogenic effects of stress in cardiac tissue, including stress caused by ischemia, hemorrhage, hypervolemic shock, and calcium paradox. For example, activation of the hexosamine biosynthetic pathway (HBP) by administration of glucosamine has been demonstrated to exert a protective effect in animal models of ischemia/reperfusion, trauma hemorrhage, hypervolemic shock and calcium paradox. Moreover, strong evidence indicates that these cardioprotective effects are mediated by elevated levels of protein O-GlcNAc modification. There is also evidence that the O-GlcNAc modification plays a role in a variety of neurodegenerative diseases, including Parkinson's disease and Huntington's disease.

Humans have three genes encoding enzymes that cleave terminal β-N-acetyl-glucosamine residues from glycoconjugates. The first of these encodes the enzyme O-glycoprotein-2-acetamido-2-deoxy-β-D-glucopyranosidase (O-GlcNAcase). O-GlcNAcase is a member of family 84 of glycoside hydrolases. O-GlcNAcase acts to hydrolyze O-GlcNAc off of serine and threonine residues of post-translationally modified proteins. Consistent with the presence of O-GlcNAc on many intracellular proteins, the enzyme O-GlcNAcase appears to have a role in the etiology of several diseases including type II diabetes, AD and cancer. Although O-GlcNAcase was likely isolated earlier on, about 20 years elapsed before its biochemical role in acting to cleave O-GlcNAc from serine and threonine residues of proteins was understood. More recently O-GlcNAcase has been cloned, partially characterized, and suggested to have additional activity as a histone acetyltransferase.

However, a major challenge in developing inhibitors for blocking the function of mammalian glycosidases, including O-GlcNAcase, is the large number of functionally related enzymes present in tissues of higher eukaryotes. Accordingly, the use of non-selective inhibitors in studying the cellular and organismal physiological role of one particular enzyme is complicated because complex phenotypes arise from the concomitant inhibition of such functionally related enzymes. In the case of 3-N-acetylglucosaminidases, existing compounds that act to block O-GlcNAcase function are non-specific and act potently to inhibit the lysosomal β-hexosaminidases.

Low molecular weight OGA inhibitors are disclosed in the international application WO 2008/025170, WO 2011/140640, WO 2012/061927, WO 2012/062157, WO 2012/083435, which are hereby incorporated by reference. There is still a need for low molecular weight molecules that selectively inhibit OGA.

The invention had the object of finding novel compounds having valuable properties, in particular those which can be used for the preparation of medicaments.

It has been surprisingly found that the compounds according to the invention and salts thereof have very valuable pharmacological properties. In particular, they act as glycosidase inhibitors. The invention relates to compounds of formula (I)

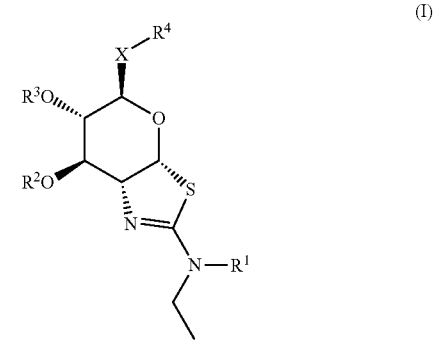

wherein
$R^1$ denotes Y, COA, COOA, COO—$(CH_2)_n$—Ar, COO—$(CH_2)_n$-Cyc;
$R^2$, $R^3$ denote independently from one another Y or $SO_2Y$;
$R^4$ denotes Hal, Y, OY, OCOOY, COOY, CONYY, NHCOY, $SO_2Y$, CN, NYY, NYOY, N=$N^+$=$N^-$, $CAr_3$, $(CH_2)_n$—Ar, O—$(CH_2)_n$—Ar, NY—$(CH_2)_n$—Ar, NY—$(CH_2)_n$-Cyc, NY—$(CH_2)_n$-Het,

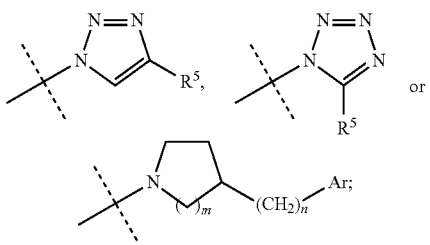

$R^5$ denotes $(CH_2)_n$—Ar, $(CH_2)_n$-Cyc, $(CH_2)_n$-Het, $(CH_2)_n$—O—Ar, $(CH_2)_n$—CY(OH)—Ar, $(CH_2)_n$—CO—Ar or $(CH_2)_n$—NY—Ar;
X denotes $CH_2$, CO or CH(OH);
Y denotes H or A;
A denotes unbranched or branched alkyl having 1-10 C atoms, in which 1-7H atoms can be replaced independently from one another by Hal and/or in which one $CH_2$ group can be replaced by a —CH=CH— group;
Cyc denotes cycloalkyl having 3-7 C atoms, in which 1-4H atoms can be replaced independently from one another by Hal and/or which can be substituted by Ar;
Ar denotes an unsaturated or aromatic mono- or bicyclic carbocycle having 3-12 C atoms,
which can be substituted by at least one substituent selected from the group of Hal, A, $(CY_2)_n$—OY, $(CY_2)_n$—NYY, COOY, CONYY, NHCOY, $SO_2Y$, CN and phenoxy;
Het denotes an unsaturated or aromatic mono-, bi- or tricyclic heterocycle having 1-12 C atoms and 1-4 N atoms,
which can be substituted by at least one substituent selected from the group of Hal, A, $(CY_2)_n$—OY, $(CY_2)_n$—NYY, COOY, CONYY, NHCOY, $SO_2Y$, $SO_2Ar$, CN and thiophenyl;

Hal denotes F, Cl, Br or I;
m denotes 1, 2 or 3; and
n denotes 0, 1, 2, 3, 4, 5 or 6;
and/or physiologically acceptable salts thereof.

In particular, the invention relates to a compound of formula (I)

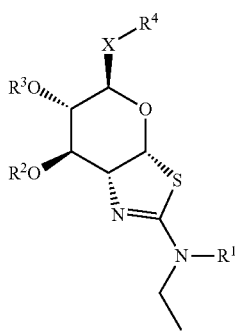

(I)

wherein
R$^1$ denotes Y, COA, COOA, COO—(CH$_2$)$_n$—Ar, COO—(CH$_2$)$_n$-Cyc; PP
R$^2$, R$^3$ denote independently from one another Y or SO$_2$Y;
R$^4$ denotes Cl, Br, I, COOY, SO$_2$Y, CN, CAr$_3$, (CH$_2$)$_m$—Ar,

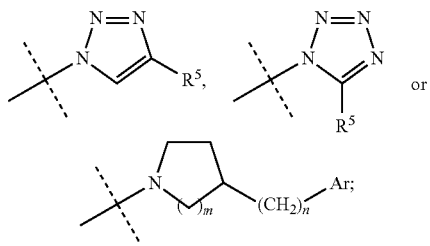

R$^5$ denotes (CH$_2$)$_n$—Ar, (CH$_2$)$_n$-Cyc, (CH$_2$)$_n$-Het, (CH$_2$)$_n$—O—Ar, (CH$_2$)$_n$—CY(OH)—Ar, (CH$_2$)$_n$—CO—Ar or (CH$_2$)$_n$—NY—Ar;
X denotes CH$_2$, CO or CH(OH);
Y denotes H or A;
A denotes unbranched or branched alkyl having 1-10 C atoms,
  in which 1-7H atoms can be replaced independently from one another by Hal and/or in which one CH$_2$ group can be replaced by a —CH═CH— group;
Cyc denotes cycloalkyl having 3-7 C atoms,
  in which 1-4H atoms can be replaced independently from one another by Hal and/or which can be substituted by Ar;
Ar denotes an unsaturated or aromatic mono- or bicyclic carbocycle having 3-12 C atoms,
  which can be substituted by at least one substituent selected from the group of Hal, A, (CY$_2$)$_n$—OY, (CY$_2$)$_n$—NYY, COOY, CONYY, NHCOY, SO$_2$Y, CN and phenoxy;
Het denotes an unsaturated or aromatic mono-, bi- or tricyclic heterocycle having 1-12 C atoms and 1-4 N atoms,
  which can be substituted by at least one substituent selected from the group of Hal, A, (CY$_2$)$_n$—OY, (CY$_2$)$_n$—NYY, COOY, CONYY, NHCOY, SO$_2$Y, SO$_2$Ar, CN and thiophenyl;

Hal denotes F, Cl, Br or I;
m denotes 1, 2 or 3; and
n denotes 0, 1, 2, 3, 4, 5 or 6;
and/or a physiologically acceptable salt thereof.

In the meaning of the present invention, the compound is defined to include pharmaceutically usable derivatives, solvates, prodrugs, tautomers, enantiomers, racemates and stereoisomers thereof, including mixtures thereof in all ratios.

The term "pharmaceutically usable derivatives" is taken to mean, for example, the salts of the compounds according to the invention and also so-called prodrug compounds. The term "solvates" of the compounds is taken to mean adductions of inert solvent molecules onto the compounds, which are formed owing to their mutual attractive force. Solvates are, for example, mono- or dihydrates or alkoxides. The invention also comprises solvates of salts of the compounds according to the invention. The term "prodrug" is taken to mean compounds according to the invention which have been modified by means of, for example, alkyl or acyl groups, sugars or oligopeptides and which are rapidly cleaved in the organism to form the effective compounds according to the invention. These also include biodegradable polymer derivatives of the compounds according to the invention, as described, for example, in Int. J. Pharm. 115, 61-67 (1995). It is likewise possible for the compounds of the invention to be in the form of any desired prodrugs such as, for example, esters, carbonates, carbamates, ureas, amides or phosphates, in which cases the actually biologically active form is released only through metabolism. Any compound that can be converted in-vivo to provide the bioactive agent (i.e. compounds of the invention) is a prodrug within the scope and spirit of the invention. Various forms of prodrugs are well known in the art and are described (e.g. Wermuth C G et al., Chapter 31: 671-696, The Practice of Medicinal Chemistry, Academic Press 1996; Bundgaard H, Design of Prodrugs, Elsevier 1985; Bundgaard H, Chapter 5: 131-191, A Textbook of Drug Design and Development, Harwood Academic Publishers 1991). Said references are incorporated herein by reference. It is further known that chemical substances are converted in the body into metabolites which may where appropriate likewise elicit the desired biological effect—in some circumstances even in more pronounced form. Any biologically active compound that was converted in-vivo by metabolism from any of the compounds of the invention is a metabolite within the scope and spirit of the invention.

The compounds of the invention may be present in the form of their double bond isomers as pure E or Z isomers, or in the form of mixtures of these double bond isomers. Where possible, the compounds of the invention may be in the form of the tautomers, such as keto-enol tautomers. All stereoisomers of the compounds of the invention are contemplated, either in a mixture or in pure or substantially pure form. The compounds of the invention can have asymmetric centers at any of the carbon atoms. Consequently, they can exist in the form of their racemates, in the form of the pure enantiomers and/or diastereomers or in the form of mixtures of these enantiomers and/or diastereomers. The mixtures may have any desired mixing ratio of the stereoisomers. Thus, for example, the compounds of the invention which have one or more centers of chirality and which occur as racemates or as diastereomer mixtures can be fractionated by methods known per se into their optical pure isomers, i.e. enantiomers or diastereomers. The separation of the compounds of the invention can take place by column separation on chiral or non-chiral phases or by re-crystallization from an optionally optically active solvent or with use of an optically active acid or base or by derivatization with an optically active reagent such as, for example, an optically active alcohol, and subsequent elimination of the radical.

The invention also relates to the use of mixtures of the compounds according to the invention, for example mixtures of two diastereomers, for example in the ratio 1:1, 1:2, 1:3, 1:4, 1:5, 1:10, 1:100 or 1:1000. These are particularly preferably mixtures of stereoisomeric compounds.

The nomenclature as used herein for defining compounds, especially the compounds according to the invention, is in general based on the rules of the IUPAC-organization for chemical compounds and especially organic compounds. The terms indicated for explanation of the above compounds of the invention always, unless indicated otherwise in the description or in the claims, have the following meanings:

The term "unsubstituted" means that the corresponding radical, group or moiety has no substituents. The term "substituted" means that the corresponding radical, group or moiety has one or more substituents. Where a radical has a plurality of substituents, and a selection of various substituents is specified, the substituents are selected independently of one another and do not need to be identical. Even though a radical has a plurality of a specific-designated substituent (e.g. $Ar_3$ or YY) the expression of such substituent may differ from each other (e.g. methyl and ethyl). It shall be understood accordingly that a multiple substitution by any radical of the invention may involve identical or different radicals. Hence, if individual radicals occur several times within a compound, the radicals adopt the meanings indicated, independently of one another. In case of a multiple substitution, the radical could be alternatively designated with R', R", R''' etc.

The terms "alkyl" or "A" refer to acyclic saturated or unsaturated hydrocarbon radicals, which may be branched or straight-chain and preferably have 1, 2, 3, 4, 5, 6, 7, 8, 9 or 10 carbon atoms, i.e. $C_1$-$C_{10}$-alkanyls. Examples of suitable alkyl radicals are methyl, ethyl, n-propyl, isopropyl, 1,1-, 1,2- or 2,2-dimethylpropyl, 1-ethylpropyl, 1-ethyl-1-methylpropyl, 1-ethyl-2-methylpropyl, 1,1,2- or 1,2,2-trimethylpropyl, n-butyl, isobutyl, sec-butyl, tert-butyl, 1-, 2- or 3-methylbutyl, 1,1-, 1,2-, 1,3-, 2,2-, 2,3- or 3,3-dimethylbutyl, 1- or 2-ethylbutyl, n-pentyl, iso-pentyl, neo-pentyl, tert-pentyl, 1-, 2-, 3- or -methyl-pentyl, n-hexyl, 2-hexyl, isohexyl, n-heptyl, n-octyl, n-nonyl, n-decyl, n-undecyl, n-dodecyl, n-tetradecyl, n-hexadecyl, n-octadecyl, n-icosanyl, n-docosanyl.

In a preferred embodiment of the invention, A denotes unbranched or branched alkyl having 1-10 C atoms, in which 1-7H atoms may be replaced independently from one another by Hal and/or in which one $CH_2$ group can be replaced by a —CH═CH— group. A more preferred embodiment of A denotes unbranched or branched alkyl having 1-6 C atoms, in which 1-4 atoms may be replaced independently from one another by Hal. In a most preferred embodiment of the invention, A denotes unbranched or branched alkyl having 1-4 C atoms, in which 1-3H atoms can be replaced independently from one another by Hal. It is highly preferred that A denotes unbranched or branched alkyl having 1-4 C atoms, in which 1-3H atoms can be replaced independently from one another by F and/or Cl. Particularly preferred are $C_{1-4}$-alkyl. A $C_{1-4}$-alkyl radical is for example a methyl, ethyl, propyl, isopropyl, butyl, isobutyl, tert-butyl, sec-butyl, tert-butyl, fluoromethyl, difluoromethyl, trifluoromethyl, pentafluoroethyl, 1,1,1-trifluoroethyl or bromomethyl, especially methyl, ethyl, propyl or trifluoromethyl. It shall be understood that the respective denotation of A is independently of one another in any radical of the invention.

The terms "cycloalkyl" or "Cyc" for the purposes of this invention refers to saturated and partially unsaturated non-aromatic cyclic hydrocarbon groups/radicals, having 1 to 3 rings, that contain 3 to 20, preferably 3 to 12, more preferably 3 to 9 carbon atoms. The cycloalkyl radical may also be part of a bi- or polycyclic system, where, for example, the cycloalkyl radical is fused to an aryl, heteroaryl or heterocyclyl radical as defined herein by any possible and desired ring member(s). The bonding to the compounds of the general formula (I) can be effected via any possible ring member of the cycloalkyl radical. Examples of suitable cycloalkyl radicals are cyclopropyl, cyclobutyl, cyclopentyl, cyclohexyl, cycloheptyl, cyclooctyl, cyclodecyl, cyclohexenyl, cyclopentenyl and cyclooctadienyl.

In a preferred embodiment of the invention, Cyc denotes cycloalkyl having 3-7 C atoms, in which 1-4H atoms may be replaced independently of one another by Hal and/or which can be substituted by Ar. More preferred is $C_3$-$C_6$-cycloalkyl, which can be monosubstituted by Ar. Most preferred is $C_3$-$C_6$-cycloalkyl, i.e. cyclopropyl, cyclobutyl, cyclopentyl or cyclohexyl. Moreover, the definition of A shall also comprise cycloalkyls and it is to be applied mutatis mutandis to Cyc. It shall be understood that the respective denotation of Cyc is independently of one another in any radical of the invention.

The term "aryl" or "carboaryl" for the purposes of this invention refers to a mono- or polycyclic aromatic hydrocarbon systems having 3 to 14, preferably 5 to 10, more preferably 6 to 8 carbon atoms, which can be optionally substituted. The term "aryl" also includes systems in which the aromatic cycle is part of a bi- or polycyclic saturated, partially unsaturated and/or aromatic system, such as where the aromatic cycle is fused to an aryl, cycloalkyl, heteroaryl or heterocyclyl group as defined herein via any desired and possible ring member of the aryl radical. The bonding to the compounds of the general formula (I) can be effected via any possible ring member of the aryl radical. Examples of suitable aryl radicals are phenyl, biphenyl, naphthyl, 1-naphthyl, 2-naphthyl and anthracenyl, but likewise in-danyl, indenyl or 1,2,3,4-tetrahydronaphthyl. Preferred carboaryls of the invention are optionally substituted phenyl, naphthyl and biphenyl, more preferably optionally substituted monocylic carboaryl having 6-8 C atoms, most preferably optionally substituted phenyl.

In another embodiment of the invention, a carbocycle, including, but not limited to, carboaryl, is defined as "Ar". Examples of suitable Ar radicals are phenyl, o-, m- or p-tolyl, o-, m- or p-ethylphenyl, o-, m- or p-propylphenyl, o-, m- or p-isopropylphenyl, o-, m- or p-tert.-butylphenyl, o-, m- or p-hydroxyphenyl, o-, m- or p-methoxyphenyl, o-, m- or p-ethoxyphenyl, o-, m- or p-fluorophenyl, o-, m- or p-bromophenyl, o-, m- or p-chlorophenyl, o-, m- or p-sulfonamidophenyl, o-, m- or p-(N-methyl-sulfonamido)phenyl, o-, m- or p-(N,N-dimethyl-sulfonamido)phenyl, o-, m- or p-(N-ethyl-N-methyl-sulfonamido)phenyl, o-, m- or p-(N,N-diethyl-sulfonamido)-phenyl, particularly 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl or 2,5-dimethyl-4-chlorophenyl.

Ar preferably denotes an unsaturated or aromatic mono- or bicyclic carbocycle having 3-12 C atoms, which can be substituted by at least one substituent selected from the group of Hal, A, $(CY_2)_n$—OY, $(CY_2)_n$—NYY, COOY, CONYY, NHCOY, $SO_2Y$, CN and phenoxy. In a more preferred embodiment of the invention, Ar denotes an aromatic monoor bicyclic carbocycle having 3-12 C atoms, which can be substituted by at least one substituent selected from the group of Hal, A, $(CY_2)_n$—OY, $(CY_2)_n$—NYY, $SO_2Y$, CN and phenoxy. In a most preferred embodiment of the invention, Ar denotes an aromatic monocyclic carbocycle having 4-10 C atoms, which can be substituted by at least one substituent selected from the group of Hal, A, $(CY_2)_n$—OY, $(CY_2)_n$—NYY, $SO_2Y$, CN and phenoxy. It is highly preferred that Ar denotes an aromatic monocyclic carbocycle having 6-8 C atoms, which can be monosubstituted by Hal, A, OA, $(CY_2)_n$—OH, $SO_2A$ or CN. In a particularly highly preferred embodiment of the invention, Ar denotes phenyl. It shall be understood that the respective denotation of Ar is independently of one another in any radical of the invention.

The term "heterocycle" or "heterocyclyl" for the purposes of this invention refers to a mono- or polycyclic system of 1-15 ring atoms, preferably 1-12 ring atoms, more preferably 3-9 ring atoms, comprising carbon atoms and 1, 2, 3, 4 or 5 heteroatoms, which are identical or different, in particular nitrogen, oxygen and/or sulfur. The cyclic system may be saturated or mono- or poly-unsaturated, preferably unsaturated. In the case of a cyclic system consisting of at least two rings the rings may be fused or spiro or otherwise connected. Such heterocyclyl radicals can be linked via any ring member. The term "heterocyclyl" also includes systems in which the heterocycle is part of a bi- or polycyclic saturated, partially unsaturated and/or aromatic system, such as where the heterocycle is fused to an aryl, cycloalkyl, heteroaryl or heterocyclyl group as defined herein via any desired and possible ring member of the heterocyclyl radical. The bonding to the compounds of the general formula (I) can be effected via any possible ring member of the heterocyclyl radical. Examples of suitable heterocyclyl radicals are pyrrolidinyl, thiapyrrolidinyl, piperidinyl, piperazinyl, oxapiperazinyl, oxapiperidinyl, oxadiazolyl, tetrahydrofuryl, imidazolidinyl, thiazolidinyl, tetrahydropyranyl, morpholinyl, tetrahydrothiophenyl, dihydropyranyl.

The terms "heteroaryl" for the purposes of this invention refers to a 1-15, preferably 1-12, more preferably 3-9, most preferably 5-, 6- or 7-membered mono- or polycyclic aromatic hydrocarbon radical which comprises at least 1, where appropriate also 2, 3, 4 or 5 heteroatoms, preferably nitrogen, oxygen and/or sulfur, where the heteroatoms are identical or different. Preferably, the number of nitrogen atoms is 0, 1, 2, 3 or 4, and that of the oxygen and sulfur atoms is independently from one another 0 or 1. The term "heteroaryl" also includes systems in which the aromatic cycle is part of a bi- or polycyclic saturated, partially unsaturated and/or aromatic system, such as where the aromatic cycle is fused to an aryl, cycloalkyl, heteroaryl or heterocyclyl group as defined herein via any desired and possible ring member of the heteroaryl radical. The bonding to the compounds of the general formula (I) can be effected via any possible ring member of the heteroaryl radical. Examples of suitable heteroaryl are pyrrolyl, thienyl, furyl, imidazolyl, thiazyl, isothiazyl, oxazyl, oxadiazyl, isoxazyl, pyrazyl, pyridyl, pyrimidyl, pyridazinyl, pyrazyl, indolyl, quinolyl, isoquinolinyl, imidazolyl, triazolyl, triazinyl, tetrazyl, phthalazinyl, indazolyl, indolizinyl, quinoxalinyl, quinazolinyl, pteridinyl, carbazolyl, phenazinyl, phenoxazinyl, phenothiazinyl and acridinyl.

It is preferred that heterocycle or heteroaryl in the realms of "Het" represents an unsaturated or aromatic mono-, bi- or tricyclic heterocycle having 1-12 C atoms and 1-4 N atoms, which can be substituted by at least one substituent selected from the group of Hal, A, $(CY_2)_n$—OY, $(CY_2)_n$—NYY, COOY, CONYY, NHCOY, $SO_2Y$, $SO_2Ar$, CN and thiophenyl. Suitable examples are pyrrolyl, imidazolyl, benzoimidazolyl, pyrazyl, triazolyl, benzotriazolyl, pyridyl and carbazolyl, which can be optionally substituted. In a more preferred embodiment of the invention, Het denotes an unsaturated or aromatic mono-, bi- or tricyclic heterocycle having 2-12 C atoms and 1-3 N atoms, which can be mono-, di- or trisubstituted by at least one substituent selected from the group of Hal, A, $(CH_2)_n$—OY, $(CY_2)_n$—NYY, $SO_2Y$, $SO_2Ar$, CN and thiophenyl. It is most preferred that Het denotes an unsaturated or aromatic mono- or bicyclic heterocycle having 3-9 C atoms and 1-3 N atoms, which can be mono-, di- or trisubstituted by at least one substituent selected from the group of A, $SO_2Ar$ and thiophenyl. Highly preferred Het is an unsaturated or aromatic mono- or bicyclic heterocycle having 5-7 C atoms and 1-3 N atoms. Benzotriazolyl is particularly preferred. It shall be understood that the respective denotation of Het is independently of one another in any radical of the invention.

The term "halogen", "halogen atom", "halogen substituent" or "Hal" for the purposes of this invention refers to one or, where appropriate, a plurality of fluorine (F, fluoro), bromine (Br, bromo), chlorine (Cl, chloro) or iodine (I, iodo) atoms. The designations "dihalogen", "trihalogen" and "perhalogen" refer respectively to two, three and four substituents, where each substituent can be selected independently from the group consisting of fluorine, chlorine, bromine and iodine. Halogen preferably means a fluorine, chlorine or bromine atom. Fluorine and chlorine are more preferred, particularly when the halogens are substituted on an alkyl (haloalkyl) or alkoxy group (e.g. $CF_3$ and $CF_3O$). It is another preferred aspect that halogen denotes Cl, Br or I. It shall be understood that the respective denotation of Hal is independently of one another in any radical of the invention.

It is a preferred embodiment of the present invention that $R^1$, $R^2$, $R^3$ denote independently from one another H or A, more preferably H.

It is another preferred embodiment of the present invention that $R^4$ denotes Hal, H, OY, OCOOA, COOA, NYY, NAOA, $N=N^+=N^-$, $CAr_3$, $(CH_2)_n$—Ar, O—$(CH_2)_n$—Ar, NY—$(CH_2)_n$—Ar, NH—$(CH_2)_n$-Cyc, NH—$(CH_2)_n$-Het,

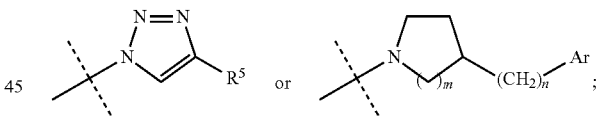

more preferably Hal, H, COOA, NYY, NAOA, $(CH_2)_n$—Ar, NH—$(CH_2)_n$-Cyc, NH—$(CH_2)_n$-Het,

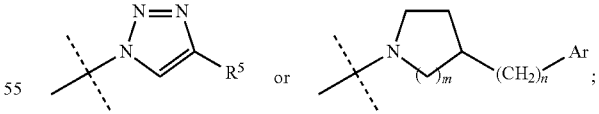

and
most preferably Hal, NYY, $(CH_2)_n$—Ar or

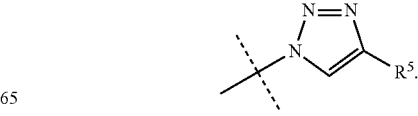

It is another more preferred aspect of the invention that $R^4$ denotes Hal, H, COOY, $SO_2Y$, CN, $CAr_3$, $(CH_2)_m$—Ar,

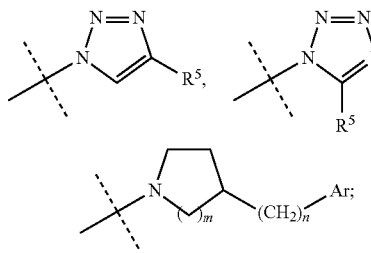

most preferably Hal, H, COOY, $CAr_3$ or

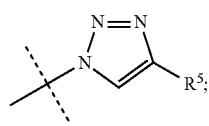

highly preferably Hal or

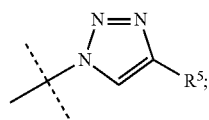

and particularly highly preferably

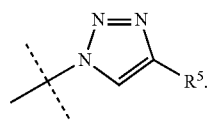

It is another preferred embodiment of the present invention that $R^5$ denotes $(CH_2)_n$—Ar, $(CH_2)_n$-Cyc, $(CH_2)_n$-Het, $(CH_2)_n$—O—Ar, $(CH_2)_n$—CY(OH)—Ar or $(CH_2)_n$—NA-Ar; more preferably $(CH_2)_n$—Ar, $(CH_2)_n$-Cyc, $(CH_2)_n$-Het, $(CH_2)_n$—O—Ar or CY(OH)—Ar; and most preferably $(CH_2)_n$-Het, $(CH_2)_n$—O—Ar or CY(OH)—Ar.

It is another preferred embodiment of the present invention that X denotes $CH_2$, CO or CH(OH) with the proviso that $CH_2$ and/or CH(OH) are excluded if $R^4$ denotes H.

In an aspect of the invention, Y denotes H or A. It shall be understood that the respective denotation of Y is independently of one another in any radical of the invention.

It is a preferred embodiment of the m index according to the present invention to be 1 or 2, more preferably 2.

It is a preferred embodiment of the n index according to the present invention to be 0, 1, 2, 3, 4 or 5, more preferably 0, 1, 2, 3 or 4, most preferably 0, 1, 2 or 3. It shall be understood that the respective denotation of n is independently of one another in any radical of the invention.

In another preferred aspect of the invention, one or more of the following compounds are excluded from the scope of formula (I) or any sub-formula thereof:

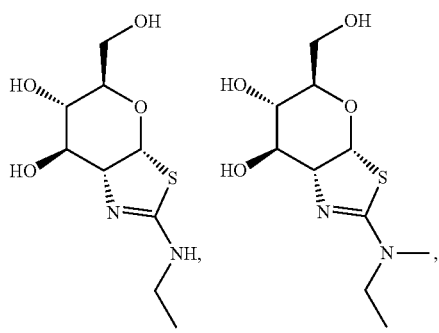

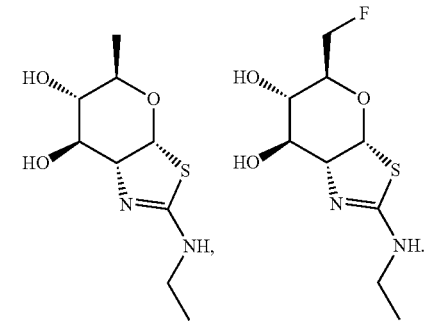

Accordingly, the subject-matter of the invention relates to compounds of formula (I), in which at least one of the aforementioned radicals has any meaning, particularly realize any preferred embodiment, as described above. Radicals, which are not explicitly specified in the context of any embodiment of formula (I), sub-formulae thereof or other radicals thereto, shall be construed to represent any respective denotations according to formula (I) as disclosed hereunder for solving the problem of the invention. That means that the aforementioned radicals may adopt all designated meanings as each described in the prior or following course of the present specification, irrespective of the context to be found, including, but not limited to, any preferred embodiments. It shall be particularly understood that any embodiment of a certain radical can be combined with any embodiment of one or more other radicals.

In another preferred embodiment of the present invention, derivatives of sub-formulae (IA), (IB), (IC) are provided (IA)

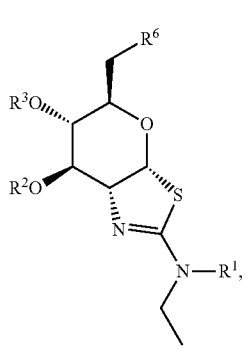

-continued

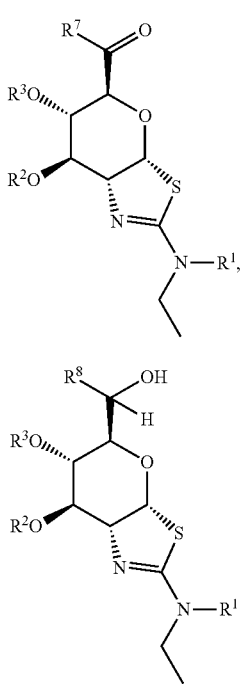
(IB)

(IC)

wherein
R⁶ denotes Hal, Y, OY, OCOOY, COOY, NYY, N=N⁺=N⁻, CAr₃, O—(CH₂)ₙ—Ar, NY—(CH₂)ₙ—Ar or

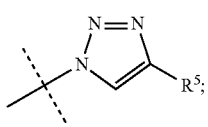

R⁷ denotes Y, OY, NYY, NYOY, (CH₂)ₙ—Ar, NY—(CH₂)ₙ—Ar, NY—(CH₂)ₙ-Cyc, NY—(CH₂)ₙ-Het or

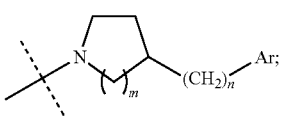

R⁸ denotes (CH₂)ₙ—Ar; and
R¹, R², R³, R⁵, Y, A, Cyc, Ar, Het, Hal, m and n have the meaning as defined above;
and/or physiologically acceptable salts thereof.

It shall be understood that R⁶, R⁷ and R⁸ are different subsets of R⁴ and can also be designated in relation to R⁴, e.g. R⁴⁻¹ᴬ, R⁴⁻¹ᴮ and R⁴⁻¹ᶜ.

It is another preferred embodiment of the present invention that R⁶ denotes Hal, H, OY, OCOOA, COOY, NYY, N=N⁺=N⁻, CAr₃, O—(CH₂)ₙ—Ar, NH—(CH₂)ₙ—Ar or

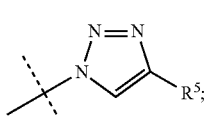

more preferably Hal, H, COOY, CAr₃ or

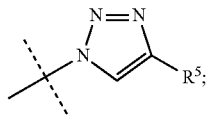

most preferably Hal, COOA or

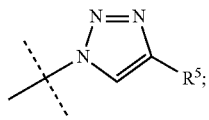

and highly preferably Hal or

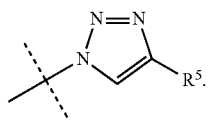

It is another preferred embodiment of the present invention that R⁷ denotes H, OY, NYY, NAOA, (CH₂)ₙ—Ar, NY—(CH₂)ₙ—Ar, NH—(CH₂)ₙ-Cyc, NH—(CH₂)ₙ-Het or

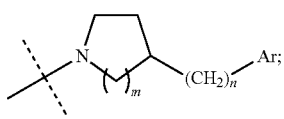

more preferably H, NYY, (CH₂)ₘ—Ar or

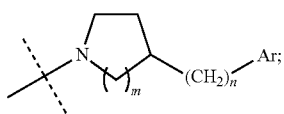

most preferably H, NAA, (CH₂)ₘ—Ar or

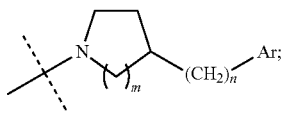

highly preferably H, (CH₂)ₘ—Ar or

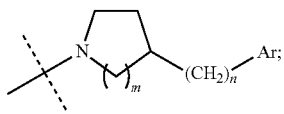

and particularly highly preferably H.

In still another preferred embodiment of the present invention, a compound of sub-formula (IA), (IB) or (IC) is provided

15

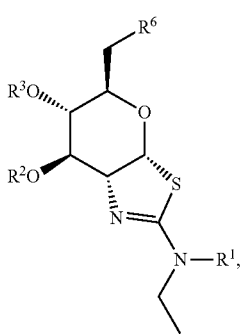

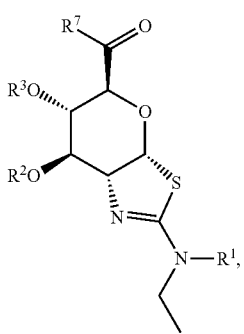

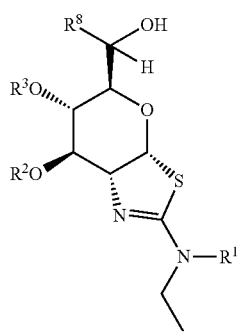

wherein
$R^6$ denotes Hal, H, COOY, CAr$_3$ or

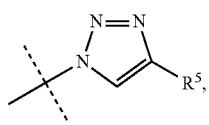

more preferably Cl, Br, I, COOY, CAr$_3$ or

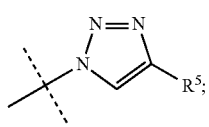

$R^7$ denotes H, (CH$_2$)$_m$—Ar or

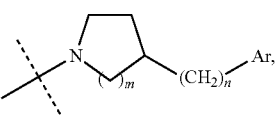

16 more preferably (CH$_2$)$_m$—Ar or

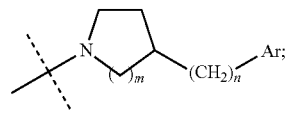

$R^8$ denotes (CH$_2$)$_m$—Ar; and
$R^1$, $R^2$, $R^3$, $R^5$, Y, Ar, Het, Hal, m and n have the meaning as defined above;
and/or a physiologically acceptable salt thereof.

In another more preferred embodiment of the present invention, derivatives of sub-formulae (IA-1), (IA-2), (IB-1) are provided (IA-1)

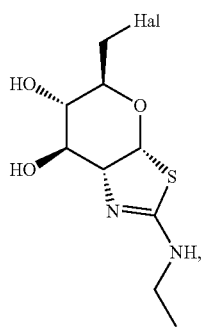

(IA-2)

(IB-1)

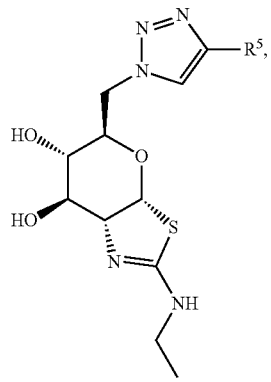

wherein
$R^9$ denotes Y, OY, (CH$_2$)$_n$—Ar, (CH$_2$)$_n$-Cyc or (CH$_2$)$_n$-Het; and $R^5$, Y, A, Cyc, Ar, Het, Hal and n have the meaning as defined above;
and/or physiologically acceptable salts thereof.

It is a preferred embodiment of the present invention that $R^9$ denotes H, OA, $(CH_2)_n$—Ar, $(CH_2)_n$-Cyc or $(CH_2)_n$-Het; preferably NYY; and more preferably NAA.

In still another more preferred embodiment of the present invention, a compound of sub-formula (IA-1) or (IA-2) is provided

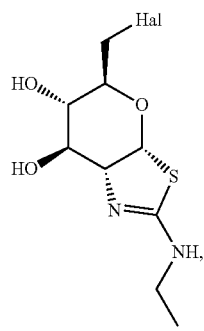
(IA-1)

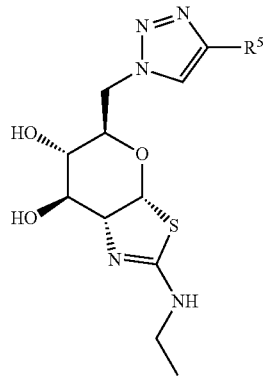
(IA-2)

wherein
$R^5$, Y and Hal have the meaning as defined above;
and/or a physiologically acceptable salt thereof.

It is a more preferred embodiment of Hal to be Cl, Br or I in sub-formula (IA-1).

The prior teaching of the present specification concerning the compounds of formula (I), including any radical definition and preferred embodiment thereof, is valid and applicable without restrictions to the compounds according to sub-formulae (IA), (IA-1), (IA-2), (IB), (IB-1), (IC) and their salts if expedient.

Most preferred embodiments are those compounds of formulae (IA), (IA-1), (IA-2), (IB), (IB-1), (IC) as listed in Table 1.

TABLE 1

Compounds of formulae (IA), (IA-1), (IA-2), (IB), (IB-1), (IC).
OGA enzyme inhibition assay: EXAMPLE 49. OGA cellular inhibition assay: EXAMPLE 50.

| No. | Structure | OGA enzyme inhibition (IC50) 0 > 1 µM + > 0.5-1 µM ++ 0.1-0.5 µM +++ < 0.1 µM | OGA cellular inhibition (EC50) 0 > 1 µM + > 0.5-1 µM ++ 0.1-0.5 µM +++ < 0.1 µM |
|---|---|---|---|
| 1 | 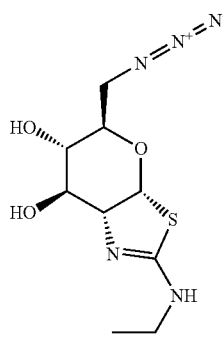 Chiral | +++ | ++ |

TABLE 1-continued
Compounds of formulae (IA), (IA-1), (IA-2), (IB), (IB-1), (IC).
OGA enzyme inhibition assay: EXAMPLE 49. OGA cellular inhibition assay: EXAMPLE 50.
| No. | Structure | | OGA enzyme inhibition (IC50) 0 > 1 μM + > 0.5-1 μM ++ 0.1-0.5 μM +++ < 0.1 μM | OGA cellular inhibition (EC50) 0 > 1 μM + > 0.5-1 μM ++ 0.1-0.5 μM +++ < 0.1 μM |
|---|---|---|---|---|
| 2 | 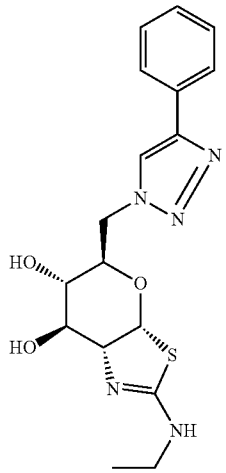 | Chiral | ++ | 0 |
| 3 | 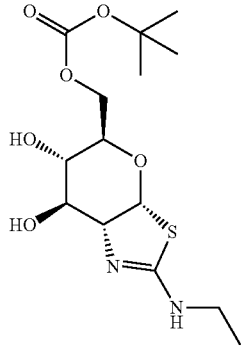 | Chiral | ++ | +++ |
| 4 | 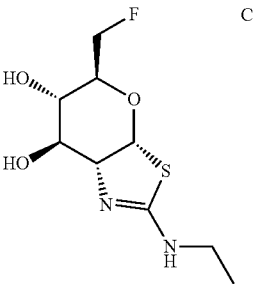 | Chiral comparative example | +++ | ++ |
| 5 | 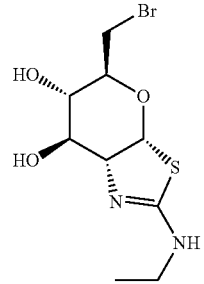 | Chiral | +++ | ++ |

TABLE 1-continued
Compounds of formulae (IA), (IA-1), (IA-2), (IB), (IB-1), (IC).
OGA enzyme inhibition assay: EXAMPLE 49. OGA cellular inhibition assay: EXAMPLE 50.
| No. | Structure | | OGA enzyme inhibition (IC50)<br>0 > 1 μM<br>+ > 0.5-1 μM<br>++ 0.1-0.5 μM<br>+++ < 0.1 μM | OGA cellular inhibition (EC50)<br>0 > 1 μM<br>+ > 0.5-1 μM<br>++ 0.1-0.5 μM<br>+++ < 0.1 μM |
|---|---|---|---|---|
| 6 | 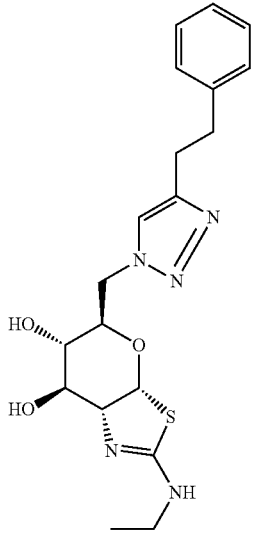 | Chiral | +++ | + |
| 7 | 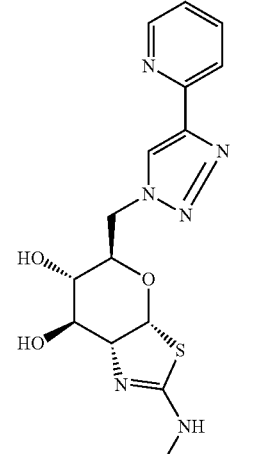 | Chiral | ++ | 0 |
| 8 | 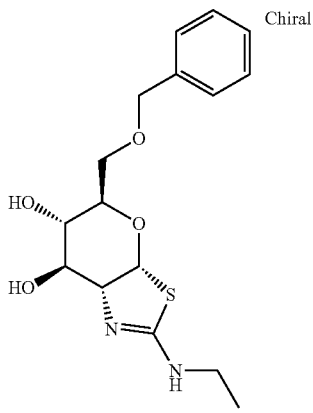 [SMILES: CCNC1=N[C@@H]2[C@@H](O)[C@H](O)[C@@H](COCc3ccccc3)O[C@@H]2S1] | Chiral | 0 | |

TABLE 1-continued

Compounds of formulae (IA), (IA-1), (IA-2), (IB), (IB-1), (IC).
OGA enzyme inhibition assay: EXAMPLE 49. OGA cellular inhibition assay: EXAMPLE 50.

| No. | Structure | OGA enzyme inhibition (IC50) $0 > 1\ \mu M$ $+ > 0.5\text{-}1\ \mu M$ $++\ 0.1\text{-}0.5\ \mu M$ $+++ < 0.1\ \mu M$ | OGA cellular inhibition (EC50) $0 > 1\ \mu M$ $+ > 0.5\text{-}1\ \mu M$ $++\ 0.1\text{-}0.5\ \mu M$ $+++ < 0.1\ \mu M$ |
|---|---|---|---|
| 9 | Chiral | 0 | |
| 10 | Chiral | ++ | + |
| 11 | Chiral | ++ | |

TABLE 1-continued

Compounds of formulae (IA), (IA-1), (IA-2), (IB), (IB-1), (IC).
OGA enzyme inhibition assay: EXAMPLE 49. OGA cellular inhibition assay: EXAMPLE 50.

| No. | Structure | OGA enzyme inhibition (IC50) 0 > 1 µM + > 0.5-1 µM ++ 0.1-0.5 µM +++ < 0.1 µM | OGA cellular inhibition (EC50) 0 > 1 µM + > 0.5-1 µM ++ 0.1-0.5 µM +++ < 0.1 µM |
|---|---|---|---|
| 12 | Chiral | +++ | +++ |
| 13 | Chiral | 0 | |
| 14 | Chiral | +++ | ++ |

TABLE 1-continued
Compounds of formulae (IA), (IA-1), (IA-2), (IB), (IB-1), (IC).
OGA enzyme inhibition assay: EXAMPLE 49. OGA cellular inhibition assay: EXAMPLE 50.
| No. | Structure | | OGA enzyme inhibition (IC50) 0 > 1 μM + > 0.5-1 μM ++ 0.1-0.5 μM +++ < 0.1 μM | OGA cellular inhibition (EC50) 0 > 1 μM + > 0.5-1 μM ++ 0.1-0.5 μM +++ < 0.1 μM |
|---|---|---|---|---|
| 15 | 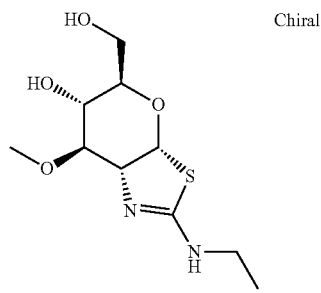 [SMILES: CCNC1=N[C@@H]2[C@@H](OC)[C@H](O)[C@@H](CO)O[C@@H]2S1] | Chiral | 0 | |
| 16 | 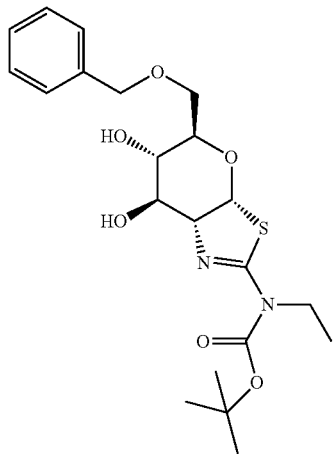 | Chiral | 0 | |
| 17 | 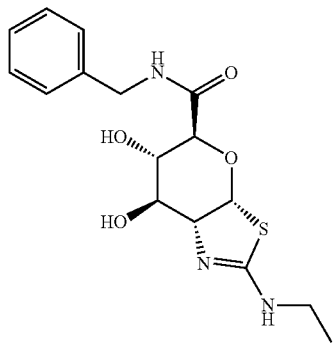 | Chiral | | |

TABLE 1-continued

Compounds of formulae (IA), (IA-1), (IA-2), (IB), (IB-1), (IC).
OGA enzyme inhibition assay: EXAMPLE 49. OGA cellular inhibition assay: EXAMPLE 50.

| No. | Structure | OGA enzyme inhibition (IC50)<br>0 > 1 μM<br>+ > 0.5-1 μM<br>++ 0.1-0.5 μM<br>+++ < 0.1 μM | OGA cellular inhibition (EC50)<br>0 > 1 μM<br>+ > 0.5-1 μM<br>++ 0.1-0.5 μM<br>+++ < 0.1 μM |
|---|---|---|---|
| 18 | Chiral | | |
| 19 | Chiral | + | 0 |
| 20 | Chiral | | |

TABLE 1-continued

Compounds of formulae (IA), (IA-1), (IA-2), (IB), (IB-1), (IC).
OGA enzyme inhibition assay: EXAMPLE 49. OGA cellular inhibition assay: EXAMPLE 50.

| No. | Structure | OGA enzyme inhibition (IC50) 0 > 1 µM + > 0.5-1 µM ++ 0.1-0.5 µM +++ < 0.1 µM | OGA cellular inhibition (EC50) 0 > 1 µM + > 0.5-1 µM ++ 0.1-0.5 µM +++ < 0.1 µM |
|---|---|---|---|
| 21 | Chiral | | |
| 22 | Chiral | | |
| 23 | Chiral | 0 | |
| 24 | Chiral | | |

TABLE 1-continued

Compounds of formulae (IA), (IA-1), (IA-2), (IB), (IB-1), (IC).
OGA enzyme inhibition assay: EXAMPLE 49. OGA cellular inhibition assay: EXAMPLE 50.

| No. | Structure | OGA enzyme inhibition (IC50) 0 > 1 μM + > 0.5-1 μM ++ 0.1-0.5 μM +++ < 0.1 μM | OGA cellular inhibition (EC50) 0 > 1 μM + > 0.5-1 μM ++ 0.1-0.5 μM +++ < 0.1 μM |
|---|---|---|---|
| 25 | Chiral | | |
| 26 | Chiral | | |
| 27 | Chiral | | |
| 28 | Chiral | 0 | |

TABLE 1-continued
Compounds of formulae (IA), (IA-1), (IA-2), (IB), (IB-1), (IC).
OGA enzyme inhibition assay: EXAMPLE 49. OGA cellular inhibition assay: EXAMPLE 50.
| No. | Structure | OGA enzyme inhibition (IC50)<br>0 > 1 μM<br>+ > 0.5-1 μM<br>++ 0.1-0.5 μM<br>+++ < 0.1 μM | OGA cellular inhibition (EC50)<br>0 > 1 μM<br>+ > 0.5-1 μM<br>++ 0.1-0.5 μM<br>+++ < 0.1 μM |
|---|---|---|---|
| 30 | 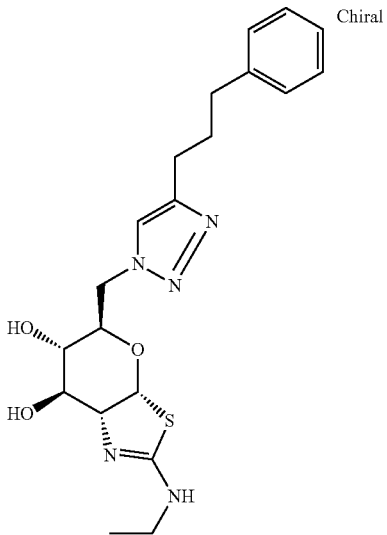 [SMILES: CCNC1=N[C@@H]2[C@@H](O)[C@H](O)[C@@H](Cn3cc(CCCc4ccccc4)nn3)O[C@@H]2S1] Chiral | ++ | 0 |
| 31 | 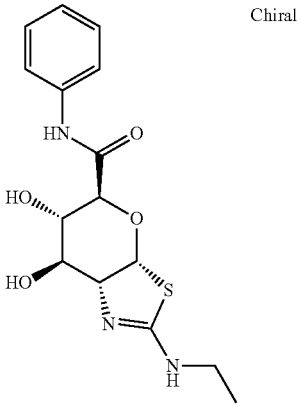 [SMILES: CCNC1=N[C@@H]2[C@@H](O)[C@H](O)[C@@H](C(=O)Nc3ccccc3)O[C@@H]2S1] Chiral | 0 | |
| 32 | 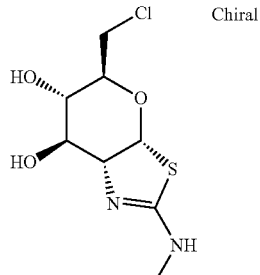 Chiral | +++ | +++ |

TABLE 1-continued

Compounds of formulae (IA), (IA-1), (IA-2), (IB), (IB-1), (IC).
OGA enzyme inhibition assay: EXAMPLE 49. OGA cellular inhibition assay: EXAMPLE 50.

| No. | Structure | OGA enzyme inhibition (IC50) 0 > 1 µM + > 0.5-1 µM ++ 0.1-0.5 µM +++ < 0.1 µM | OGA cellular inhibition (EC50) 0 > 1 µM + > 0.5-1 µM ++ 0.1-0.5 µM +++ < 0.1 µM |
|---|---|---|---|
| 33 | Chiral | | 0 |
| 34 | Chiral | | |
| 35 | Chiral | | |
| 36 | Chiral | | 0 |

TABLE 1-continued

Compounds of formulae (IA), (IA-1), (IA-2), (IB), (IB-1), (IC).
OGA enzyme inhibition assay: EXAMPLE 49. OGA cellular inhibition assay: EXAMPLE 50.

| No. | Structure | OGA enzyme inhibition (IC50) 0 > 1 μM + > 0.5-1 μM ++ 0.1-0.5 μM +++ < 0.1 μM | OGA cellular inhibition (EC50) 0 > 1 μM + > 0.5-1 μM ++ 0.1-0.5 μM +++ < 0.1 μM |
|---|---|---|---|
| 37 | Chiral | | |
| 38 | Chiral | | |
| 39 | Chiral | | |

TABLE 1-continued

Compounds of formulae (IA), (IA-1), (IA-2), (IB), (IB-1), (IC).
OGA enzyme inhibition assay: EXAMPLE 49. OGA cellular inhibition assay: EXAMPLE 50.

| No. | Structure | OGA enzyme inhibition (IC50)<br>0 > 1 µM<br>+ > 0.5-1 µM<br>++ 0.1-0.5 µM<br>+++ < 0.1 µM | OGA cellular inhibition (EC50)<br>0 > 1 µM<br>+ > 0.5-1 µM<br>++ 0.1-0.5 µM<br>+++ < 0.1 µM |
|---|---|---|---|
| 40 | Chiral | | |
| 41 | Chiral | | |
| 42 | Chiral | 0 | |

TABLE 1-continued

Compounds of formulae (IA), (IA-1), (IA-2), (IB), (IB-1), (IC).
OGA enzyme inhibition assay: EXAMPLE 49. OGA cellular inhibition assay: EXAMPLE 50.

| No. | Structure | | OGA enzyme inhibition (IC50)<br>0 > 1 μM<br>+ > 0.5-1 μM<br>++ 0.1-0.5 μM<br>+++ < 0.1 μM | OGA cellular inhibition (EC50)<br>0 > 1 μM<br>+ > 0.5-1 μM<br>++ 0.1-0.5 μM<br>+++ < 0.1 μM |
|---|---|---|---|---|
| 43 | 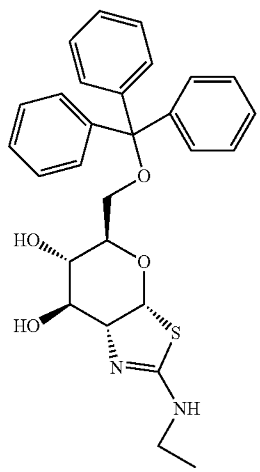 | Chiral | + | 0 |
| 44 | 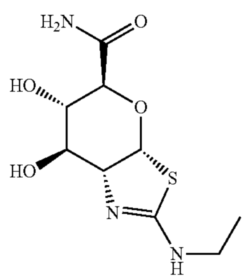 | Chiral | | |
| 45 | 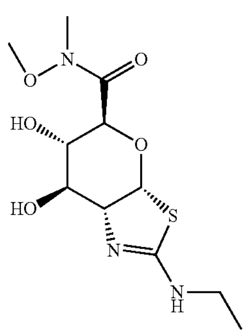 | Chiral | 0 | |
| 46 | 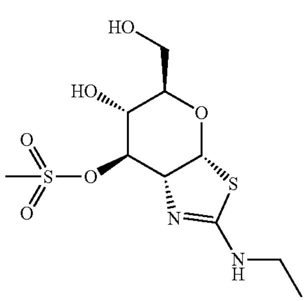 | Chiral | ++ | ++ |

TABLE 1-continued

Compounds of formulae (IA), (IA-1), (IA-2), (IB), (IB-1), (IC).
OGA enzyme inhibition assay: EXAMPLE 49. OGA cellular inhibition assay: EXAMPLE 50.

| No. | Structure | OGA enzyme inhibition (IC50) 0 > 1 μM + > 0.5-1 μM ++ 0.1-0.5 μM +++ < 0.1 μM | OGA cellular inhibition (EC50) 0 > 1 μM + > 0.5-1 μM ++ 0.1-0.5 μM +++ < 0.1 μM |
|---|---|---|---|
| 47 | Chiral | | +++ |
| 48 | Chiral | | + |
| 49 | Chiral | | +++ |

TABLE 1-continued
Compounds of formulae (IA), (IA-1), (IA-2), (IB), (IB-1), (IC).
OGA enzyme inhibition assay: EXAMPLE 49. OGA cellular inhibition assay: EXAMPLE 50.
| No. | Structure | OGA enzyme inhibition (IC50) 0 > 1 μM + > 0.5-1 μM ++ 0.1-0.5 μM +++ < 0.1 μM | OGA cellular inhibition (EC50) 0 > 1 μM + > 0.5-1 μM ++ 0.1-0.5 μM +++ < 0.1 μM |
|---|---|---|---|
| 50 | 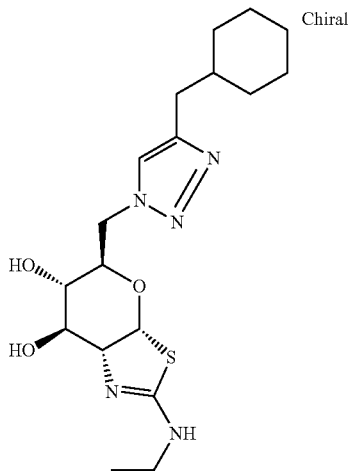 [SMILES: CCNC1=N[C@@H]2[C@@H](O)[C@H](O)[C@@H](Cn3cc(CC4CCCCC4)nn3)O[C@@H]2S1] Chiral | +++ | + |
| 51 | 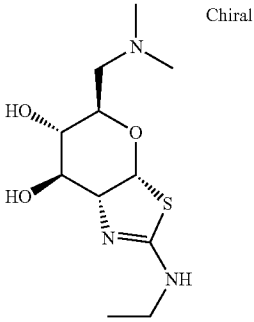 [SMILES: CCNC1=N[C@@H]2[C@@H](O)[C@H](O)[C@@H](CN(C)C)O[C@@H]2S1] Chiral | ++ | ++ |
| 52 | 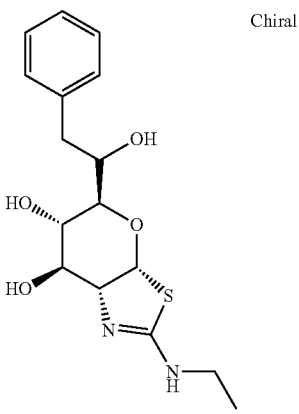 [SMILES: CCNC1=N[C@@H]2[C@@H](O)[C@H](O)[C@@H](C(O)Cc3ccccc3)O[C@@H]2S1] Chiral | ++ | |

… 49 …                                                             … 50 …
TABLE 1-continued
Compounds of formulae (IA), (IA-1), (IA-2), (IB), (IB-1), (IC).
OGA enzyme inhibition assay: EXAMPLE 49. OGA cellular inhibition assay: EXAMPLE 50.
| No. | Structure | OGA enzyme inhibition (IC50)<br>0 > 1 μM<br>+ > 0.5-1 μM<br>++ 0.1-0.5 μM<br>+++ < 0.1 μM | OGA cellular inhibition (EC50)<br>0 > 1 μM<br>+ > 0.5-1 μM<br>++ 0.1-0.5 μM<br>+++ < 0.1 μM |
|---|---|---|---|
| 53 | 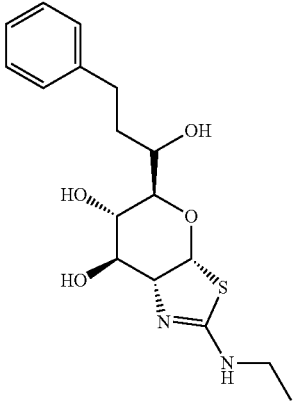 Chiral | ++ | ++ |
| 54 | 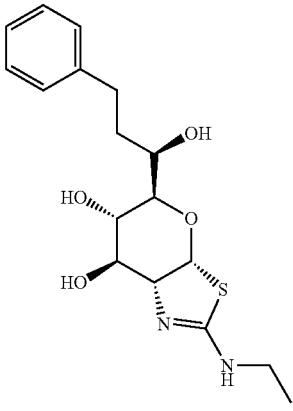 Chiral | 0 | |
| 55 | 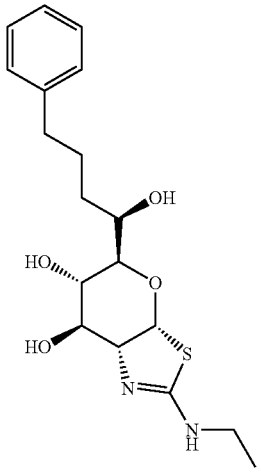 Chiral | 0 | |

TABLE 1-continued
Compounds of formulae (IA), (IA-1), (IA-2), (IB), (IB-1), (IC).
OGA enzyme inhibition assay: EXAMPLE 49. OGA cellular inhibition assay: EXAMPLE 50.
| No. | Structure | | OGA enzyme inhibition (IC50) 0 > 1 μM + > 0.5-1 μM ++ 0.1-0.5 μM +++ < 0.1 μM | OGA cellular inhibition (EC50) 0 > 1 μM + > 0.5-1 μM ++ 0.1-0.5 μM +++ < 0.1 μM |
|---|---|---|---|---|
| 56 | 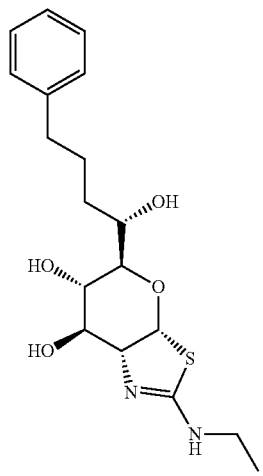 | Chiral | ++ | |
| 57 | 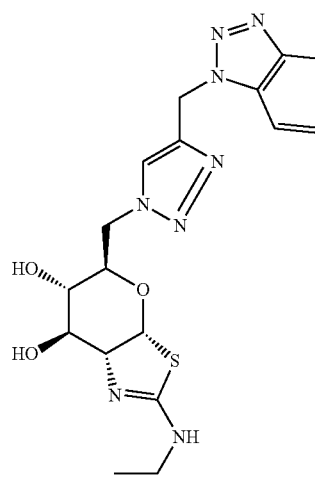 | Chiral | +++ | 0 |

TABLE 1-continued
Compounds of formulae (IA), (IA-1), (IA-2), (IB), (IB-1), (IC).
OGA enzyme inhibition assay: EXAMPLE 49. OGA cellular inhibition assay: EXAMPLE 50.
| No. | Structure | OGA enzyme inhibition (IC50)<br>0 > 1 µM<br>+ > 0.5-1 µM<br>++ 0.1-0.5 µM<br>+++ < 0.1 µM | OGA cellular inhibition (EC50)<br>0 > 1 µM<br>+ > 0.5-1 µM<br>++ 0.1-0.5 µM<br>+++ < 0.1 µM |
|---|---|---|---|
| 58 | Chiral 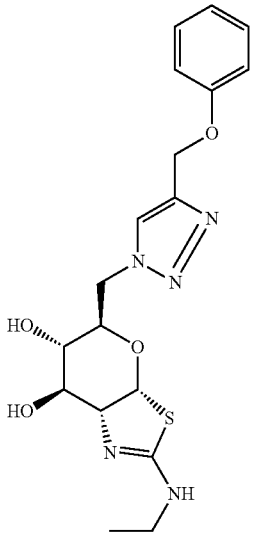 | +++ | + |
| 59 | Chiral 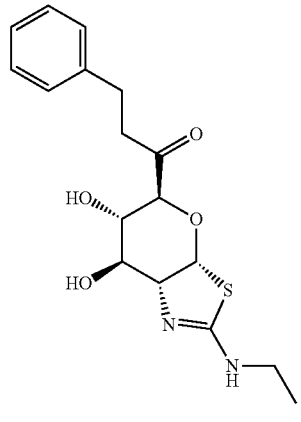 | 0 | |
| 60 | Chiral 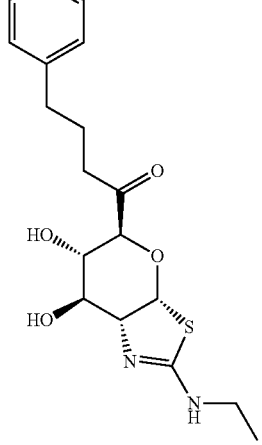 | 0 | |

TABLE 1-continued

Compounds of formulae (IA), (IA-1), (IA-2), (IB), (IB-1), (IC).
OGA enzyme inhibition assay: EXAMPLE 49. OGA cellular inhibition assay: EXAMPLE 50.

| No. | Structure | | OGA enzyme inhibition (IC50) 0 > 1 μM + > 0.5-1 μM ++ 0.1-0.5 μM +++ < 0.1 μM | OGA cellular inhibition (EC50) 0 > 1 μM + > 0.5-1 μM ++ 0.1-0.5 μM +++ < 0.1 μM |
|---|---|---|---|---|
| 61 | [structure] | Chiral | ++ | |
| 62 | [structure] | Chiral | ++ | |
| 63 | [structure] | Chiral | ++ | |
| 64 | [structure] | Chiral | | |

TABLE 1-continued
Compounds of formulae (IA), (IA-1), (IA-2), (IB), (IB-1), (IC).
OGA enzyme inhibition assay: EXAMPLE 49. OGA cellular inhibition assay: EXAMPLE 50.
| No. | Structure | | OGA enzyme inhibition (IC50)<br>0 > 1 μM<br>+ > 0.5-1 μM<br>++ 0.1-0.5 μM<br>+++ < 0.1 μM | OGA cellular inhibition (EC50)<br>0 > 1 μM<br>+ > 0.5-1 μM<br>++ 0.1-0.5 μM<br>+++ < 0.1 μM |
|---|---|---|---|---|
| 65 | 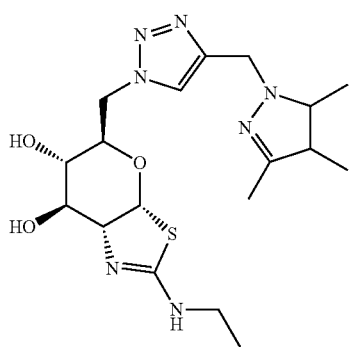 | Chiral | +++ | 0 |
| 66 | 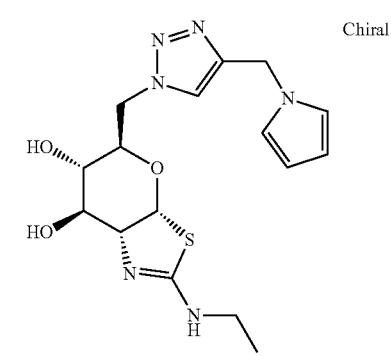 [SMILES: CCNC1=N[C@@H]2[C@@H](O)[C@H](O)[C@@H](Cn3cc(Cn4cccc4)nn3)O[C@@H]2S1] | Chiral | +++ | 0 |
| 67 | 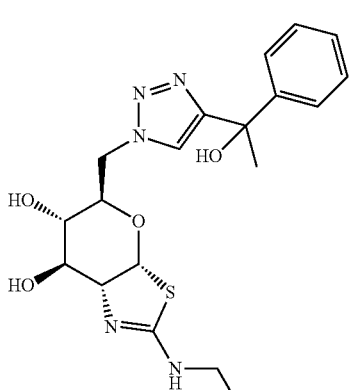 | Chiral | +++ | +++ |
| 68 | 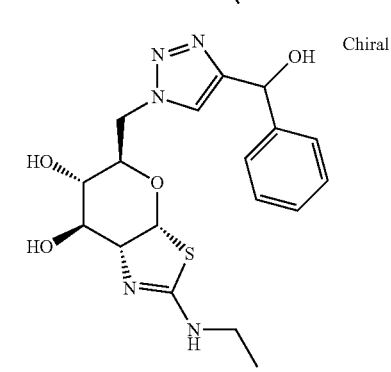 | Chiral | +++ | 0 |

TABLE 1-continued
Compounds of formulae (IA), (IA-1), (IA-2), (IB), (IB-1), (IC).
OGA enzyme inhibition assay: EXAMPLE 49. OGA cellular inhibition assay: EXAMPLE 50.
| No. | Structure | OGA enzyme inhibition (IC50) 0 > 1 µM + > 0.5-1 µM ++ 0.1-0.5 µM +++ < 0.1 µM | OGA cellular inhibition (EC50) 0 > 1 µM + > 0.5-1 µM ++ 0.1-0.5 µM +++ < 0.1 µM |
|---|---|---|---|
| 69 | Chiral 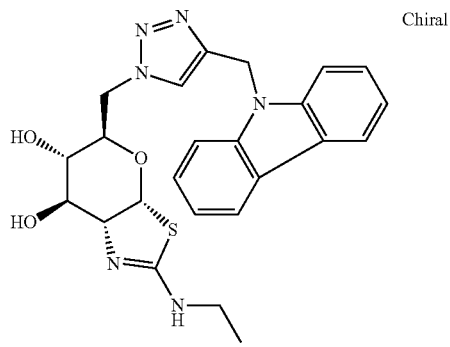 [SMILES: CCNC1=N[C@@H]2[C@@H](O)[C@H](O)[C@@H](Cn3cc(Cn4c5ccccc5c5ccccc54)nn3)O[C@@H]2S1] | ++ | ++ |
| 70 | Chiral 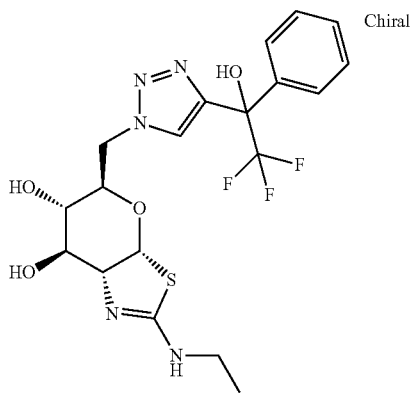 [SMILES: CCNC1=N[C@@H]2[C@@H](O)[C@H](O)[C@@H](Cn3cc(C(O)(c4ccccc4)C(F)(F)F)nn3)O[C@@H]2S1] | +++ | 0 |
| 71 | Chiral 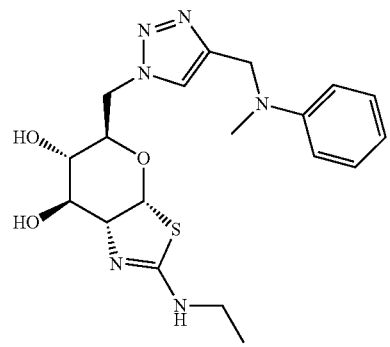 | ++ | 0 |

TABLE 1-continued

Compounds of formulae (IA), (IA-1), (IA-2), (IB), (IB-1), (IC).
OGA enzyme inhibition assay: EXAMPLE 49. OGA cellular inhibition assay: EXAMPLE 50.

| No. | Structure | | OGA enzyme inhibition (IC50) 0 > 1 μM + > 0.5-1 μM ++ 0.1-0.5 μM +++ < 0.1 μM | OGA cellular inhibition (EC50) 0 > 1 μM + > 0.5-1 μM ++ 0.1-0.5 μM +++ < 0.1 μM |
|---|---|---|---|---|
| 72 | [structure with 3-bromophenoxy group] | Chiral | +++ | ++ |
| 73 | [structure with 3-cyanophenoxy group] | Chiral | +++ | + |
| 74 | [structure with 3-hydroxyphenoxy group] | Chiral | +++ | 0 |
| 75 | [structure with 3-(hydroxymethyl)phenoxy group] | Chiral | +++ | 0 |

TABLE 1-continued

Compounds of formulae (IA), (IA-1), (IA-2), (IB), (IB-1), (IC).
OGA enzyme inhibition assay: EXAMPLE 49. OGA cellular inhibition assay: EXAMPLE 50.

| No. | Structure | | OGA enzyme inhibition (IC50) 0 > 1 μM + > 0.5-1 μM ++ 0.1-0.5 μM +++ < 0.1 μM | OGA cellular inhibition (EC50) 0 > 1 μM + > 0.5-1 μM ++ 0.1-0.5 μM +++ < 0.1 μM |
|---|---|---|---|---|
| 76 | 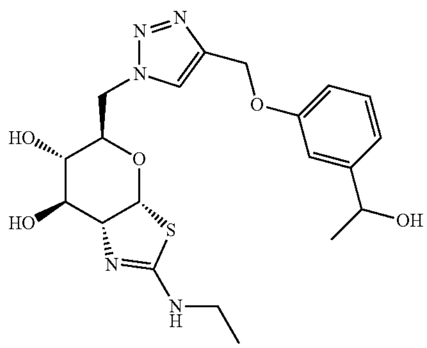 | Chiral | +++ | 0 |
| 77 | 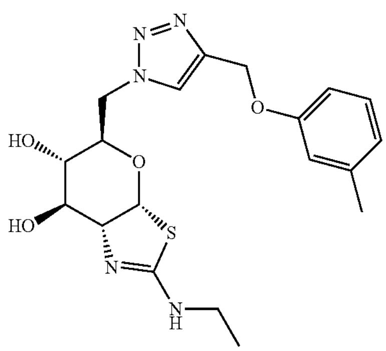 | Chiral | +++ | ++ |
| 78 | 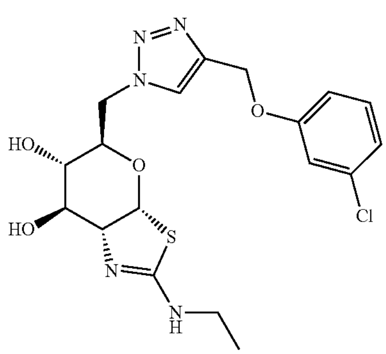 | Chiral | +++ | +++ |
| 79 | 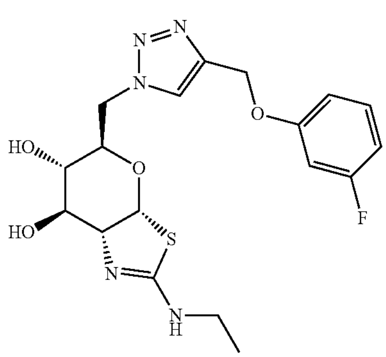 | Chiral | +++ | ++ |

TABLE 1-continued

Compounds of formulae (IA), (IA-1), (IA-2), (IB), (IB-1), (IC).
OGA enzyme inhibition assay: EXAMPLE 49. OGA cellular inhibition assay: EXAMPLE 50.

| No. | Structure | | OGA enzyme inhibition (IC50) 0 > 1 µM + > 0.5-1 µM ++ 0.1-0.5 µM +++ < 0.1 µM | OGA cellular inhibition (EC50) 0 > 1 µM + > 0.5-1 µM ++ 0.1-0.5 µM +++ < 0.1 µM |
|---|---|---|---|---|
| 80 | 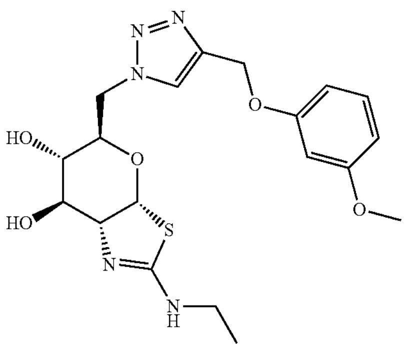 | Chiral | +++ | ++ |
| 81 | 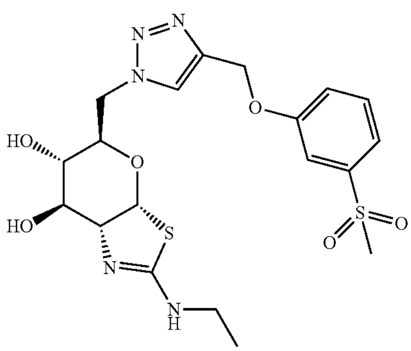 | Chiral | +++ | 0 |
| 82 | 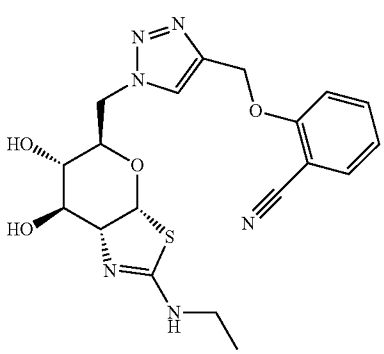 | Chiral | +++ | 0 |
| 83 | 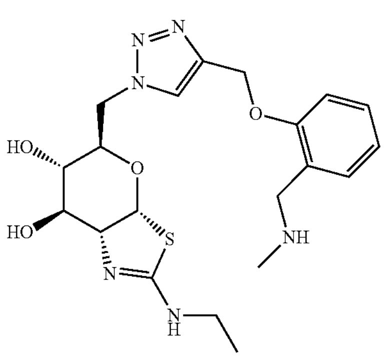 | Chiral | + | |

TABLE 1-continued

Compounds of formulae (IA), (IA-1), (IA-2), (IB), (IB-1), (IC).
OGA enzyme inhibition assay: EXAMPLE 49. OGA cellular inhibition assay: EXAMPLE 50.

| No. | Structure | | OGA enzyme inhibition (IC50) 0 > 1 μM + > 0.5-1 μM ++ 0.1-0.5 μM +++ < 0.1 μM | OGA cellular inhibition (EC50) 0 > 1 μM + > 0.5-1 μM ++ 0.1-0.5 μM +++ < 0.1 μM |
|---|---|---|---|---|
| 84 | 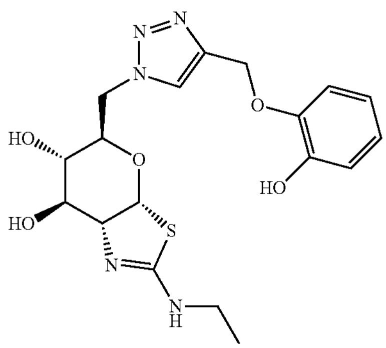 | Chiral | ++ | 0 |
| 85 | 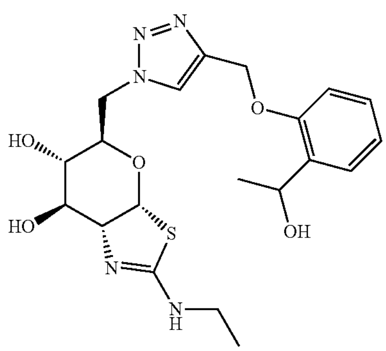 | Chiral | ++ | |
| 86 | 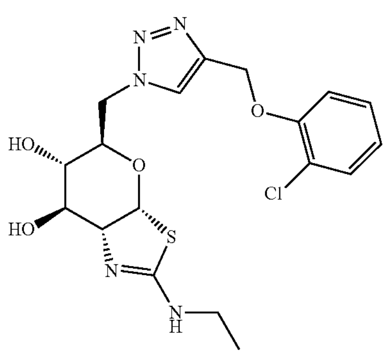 | Chiral | +++ | +++ |
| 87 | 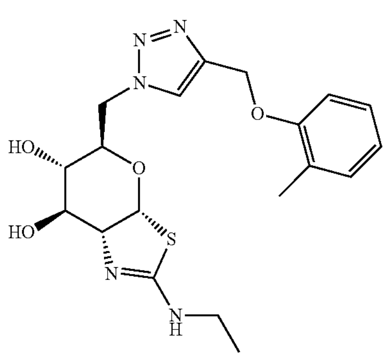 | Chiral | +++ | + |

TABLE 1-continued

Compounds of formulae (IA), (IA-1), (IA-2), (IB), (IB-1), (IC).
OGA enzyme inhibition assay: EXAMPLE 49. OGA cellular inhibition assay: EXAMPLE 50.

| No. | Structure | | OGA enzyme inhibition (IC50) 0 > 1 μM + > 0.5-1 μM ++ 0.1-0.5 μM +++ < 0.1 μM | OGA cellular inhibition (EC50) 0 > 1 μM + > 0.5-1 μM ++ 0.1-0.5 μM +++ < 0.1 μM |
|---|---|---|---|---|
| 88 | 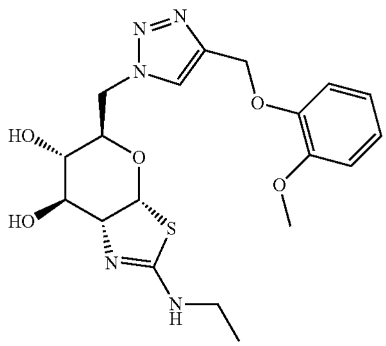 | Chiral | +++ | 0 |
| 89 | 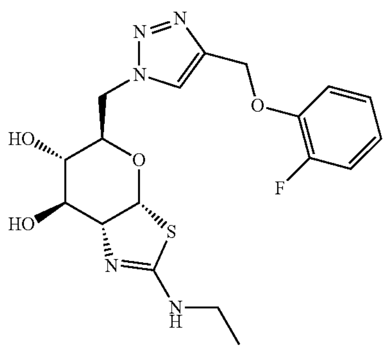 | Chiral | +++ | ++ |
| 90 | 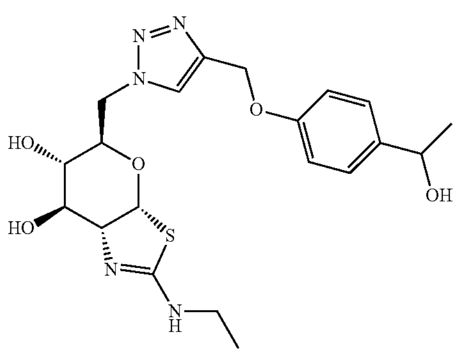 | Chiral | +++ | 0 |
| 91 | 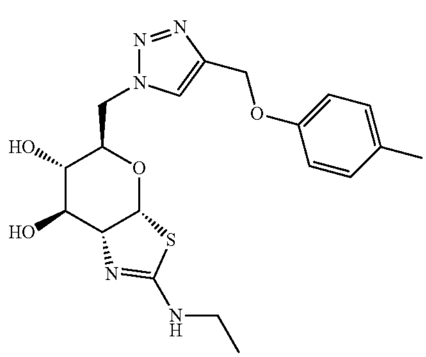 | Chiral | ++ | 0 |

TABLE 1-continued

Compounds of formulae (IA), (IA-1), (IA-2), (IB), (IB-1), (IC).
OGA enzyme inhibition assay: EXAMPLE 49. OGA cellular inhibition assay: EXAMPLE 50.

| No. | Structure | | OGA enzyme inhibition (IC50) 0 > 1 µM + > 0.5-1 µM ++ 0.1-0.5 µM +++ < 0.1 µM | OGA cellular inhibition (EC50) 0 > 1 µM + > 0.5-1 µM ++ 0.1-0.5 µM +++ < 0.1 µM |
|---|---|---|---|---|
| 92 | 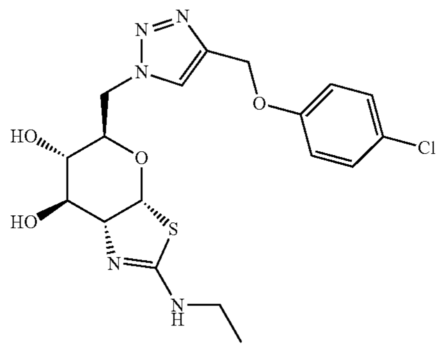 | Chiral | +++ | ++ |
| 93 | 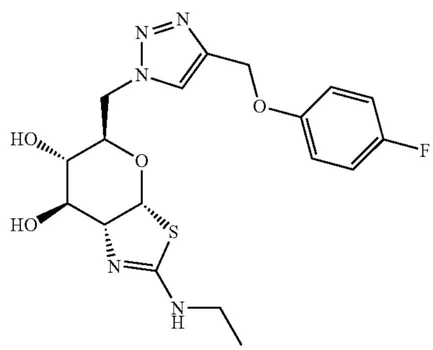 | Chiral | +++ | 0 |
| 94 | 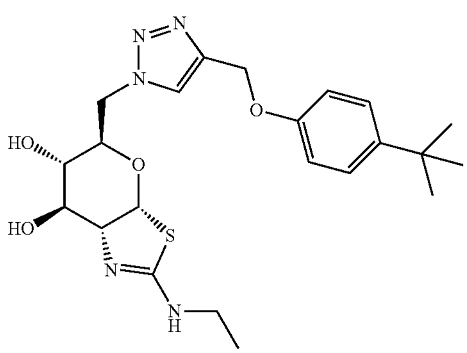 | Chiral | ++ | ++ |
| 95 | 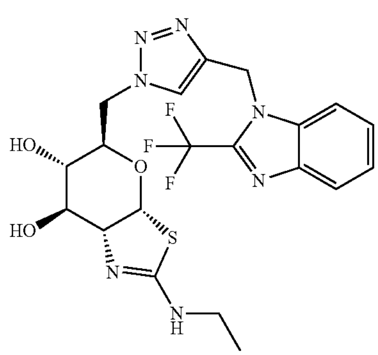 | Chiral | +++ | |

TABLE 1-continued

Compounds of formulae (IA), (IA-1), (IA-2), (IB), (IB-1), (IC).
OGA enzyme inhibition assay: EXAMPLE 49. OGA cellular inhibition assay: EXAMPLE 50.

| No. | Structure | | OGA enzyme inhibition (IC50) 0 > 1 μM + > 0.5-1 μM ++ 0.1-0.5 μM +++ < 0.1 μM | OGA cellular inhibition (EC50) 0 > 1 μM + > 0.5-1 μM ++ 0.1-0.5 μM +++ < 0.1 μM |
|---|---|---|---|---|
| 96 | 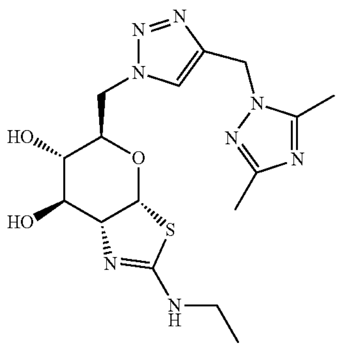 | Chiral | +++ | |
| 97 | 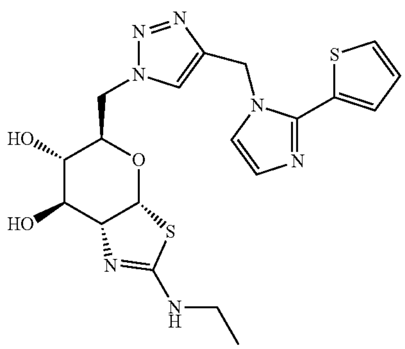 | Chiral | +++ | |
| 98 | 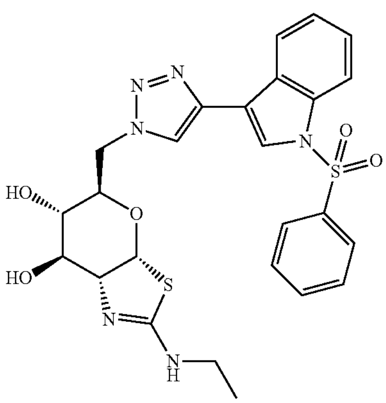 | Chiral | +++ | |
| 99 | 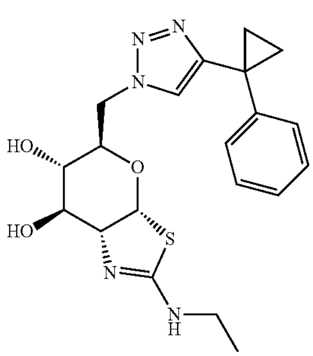 | Chiral | +++ | |

TABLE 1-continued
Compounds of formulae (IA), (IA-1), (IA-2), (IB), (IB-1), (IC).
OGA enzyme inhibition assay: EXAMPLE 49. OGA cellular inhibition assay: EXAMPLE 50.
| No. | Structure | OGA enzyme inhibition (IC50) 0 > 1 μM + > 0.5-1 μM ++ 0.1-0.5 μM +++ < 0.1 μM | OGA cellular inhibition (EC50) 0 > 1 μM + > 0.5-1 μM ++ 0.1-0.5 μM +++ < 0.1 μM |
|---|---|---|---|
| 100 | 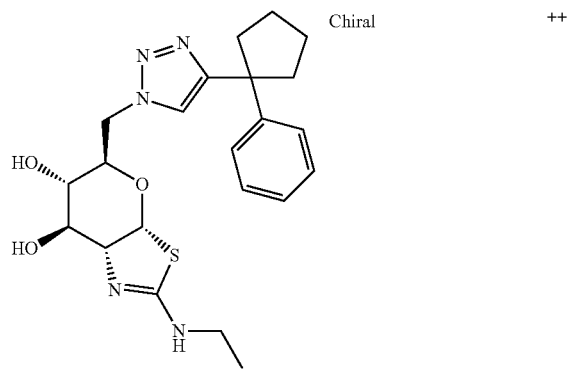 Chiral | | ++ |
| 101 | 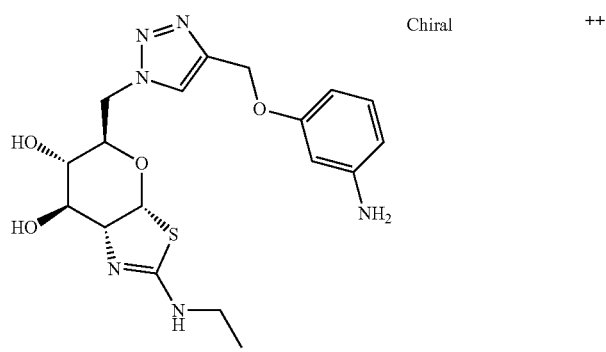 Chiral | | ++ |
| 102 | 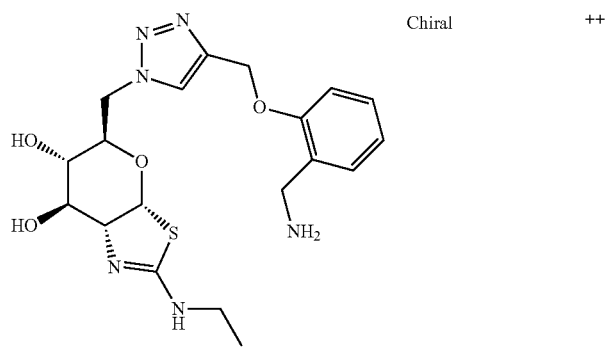 Chiral | | ++ |

TABLE 1-continued

Compounds of formulae (IA), (IA-1), (IA-2), (IB), (IB-1), (IC).
OGA enzyme inhibition assay: EXAMPLE 49. OGA cellular inhibition assay: EXAMPLE 50.

| No. | Structure | OGA enzyme inhibition (IC50) 0 > 1 µM + > 0.5-1 µM ++ 0.1-0.5 µM +++ < 0.1 µM | OGA cellular inhibition (EC50) 0 > 1 µM + > 0.5-1 µM ++ 0.1-0.5 µM +++ < 0.1 µM |
|---|---|---|---|
| 103 | Chiral structure | | |
| 104 | Chiral structure | | |
| 105 | structure | 0 | |

Highly preferred embodiments are the compounds selected from the group of
5
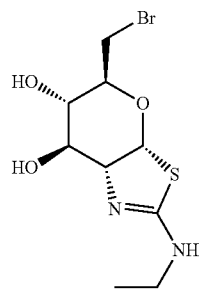
6
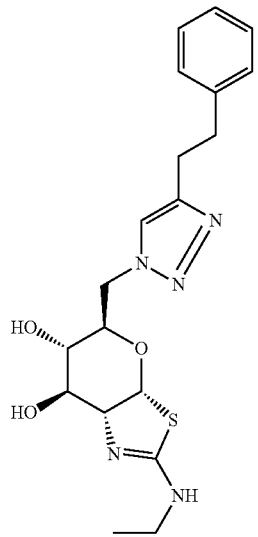
14
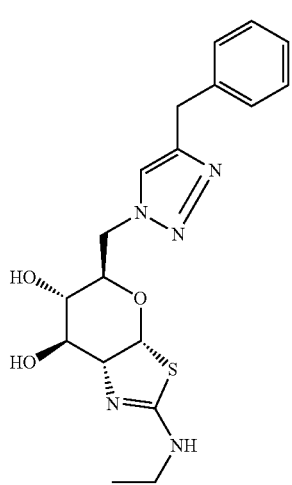
32
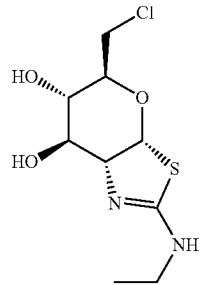
47
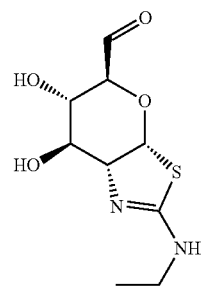
50
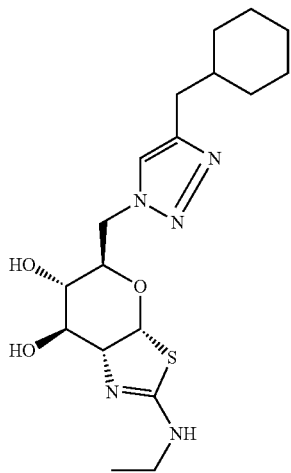
57
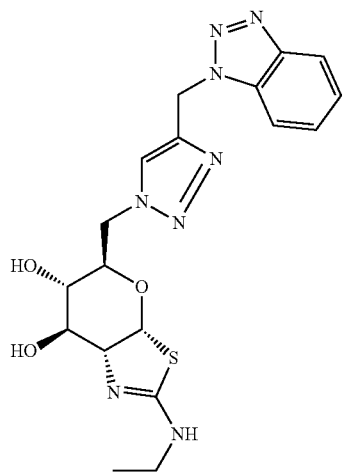

| 58 | 67 |
|---|---|
| 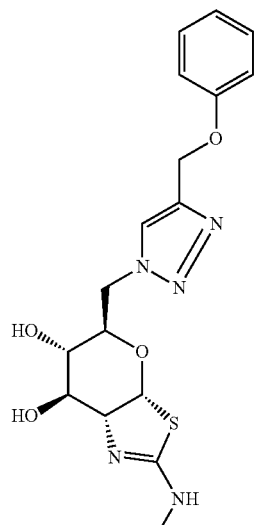 | 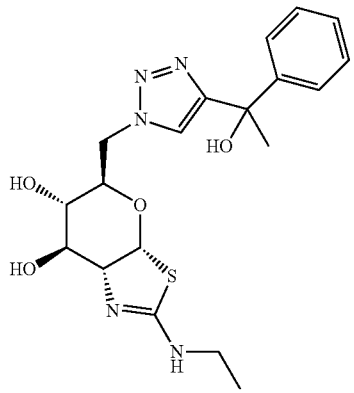 |
| 65 | 68 |
| 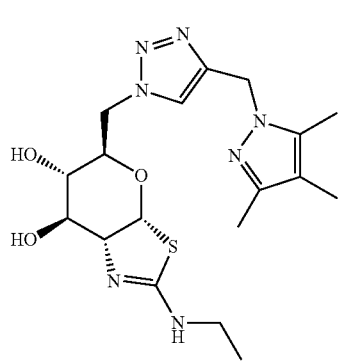 | 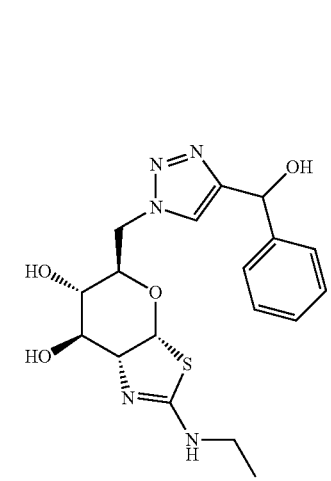 |
| 66 | 70 |
| 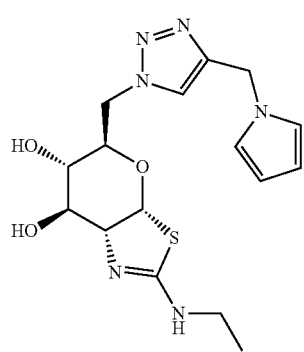 | 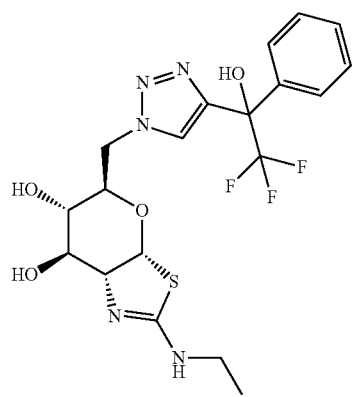 |

72
Chiral
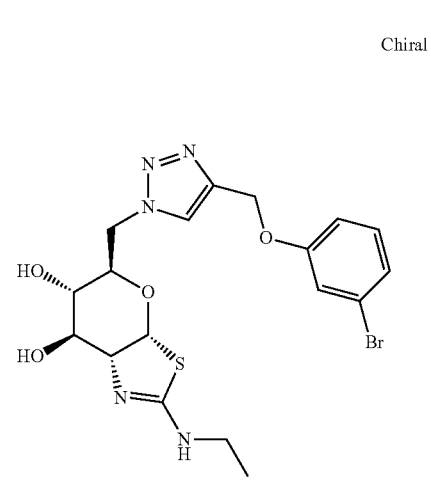
73
Chiral
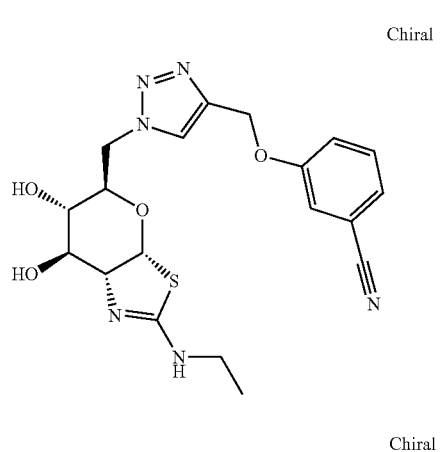
74
Chiral
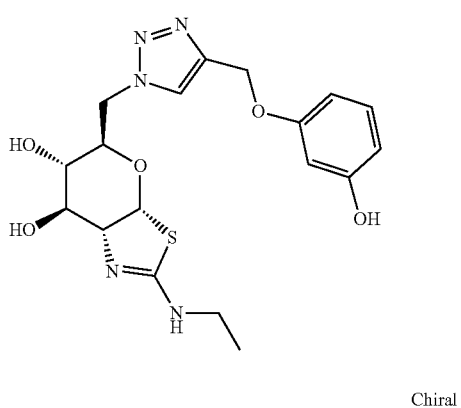
75
Chiral
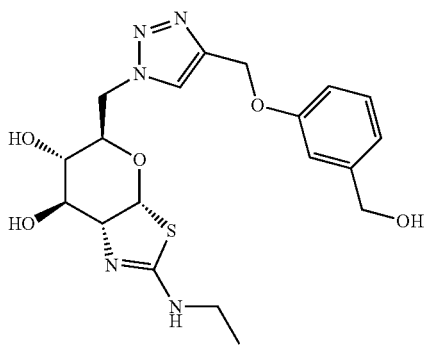
76
Chiral
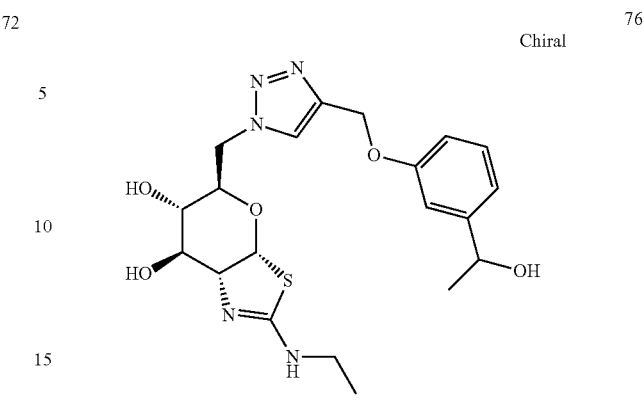
77
Chiral
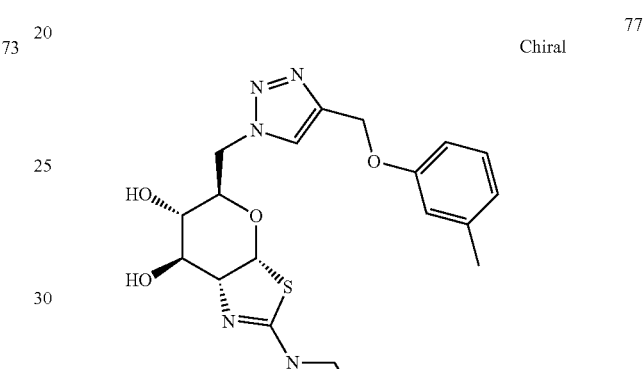
78
Chiral
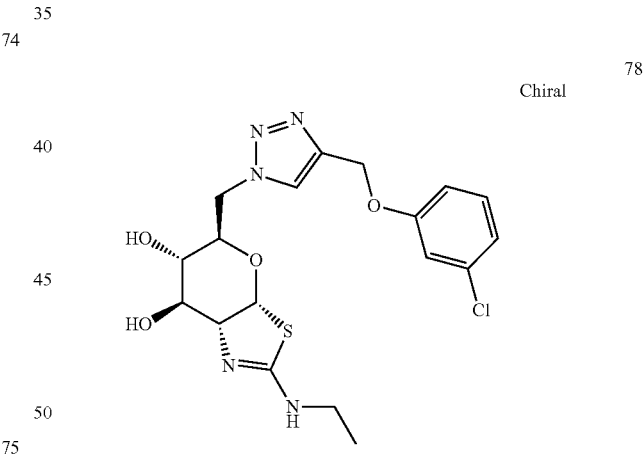
79
Chiral
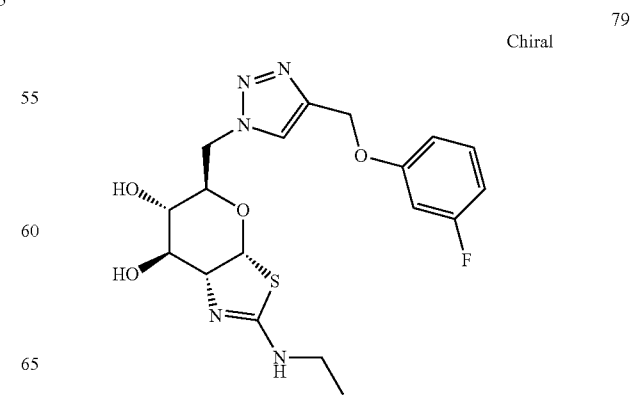

80
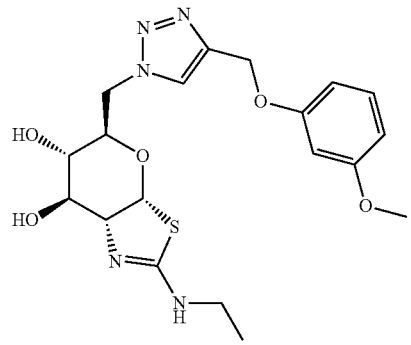
81
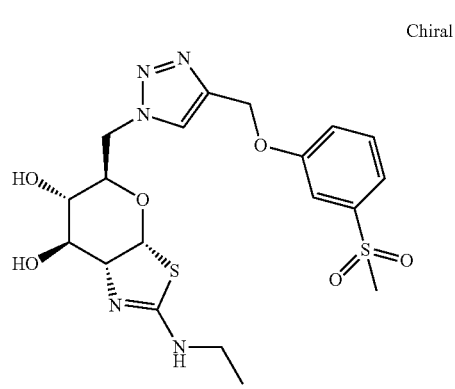
82
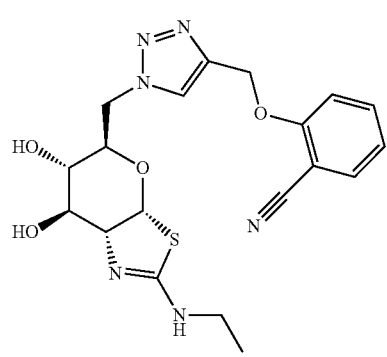
86
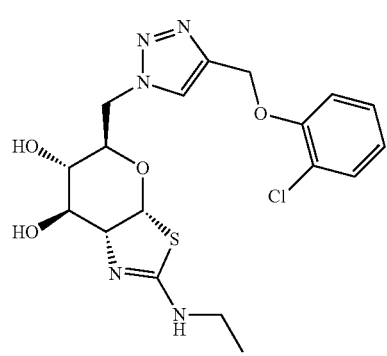
87
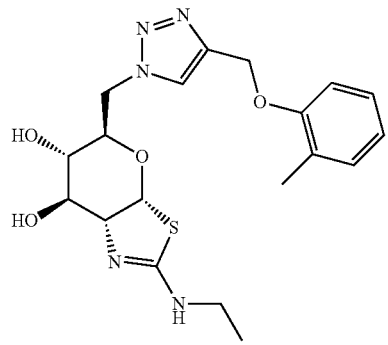
88
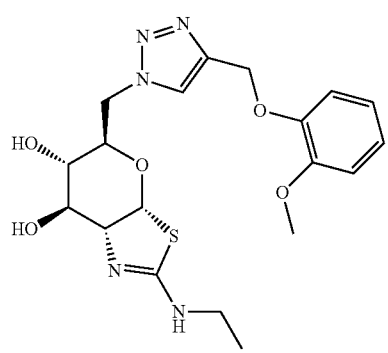
89
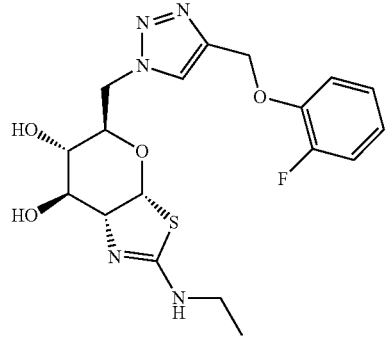
90
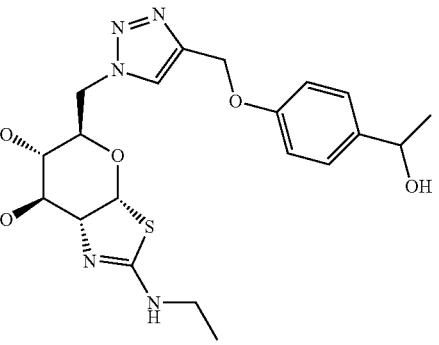

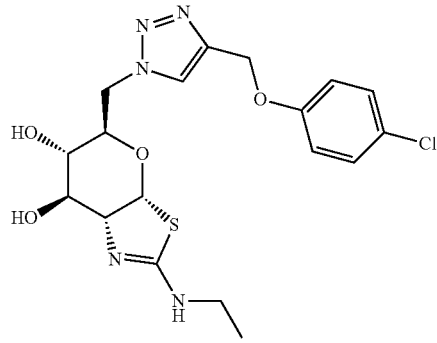
92
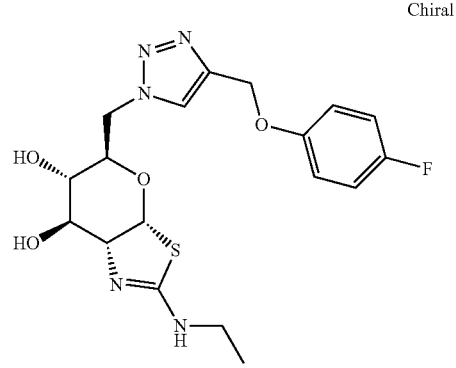
93
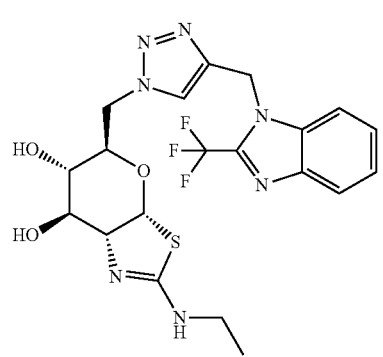
95
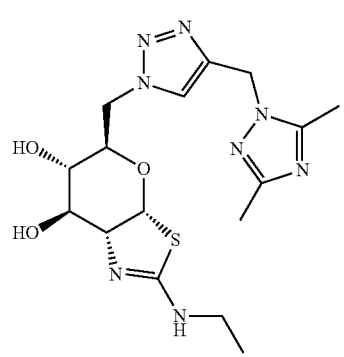
96
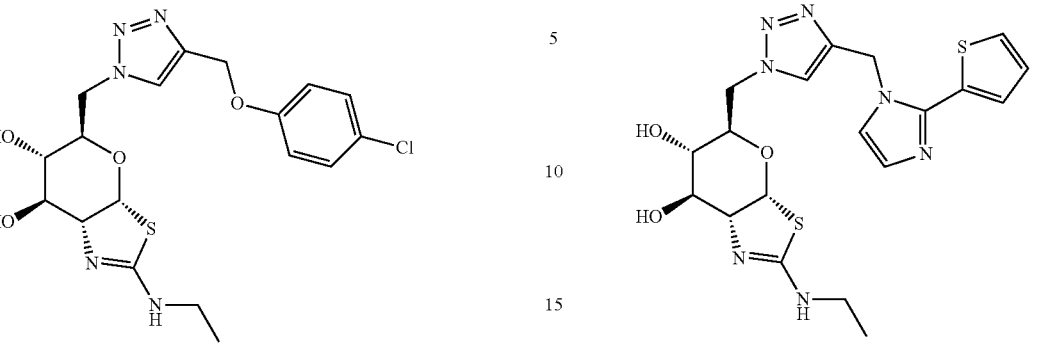
and/or physiologically acceptable salts thereof.
Particularly highly preferred embodiments are the compounds selected from the group of

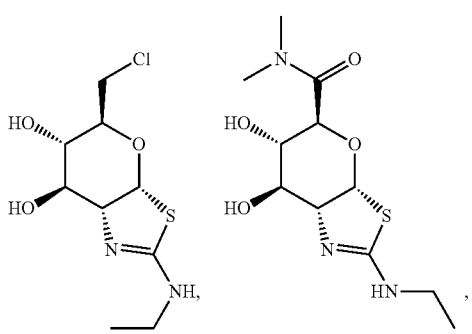

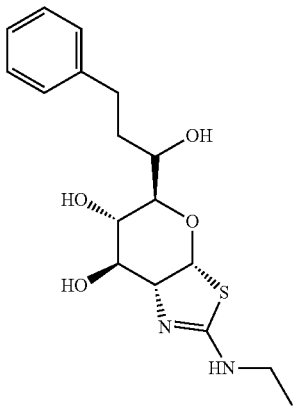

and/or physiologically acceptable salts thereof.

The compounds according to formula (I) and the starting materials for its preparation, respectively, are produced by methods known per se, as described in the literature (for example in standard works, such as Houben-Weyl, Methoden der organischen Chemie [Methods of Organic Chemistry], Georg-Thieme-Verlag, Stuttgart), i.e. under reaction conditions that are known and suitable for said reactions.

Use can also be made of variants that are known per se, but are not mentioned in greater detail herein. If desired, the starting materials can also be formed in-situ by leaving them in the un-isolated status in the crude reaction mixture, but immediately converting them further into the compound according to the invention. On the other hand, it is possible to carry out the reaction stepwise.

The reactions are preferably performed under basic conditions. Suitable bases are metal oxides, e.g. aluminum oxide, alkaline metal hydroxide (potassium hydroxide, sodium hydroxide and lithium hydroxide, inter alia), alkaline earth metal hydroxide (barium hydroxide and calcium hydroxide, inter alia), alkaline metal alcoholates (potassium ethanolate and sodium propanolate, inter alia), alkaline metal carbonates (e.g., sodium bicarbonate) and several organic bases (e.g., N,N-diisopropylethylamine, piperidine or diethanolamine, inter alia).

The reaction is generally carried out in an inert solvent. Suitable inert solvents are, for example, hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid, acetic acid or trifluoroacetic acid (TFA); nitro compounds, such as nitromethane or nitrobenzene; esters, such as ethyl acetate, or mixtures of the said solvents. Particular preference is given to DMF, dichloromethane, THF, $H_2O$, methanol, TFA, tert.butanol, tert.amylalcohol, triethylamine or dioxane.

Depending on the conditions used, the reaction time is between a few minutes and 14 days, the reaction temperature is between about −30° C. and 140° C., normally between −10° C. and 130° C., preferably between 30° C. and 125° C.

The present invention also relates to a process for manufacturing compounds of formula (I) comprising the steps of:
(a) performing a one-pot or multiple-pot synthesis by reacting a compound of formula (II), in the presence of a solvent,

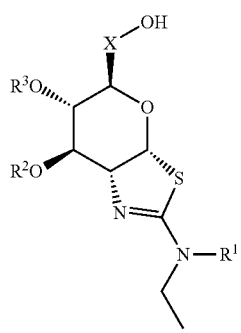

wherein $R^1$ to $R^3$ and X have the meaning as defined above, to yield a compound of formula (I)

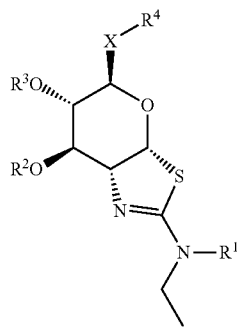

wherein $R^1$ to $R^4$ and X have the meaning as defined above, and optionally
(b) converting a base or an acid of the compound of formula (I) into a salt thereof.

Compound nos. 1, 9 and 45 can be preferably used as intermediates, more preferably as intermediates for the preparation of other compounds in the meaning of the invention. Another preferred intermediate of the invention is (3aR,5R,6S,7R,7aR)-2-(ethylamino)-5-(hydroxymethyl)-5,6,7,7a-tetrahydro-3aH-pyrano[3,2-d]thiazole-6,7-diol.

The following reactions, including without limitations schemes, conditions and compounds, are particularly preferred and included in the scope of the present invention. It shall be understood that the radicals $R^1$ to $R^3$ are not limited to be H, but any member of the respective Markush groups defining $R^1$ to $R^3$ can be applied instead of H. The other radicals have the meaning as defined above.

Scheme 1: Reaction sequence for compounds of sub-formula (IA-1)

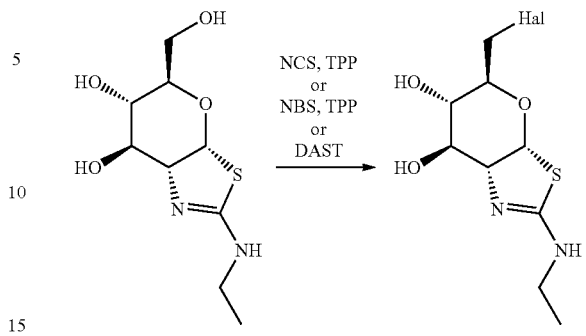

Compounds of sub-formula (IA-1) could be synthesized as depicted in Scheme 1. The primary alcohol of (3aR,5R,6S,7R,7aR)-2-(ethylamino)-5-(hydroxymethyl)-5,6,7,7a-tetrahydro-3aH-pyrano[3,2-d]thiazole-6,7-diol (Carbosynth catalog #MD08856) reacted selectively with a mixture of triphenylphosphine and N-halosuccinimide (either NCS or NBS) in DMF to give the corresponding halogenated analog. The fluorinated analog was synthesized by treating (3aR,5R,6S,7R,7aR)-2-(ethylamino)-5-(hydroxymethyl)-5,6,7,7a-tetrahydro-3aH-pyrano[3,2-d]thiazole-6,7-diol with DAST in dichloromethane.

Scheme 2: Reaction sequence for compounds of sub-formula (IA-2)

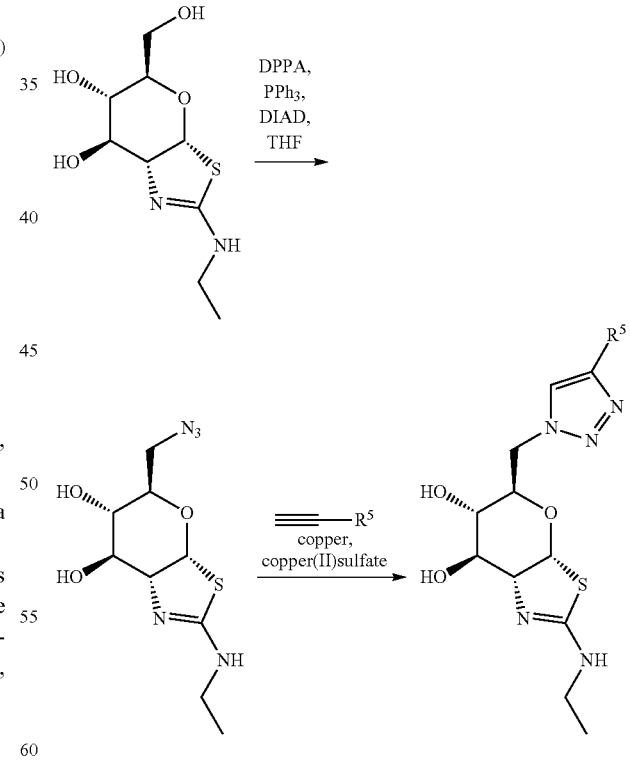

Compounds of sub-formula (IA-2) could be synthesized by the route depicted in Scheme 2 In the first step, azidation of (3aR,5R,6S,7R,7aR)-2-(ethylamino)-5-(hydroxymethyl)-5,6,7,7a-tetrahydro-3aH-pyrano[3,2-d]thiazole-6,7-diol using diphenylphosphoryl azide under Bose-Mitsunobu conditions afforded the primary azide, selectively (compound no. 1).

Subsequent treatment of the azide analog with various alkynes in the presence of copper catalysts afforded the triazole cycloaddition products.

Scheme 3: Reaction sequence for compounds of sub-formula (IB-1)

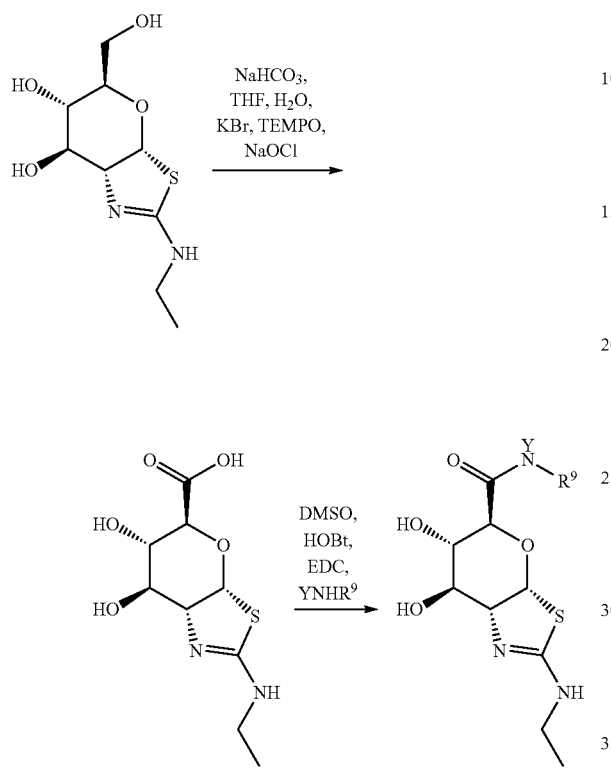

Compounds of sub-formula (IB-1) were synthesized according to the route outlined in Scheme 3. The amides were prepared in two steps: first, selective oxidation of the primary alcohol of (3aR,5R,6S,7R,7aR)-2-(ethylamino)-5-(hydroxymethyl)-5,6,7,7a-tetrahydro-3aH-pyrano[3,2-d]thiazole-6,7-diol to the carboxylic acid (compound no. 9; cf. e.g. EXAMPLE 48), then coupling to various amines using 1-hydroxybenzotriazole and a carbodiimide.

Scheme 4: Reaction sequence for compounds of sub-formula (IC)

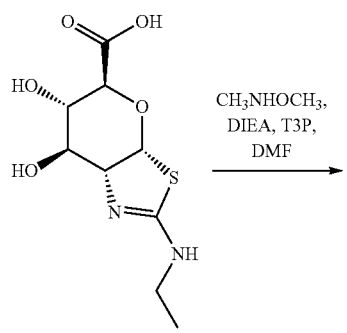

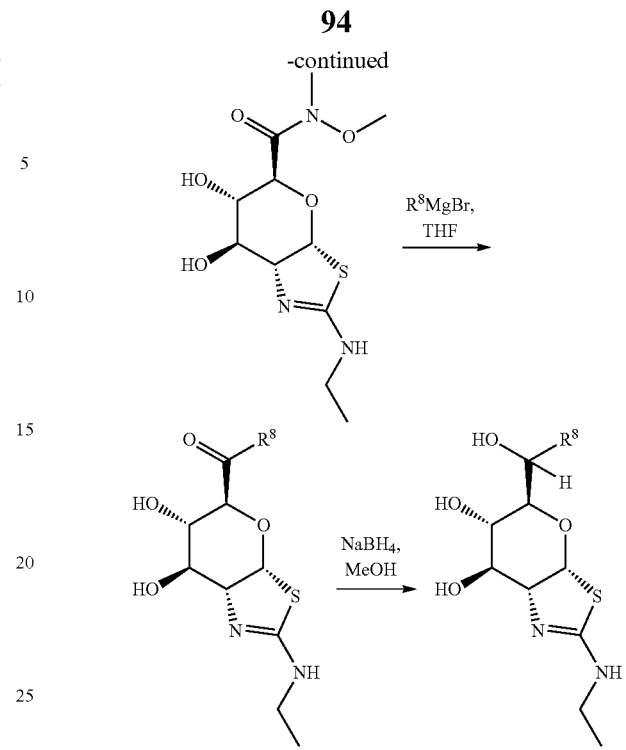

Compounds of sub-formula (IC) were prepared using the route depicted in Scheme 4. The C-6 carboxylic acid analog (compound no. 9; prepared as shown in Scheme 3) was converted to the corresponding Weinreb amide (compound no. 45) using N,O-dimethylhydroxylamine and propane phosphonic acid anhydride (T3P). Addition of Grignard reagents to the Weinreb amide produced ketones that were subsequently reduced by sodium borohydride to generate compounds with secondary alcohols at C-6.

The compounds of formula (I) are accessible via the routes above. The starting materials, including the compounds of formula (II), are usually known to the skilled artisan, or they can be easily prepared by known methods. Accordingly, any compound of formula (II) can be purified, provided as intermediate product and used as starting material for the preparation of compounds of formula (I).

The compounds of formula (I) can be modified, like hydrogenated or metal-reduced, to remove the chlorine, or put into a substitution reaction, and/or to be transformed with an acid or base into a salt, preferably with a strong acid. Numerous papers and methods are available and useful for the one skilled in the art in respect for organic chemistry, chemical strategies and tactics, synthetic routes, protection of intermediates, cleavage and purification procedure, isolation and characterization. General chemical modifications are known to the one skilled in the art. Halogenation of aryls or hydroxy substitution by halogens of acids, alcohols, phenols, and their tautomeric structures can be preferably carried out by use of $POCl_3$, or $SOCl_2$, $PCl_5$, $SO_2Cl_2$. In some instances oxalyl chloride is also useful. Temperatures can vary from 0° C. to reflux depending on the task to halogenate a pyridone structure or a carboxylic acid or a sulfonic acid. Time will also be adjusted from minutes to several hours or even over night. Similarly, alkylation, ether formation, ester formation, amide formation are known to the one skilled in the art. Arylation with aryl boronic acids can be performed in presence of a Pd catalyst, appropriate ligand and base, preferably a carbonate, phosphate, borate salt of sodium, potassium or cesium.

Organic bases, like Et₃N, DIPEA or the more basic DBU can also be used. Solvents can vary too, from toluene, dioxane, THF, diglyme, monoglyme, alcohols, DMF, DMA, NMP, acetonitrile, in some cases even water, and others. Commonly used catalysts like Pd (PPh$_3$)$_4$, or Pd(OAc)$_2$, PdCl$_2$ type precursors of PdO catalysts have advanced to more complex ones with more efficient ligands. In C—C arylations, instead of boronic acids and esters, aryl-trifluoroborate potassium salts (Suzuki-Miyaura coupling), organo silanes (Hiyama coupling), Grignard reagents (Kumada), organozinc compounds (Negishi coupling) and stannanes (Stille coupling) may be useful. This experience can be transferred to N- and O-arylations. Numerous papers and methods are available and useful for the one skilled in the art in respect of N-arylation and even of electron deficient anilines (Biscoe et al. JACS 130: 6686 (2008)), and with aryl chlorides and anilines (Fors et al. JACS 130: 13552 (2008)) as well as for O-arylation by using Cu catalysis and Pd catalysis.

In the final step of the processes above, a salt of the compounds according to formulae (I) to (II), preferably formula (I), is optionally provided. The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds according to the invention are for the most part prepared by conventional methods. If the compound according to the invention contains a carboxyl group, one of its suitable salts can be formed by the reaction of the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminum salts of the compounds according to the invention are likewise included. In the case of certain compounds according to the invention, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds according to the invention include the following: acetate, adipate, alginate, arginate, aspartate, benzoate, benzenesulfonate (besylate), bisulfate, bisulfite, bromide, butyrate, camphorate, camphorsulfonate, caprylate, chloride, chlorobenzoate, citrate, cyclopentanepropionate, digluconate, dihydrogenphosphate, dinitrobenzoate, dodecylsulfate, ethanesulfonate, fumarate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, isobutyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

With regard to that stated above, it can be seen that the expressions "pharmaceutically acceptable salt" and "physiologically acceptable salt", which are used interchangeable herein, in the present connection are taken to mean an active ingredient which comprises a compound according to the invention in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Object of the present invention is also the use of compounds according to formula (I) and/or physiologically acceptable salts thereof for inhibiting a glycosidase. The term "inhibition" denotes any reduction in glycosidase activity, which is based on the action of the specific inventive compounds capable to interact with the target glycosidase in such a manner that makes recognition, binding and blocking possible. The compounds are characterized by such an appreciable affinity to at least one glycoside hydrolase which ensures a reliable binding and preferably a complete blocking of glycosidase activity. More preferably, the substances are mono-specific in order to guarantee an exclusive and directed recognition with the chosen single glycosidase target. In the context of the present invention, the term "recognition"—without being limited thereto—relates to any type of interaction between the specific compounds and the target, particularly covalent or non-covalent binding or association, such as a covalent bond, hydrophobic/hydrophilic interactions, van der Waals forces, ion pairs, hydrogen bonds, ligand-receptor interactions, and the like. Such association may also encompass the presence of other molecules such as peptides, proteins or nucleotide sequences. The present receptor/ligand-interaction is preferably characterized by high affinity, high selectivity and minimal or even lacking cross-reactivity to other target molecules to exclude unhealthy and harmful impacts to the treated subject.

In a preferred embodiment of the present invention, the glycosidase comprises glycoside hydrolases, more preferably family 84 glycoside hydrolases, most preferably O-glycoprotein-2-acetamido-2deoxy-β-D-glucopyranosidase (OGA), highly preferably a mammalian O-GlcNAcase. It is particularly preferred that the compounds of formula (I) according to the invention selectively bind an O-GlcNAcase, e.g. thereby selectively inhibiting the cleavage of 2-acetamido-2-deoxy-β-D-glucopyranoside (O-GlcNAc) while they do not substantially inhibit a lysosomal β-hexosaminidase.

The compounds according to the invention preferably exhibit an advantageous biological activity, which is easily demonstrated in enzyme activity assays as described herein or known from prior art. In such in-vitro assays, the compounds preferably exhibit and cause an inhibitory effect. IC$_{50}$ is the concentration of a compound that produces 50% of the maximal inhibition for that compound. The glycosidase target is especially half inhibited by the compounds described herein if the concentration of the compounds amounts to 1 μM or less, preferably 0.5 μM or less, more preferably 0.2 μM or less, most preferably less than 0.1 μM.

The advantageous biological activity of the compounds according to the invention can also be demonstrated in cell-culture based assays, for example assays as described in WO 2008/025170, which is incorporated herein by reference. When testing compounds described herein in a cellular assay, an increase in O-GlcNAcylation (due to the inhibition of OGA) is measured. $EC_{50}$ is the effective concentration of a compound that produces 50% of the maximum possible response for that compound. The compounds of the invention exhibit $EC_{50}$ values in the range of 10 nM to 25 µM. It is preferred that the compounds of the invention have an activity, as expressed by an $EC_{50}$ standard, of 1 µM or less, preferably 0.5 µM or less, more preferably 0.2 µM or less, most preferably less than 0.1 µM.

A preferred object of the present invention relates to a method for inhibiting a glycosidase, wherein a cell capable of expressing, or expressing, the glycosidase is contacted with at least one compound of formula (I) according to the invention and/or physiologically acceptable salts thereof under conditions such that the glycosidase is inhibited. The prior teaching of the present specification concerning the compounds of formula (I), including any preferred embodiment thereof, is valid and applicable without restrictions to the compounds according to formula (I) and their salts when used in the method for inhibiting a glycosidase.

As discussed herein, the glycosidase-signaling pathways are relevant for various diseases, preferably neurodegenerative diseases, diabetes, cancer and stress. Accordingly, the compounds according to the invention are useful in the prophylaxis and/or treatment of diseases that are dependent on the said signaling pathways by interaction with one or more of them. The present invention therefore relates to compounds according to the invention as inhibitors of the signaling pathways described herein, preferably of the OGA-mediated signaling.

The method of the invention can be performed either in-vitro or in-vivo. The susceptibility of a particular cell to treatment with the compounds according to the invention can be particularly determined by in-vitro tests, whether in the course of research or clinical application. Typically, a culture of the cell is combined with a compound according to the invention at various concentrations for a period of time which is sufficient to allow the active agents to modulate glycosidase activity, usually between about one hour and one week. In-vitro treatment can be carried out using cultivated cells from any sample or cell line.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

For identification of a signal transduction pathway and for detection of interactions between various signal transduction pathways, various scientists have developed suitable models or model systems, for example cell culture models and models of transgenic animals. For the determination of certain stages in the signal transduction cascade, interacting compounds can be utilized in order to modulate the signal. The compounds according to the invention can also be used as reagents for testing OGA-dependent signal transduction pathways in animals and/or cell culture models or in the clinical diseases mentioned in this application.

The use according to the previous paragraphs of the specification may be either performed in-vitro or in-vivo models. The inhibition can be monitored by the techniques described in the course of the present specification. The in-vitro use is preferably applied to samples of humans suffering from neurodegenerative diseases, diabetes, cancer and stress. Testing of several specific compounds and/or derivatives thereof makes the selection of that active ingredient possible that is best suited for the treatment of the human subject. The in-vivo dose rate of the chosen derivative is advantageously pre-adjusted to the glycosidase susceptibility and/or severity of disease of the respective subject with regard to the in-vitro data. Therefore, the therapeutic efficacy is remarkably enhanced. Moreover, the subsequent teaching of the present specification concerning the use of the compounds according to formula (I) and its derivatives for the production of a medicament for the prophylactic or therapeutic treatment and/or monitoring is considered as valid and applicable without restrictions to the use of the compound for the inhibition of glycosidase activity, preferably OGA activity, if expedient.

The invention furthermore relates to a medicament comprising at least one compound according to the invention and/or pharmaceutically usable derivatives, salts, solvates and stereoisomers thereof, including mixtures thereof in all ratios. Preferably, the invention relates to a medicament comprising at least one compound according to the invention and/or physiologically acceptable salts thereof.

A "medicament" in the meaning of the invention is any agent in the field of medicine, which comprises one or more compounds of formula (I) or preparations thereof (e.g. a pharmaceutical composition or pharmaceutical formulation) and can be used in prophylaxis, therapy, follow-up or after-care of patients who suffer from diseases, which are associated with OGA activity, in such a way that a pathogenic modification of their overall condition or of the condition of particular regions of the organism could establish at least temporarily.

Consequently, the invention also relates to a pharmaceutical composition comprising as active ingredient an effective amount of at least one compound of formula (I) according to the invention and/or physiologically acceptable salts thereof together with pharmaceutically tolerable adjuvants and/or excipients.

In the meaning of the invention, an "adjuvant" denotes every substance that enables, intensifies or modifies a specific response against the active ingredient of the invention if administered simultaneously, contemporarily or sequentially. Known adjuvants for injection solutions are, for example, aluminum compositions, such as aluminum hydroxide or aluminum phosphate, saponins, such as QS21, muramyldipeptide or muramyltripeptide, proteins, such as gamma-interferon or TNF, M59, squalen or polyols.

Furthermore, the active ingredient may be administered alone or in combination with other treatments. A synergistic effect may be achieved by using more than one compound in the pharmaceutical composition, i.e. the compound of formula (I) is combined with at least another agent as active ingredient, which is either another compound of formula (I) or a compound of different structural scaffold. The active ingredients can be used either simultaneously or sequentially. The present compounds are suitable for combination with agents known to those of skill in the art (cf. e.g. WO 2008/025170, which is incorporated herein by reference) and are useful with the compounds of the present invention.

The invention also relates to a set (kit) consisting of separate packs of an effective amount of a compound according to the invention and/or pharmaceutically acceptable salts, derivatives, solvates and stereoisomers thereof, including mixtures thereof in all ratios, and an effective amount of a further medicament active ingredient. The set comprises suitable containers, such as boxes, individual bottles, bags or ampoules. The set may, for example, comprise separate ampoules, each containing an effective amount of a compound according to the invention and/or pharmaceutically acceptable salts, derivatives, solvates and stereoisomers thereof, including mixtures thereof in all ratios, and an effective amount of a further medicament active ingredient in dissolved or lyophilized form.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

The pharmaceutical composition of the invention is produced in a known way using common solid or liquid carriers, diluents and/or additives and usual adjuvants for pharmaceutical engineering and with an appropriate dosage. The amount of excipient material that is combined with the active ingredient to produce a single dosage form varies depending upon the host treated and the particular mode of administration. Suitable excipients include organic or inorganic substances that are suitable for the different routes of administration, such as enteral (e.g. oral), parenteral or topical application, and which do not react with compounds of formula (I) or salts thereof. Examples of suitable excipients are water, vegetable oils, benzyl alcohols, alkylene glycols, polyethylene glycols, glycerol triacetate, gelatin, carbohydrates, e.g. lactose or starch, magnesium stearate, talc and petroleum jelly. Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilized) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavors.

In a preferred embodiment of the present invention, the pharmaceutical composition is adapted for oral administration. The preparations can be sterilized and/or can comprise auxiliaries, such as carrier proteins (e.g. serum albumin), lubricants, preservatives, stabilizers, fillers, chelating agents, antioxidants, solvents, bonding agents, suspending agents, wetting agents, emulsifiers, salts (for influencing the osmotic pressure), buffer substances, colorants, flavorings and one or more further active substances, for example one or more vitamins. Additives are well known in the art, and they are used in a variety of formulations.

Accordingly, the invention also relates to a pharmaceutical composition comprising as active ingredient an effective amount of at least one compound of formula (I) according to the invention and/or physiologically acceptable salts thereof together with pharmaceutically tolerable adjuvants for oral administration, optionally in combination with at least another active pharmaceutical ingredient. The prior teaching of the present specification concerning administration route and combination product, respectively, is valid and applicable without restrictions to the combination of both features if expedient.

The terms "effective amount" or "effective dose" or "dose" are interchangeably used herein and denote an amount of the pharmaceutical compound having a prophylactically or therapeutically relevant effect on a disease or pathological conditions, i.e. which causes in a tissue, system, animal or human a biological or medical response which is sought or desired, for example, by a researcher or physician. A "prophylactic effect" reduces the likelihood of developing a disease or even prevents the onset of a disease. A "therapeutically relevant effect" relieves to some extent one or more symptoms of a disease or returns to normality either partially or completely one or more physiological or biochemical parameters associated with or causative of the disease or pathological conditions. In addition, the expression "therapeutically effective amount" denotes an amount which, compared with a corresponding subject who has not received this amount, has the following consequence: improved treatment, healing, prevention or elimination of a disease, syndrome, condition, complaint, disorder or side-effects or also the reduction in the advance of a disease, complaint or disorder. The expression "therapeutically effective amount" also encompasses the amounts which are effective for increasing normal physiological function.

The respective dose or dosage range for administering the pharmaceutical composition according to the invention is sufficiently high in order to achieve the desired prophylactic or therapeutic effect of reducing symptoms of the aforementioned diseases. It will be understood that the specific dose level, frequency and period of administration to any particular human will depend upon a variety of factors including the activity of the specific compound employed, the age, body weight, general state of health, gender, diet, time and route of administration, rate of excretion, drug combination and the severity of the particular disease to which the specific therapy is applied. Using well-known means and methods, the exact dose can be determined by one of skill in the art as a matter of routine experimentation. The prior teaching of the present specification is valid and applicable without restrictions to the pharmaceutical composition comprising the compounds of formula (I) if expedient.

Pharmaceutical formulations can be administered in the form of dosage units which comprise a predetermined amount of active ingredient per dosage unit. The concentration of the prophylactically or therapeutically active ingredient in the formulation may vary from about 0.1 to 100 wt %. Preferably, the compound of formula (I) or the pharmaceutically acceptable salts thereof are administered in doses of approximately 0.5 to 1000 mg, more preferably between 1 and 700 mg, most preferably 5 and 100 mg per dose unit. Generally, such a dose range is appropriate for total daily incorporation. In other terms, the daily dose is preferably between approximately 0.02 and 100 mg/kg of body weight. The specific dose for each patient depends, however, on a wide variety of factors as already described in the present specification (e.g. depending on the condition treated, the method of administration and the age, weight and condition of the patient). Preferred dosage unit formulations are those which comprise a daily dose or part-dose, as indicated above, or a corresponding fraction thereof of an active ingredient. Furthermore, pharmaceutical formulations of this type can be prepared using a process which is generally known in the pharmaceutical art.

Although a therapeutically effective amount of a compound according to the invention has to be ultimately determined by the treating doctor or vet by considering a number of factors (e.g. the age and weight of the animal, the precise condition that requires treatment, severity of condition, the nature of the formulation and the method of administration), an effective amount of a compound according to the invention for the treatment of neurodegenerative diseases, for example Alzheimer's disease, is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

The pharmaceutical composition of the invention can be employed as medicament in human and veterinary medicine. According to the invention, the compounds of formula (I) and/or physiologically salts thereof are suited for the prophylactic or therapeutic treatment and/or monitoring of diseases that are caused, mediated and/or propagated by OGA activity. It is particularly preferred that the diseases are neurodegenerative diseases, diabetes, cancer and stress, more preferably neurodegenerative diseases, most preferably tauopathies, highly preferably Alzheimer's disease. It shall be understood that the host of the compound is included in the present scope of protection according to the present invention.

The neurodegenerative disease or condition is more preferably selected from the group of Alzheimer's disease, Amyotrophic lateral sclerosis (ALS), Amyotrophic lateral sclerosis with cognitive impairment (ALSci), Argyrophilic grain dementia, Bluit disease, Corticobasal degeneration (CBP), Dementia pugilistica, Diffuse neurofibrillary tangles with calcification, Down's syndrome, Familial British dementia, Familial Danish dementia, Frontotemporal dementia with parkinsonism linked to chromosome 17 (FTDP-17), Gerstmann-Straussler-Scheinker disease, Guadeloupean parkinsonism, Hallevorden-Spatz disease (neurodegeneration with brain iron accumulation type 1), Multiple system atrophy, Myotonic dystrophy, Niemann-Pick disease (type C), Pallido-ponto-nigral degeneration, Parkinsonism-dementia complex of Guam, Pick's disease (PiD), Postencephalitic parkinsonism (PEP), Prion diseases (including Creutzfeldt-Jakob Disease (GJD), Variant Creutzfeldt-Jakob Disease (vCJD), Fatal Familial Insomnia, Kuru, Progressive supercortical gliosis, Progressive supranuclear palsy (PSP), Richardson's syndrome, Subacute sclerosing panencephalitis, Tangle-only dementia, Huntington's disease and Parkinson's disease. Most preferred is Alzheimer's disease.

The invention also relates to the use of compounds according to formula (I) and/or physiologically acceptable salts thereof for the prophylactic or therapeutic treatment and/or monitoring of diseases that are caused, mediated and/or propagated by OGA activity. Furthermore, the invention relates to the use of compounds according to formula (I) and/or physiologically acceptable salts thereof for the production of a medicament for the prophylactic or therapeutic treatment and/or monitoring of diseases that are caused, mediated and/or propagated by OGA activity. Compounds of formula (I) and/or a physiologically acceptable salt thereof can furthermore be employed as intermediate for the preparation of further medicament active ingredients. The medicament is preferably prepared in a non-chemical manner, e.g. by combining the active ingredient with at least one solid, fluid and/or semi-fluid carrier or excipient, and optionally in conjunction with a single or more other active substances in an appropriate dosage form.

Another object of the present invention are compounds of formula (I) according to the invention and/or physiologically acceptable salts thereof for use in the prophylactic or therapeutic treatment and/or monitoring of diseases that are caused, mediated and/or propagated by OGA activity. Another preferred object of the invention concerns compounds of formula (I) according to the invention and/or physiologically acceptable salts thereof for use in the prophylactic or therapeutic treatment and/or monitoring of neurodegenerative diseases, diabetes, cancer and stress. The prior teaching of the present specification concerning the compounds of formula (I), including any preferred embodiment thereof, is valid and applicable without restrictions to the compounds according to formula (I) and their salts for use in the prophylactic or therapeutic treatment and/or monitoring of neurodegenerative diseases, diabetes, cancer and stress.

The compounds of formula (I) according to the invention can be administered before or following an onset of disease once or several times acting as therapy. The aforementioned compounds and medical products of the inventive use are particularly used for the therapeutic treatment. A therapeutically relevant effect relieves to some extent one or more symptoms of a disorder, or returns to normality, either partially or completely, one or more physiological or biochemical parameters associated with or causative of a disease or pathological condition. Monitoring is considered as a kind of treatment provided that the compounds are administered in distinct intervals, e.g. in order to booster the response and eradicate the pathogens and/or symptoms of the disease completely. Either the identical compound or different compounds can be applied. The medicament can also be used to reducing the likelihood of developing a disorder or even prevent the initiation of disorders associated with OGA activity in advance or to treat the arising and continuing symptoms. The disorders as concerned by the invention are preferably neurodegenerative diseases, diabetes, cancer and stress.

In the meaning of the invention, prophylactic treatment is advisable if the subject possesses any preconditions for the aforementioned physiological or pathological conditions, such as a familial disposition, a genetic defect, or a previously passed disease.

It is another object of the invention to provide a method for treating diseases that are caused, mediated and/or propagated by OGA activity, wherein an effective amount of at least one compound of formula (I) according to the invention and/or physiologically acceptable salts thereof is administered to a mammal in need of such treatment. It is another preferred object of the invention to provide a method for treating neurodegenerative diseases, diabetes, cancer and stress, preferably a tauopathy, wherein an effective amount of at least one compound of formula (I) according to the invention and/or physiologically acceptable salts thereof is administered to a mammal in need of such treatment. The preferred treatment is an oral administration. The prior teaching of the invention and its embodiments is valid and applicable without restrictions to the methods of treatment if expedient.

In the scope of the present invention, compounds of formula (I) are provided for the first time. The low molecular weight compounds of the invention are strong and selective glycosidase inhibitors with improved passive permeability endowed by the more lipophilic moieties at C-6 position. O-GlcNAcylation of nuclear and cytoplasmic proteins is one of the most common post-translational modifications in animals and plants. O-GlcNAc cycling modulates a number of cellular processes, and evidence is mounting that dysregulation of O-GlcNAcylation plays a role in the etiology of several diseases, including Alzheimer's disease. O-GlcNAc transferase (OGT) and O-GlcNAcase (OGA) are the two enzymes that regulate O-GlcNAc cycling. Emerging data suggest that inhibitors that block OGA may help maintain healthy O-GlcNAc levels in Alzheimer's disease patients and thereby inhibit the formation of neurofibrillary tangles. Hence, the current invention comprises the use of compounds of formula (I) in the regulation, modulation and/or inhibition of the glycosidase signal cascade, which can be advantageously applied as research tool, for diagnosis and/or in treatment of any disorders that are responsive to OGA signaling and inhibition.

The low molecular weight inhibitors can be applied either themselves and/or in combination with physical measurements for diagnostics of treatment effectiveness. Medicaments and pharmaceutical compositions containing said compounds and the use of said compounds to treat glycosidase-mediated conditions is a promising, novel approach for a broad spectrum of therapies causing a direct and immediate improvement in the state of health, whether in man and animal. The impact is of special benefit to efficiently combat Alzheimer's disease, either alone or in combination with other neurodegenerative treatments.

Due to the surprisingly appreciable inhibitory activity on OGA, along with passive permeability, the compounds of the invention can be advantageously administered at lower doses compared to other less potent or selective inhibitors of prior art while still achieving equivalent or even superior desired biological effects. In addition, such a dose reduction advantageously leads to less or even no medicinal adverse effects.

The compounds of formula (I), their salts, isomers, tautomers, enantiomeric forms, diastereomers, racemates, derivatives, prodrugs and/or metabolites are characterized by a high specificity and stability, low manufacturing costs and convenient handling. These features form the basis for a reproducible action, wherein the lack of cross-reactivity is included, and for a reliable and safe interaction with the target structure.

All the references cited herein are incorporated by reference in the disclosure of the invention hereby.

It is to be understood that this invention is not limited to the particular compounds, pharmaceutical compositions, uses and methods described herein, as such matter can, of course, vary. It is also to be understood that the terminology used herein is for the purpose of describing particular embodiments only and is not intended to limit the scope of the present invention, which is only defined by the appended claims. As used herein, including the appended claims, singular forms of words such as "a," "an," and "the" include their corresponding plural referents unless the context clearly dictates otherwise. Thus, e.g., reference to "a compound" includes a single or several different compounds, and reference to "a method" includes reference to equivalent steps and methods known to a person of ordinary skill in the art, and so forth. Unless otherwise defined, all technical and scientific terms used herein have the same meaning as commonly understood by a person of ordinary skill in the art to which this invention belongs.

The techniques that are essential according to the invention are described in detail in the specification. Other techniques which are not described in detail correspond to known standard methods that are well known to a person skilled in the art, or the techniques are described in more detail in cited references, patent applications or standard literature. Although methods and materials similar or equivalent to those described herein can be used in the practice or testing of the present invention, suitable examples are described below. The following examples are provided by way of illustration and not by way of limitation. Within the examples, standard reagents and buffers that are free from contaminating activities (whenever practical) are used. The examples are particularly to be construed such that they are not limited to the explicitly demonstrated combinations of features, but the exemplified features may be unrestrictedly combined again if the technical problem of the invention is solved. Similarly, the features of any claim can be combined with the features of one or more other claims.

In the following examples, "conventional workup" means: water was added if necessary, the pH was adjusted, if necessary, to a value of between 2 and 10, depending on the constitution of the end product, the mixture was extracted with ethyl acetate or dichloromethane, the phases were separated, the organic phase was dried over sodium sulfate and evaporated, and the product was purified by chromatography on silica gel and/or by crystallization. $R_f$ values were determined on silica gel. The eluent was ethyl acetate/methanol 9:1.

LCMS and HPLC analysis as well as H NMR were performed as follows:
LCMS-Analysis:
Method A: A—0.1% TFA in $H_2O$, B—0.1% TFA in ACN: Flow—0.8 mL/min.
Gradient: 5-95% B in 3.5 min; Wavelength: 254 nm; Mass Scan: 100-900 Da.
Column: XBridge C8 (50×4.6 mm, 5 μm).
Method B: A—10 mM $NH_4HCO_3$ in $H_2O$, B—ACN; Flow—1.0 mL/min.
Column: XBridge C8 (50×4.6 mm, 3.5 μm).
HPLC:—Analysis:
Method A: A—0.1% TFA in $H_2O$, B—0.1% TFA in ACN: Flow—2.0 mL/min.
Column: XBridge C8 (50×4.6 mm, 3.5 μm).
Method B: A—10 mM $NH_4HCO_3$ in $H_2O$, B—ACN; Flow—1.0 mL/min.
Column: XBridge C8 (50×4.6 mm, 3.5 μm).
RT: retention time
$^1$H NMR was recorded on a Jeol 400 MHz or a Varian 500 MHz spectrometer, using residual signal of deuterated solvent as internal reference. Chemical shifts (δ) are reported in ppm relative to the residual solvent signal (δ=2.49 ppm for $^1$H NMR in DMSO-d6). $^1$H NMR data are reported as follows: chemical shift (multiplicity, coupling constants, and number of hydrogens). Multiplicity is abbreviated as follows: s (singlet), d (doublet), t (triplet), q (quartet), m (multiplet), br (broad).

EXAMPLE 1

(3aR,5R,6S,7R,7aR)-2-(ethylamino)-5-[(4-pyridin-2-yl-1H-1,2,3-triazol-1-yl)methyl]-5,6,7,7a-tetrahydro-3aH-pyrano[3,2-d][1,3]thiazole-6,7-diol (compound no. 7)

In a 5 mL seal vial equipped with a stir bar, a septum was added (3aR,5R,6S,7R,7aR)-5-(azidomethyl)-2-(ethylamino)-5,6,7,7a-tetrahydro-3aH-pyrano[3,2-d][1,3]thiazole-6,7-diol (40.00 mg; 0.15 mmol; 1.00 eq.), copper Not supported by ACD (65.10 mg; 1.02 mmol; 7.00 eq.) and copper (2+) sulfate pentahydrate (7.31 mg; 0.03 mmol; 0.20 eq.). The vial was evacuated and filled with $N_2$. This procedure was repeated for twice before ethanol (0.40 ml)/water (0.60 ml)/2-methylpropan-2-ol (1.00 ml) and 2-ethynylpyridine (0.03 ml; 0.29 mmol; 2.00 eq.) was added into the mixture. The mixture was stirred at room temperature for overnight before 3 mL $H_2O$ was added into the mixture and dried via lyophilization. The mixture was purified with Yamazen C1 acidic condition affording 14.4 mg (20.1%) of the title compound as a white solid (HPLC 99%, retention time=1.73 min) once lyophilized.

$^1$H NMR (DMSO-d6) δ 8.60 (m, 1H), 8.44 (s, 1H), 8.03 (d, J=8.0 Hz, 1H), 7.90 (ddd, J=7.6, 7.6, 1.6 Hz, 1H), 7.35 (m, 1H), 6.21 (d, J=1.6 Hz, 1H), 5.35 (bs, 1H), 5.27 (bs, 1H), 4.76 (dd, J=14.4, 2.4 Hz, 1H), 4.54 (dd, J=14.4, 8.4 Hz, 1H), 4.01 (dd, J=1.6, 1.6 Hz, 1H), 3.86 (dt, J=4.8, 4.8 Hz, 1H), 3.75 (m, 1H), 3.39 (m, 1H), 3.14 (q, J=6.8 Hz, 2H), 1.05 (t, J=7.2 Hz, 3H);

MS (m/z): 377 $[M+H]^+$.

EXAMPLE 2

(3aR,5R,6S,7R,7aR)-2-(ethylamino)-5-[(4-phenyl-1H-1,2,3-triazol-1-yl)methyl]-5,6,7,7a-tetrahydro-3aH-pyrano[3,2-d][1,3]thiazole-6,7-diol (compound no. 2)

The title compound was prepared with the above method using ethynylbenzene (0.01 ml; 0.11 mmol; 1.50 eq.). The mixture was purified with Yamazen Channel 2 (neutral condition) to afford 8.4 mg (31%) of the title compound as a white solid once lyophilized. $^1$H NMR (DMSO-d6) δ 8.30 (s, 1H), 7.75 (d, J=7.2 Hz, 2H), 7.48 (dd, J=7.2, 7.2 Hz, 2H), 7.41 (dd, J=7, 6, 7.6 Hz, 1H), 6.21 (d, J=6.0 Hz, 1H), 4.63 (dd, J=14.8, 8.0 Hz, 1H), 4.17 (dd, J=6.0, 6.0 Hz, 1H), 4.05 (dd, J=4.8, 4.8 Hz, 1H), 3.92 (dd, J=6.8, 6.8 Hz, 1H), 3.54 (dd, J=9.6, 4.8 Hz, 1H), 3.20 (m, 2H), 1.09 (t, J=8.8 Hz, 3H);

MS (m/z): 376 $[M+H]^+$.

EXAMPLE 3

(3aR,5R,6S,7R,7aR)-5-[(4-benzyl-1H-1,2,3-triazol-1-yl)methyl]-2-(ethylamino)-5,6,7,7a-tetrahydro-3aH-pyrano[3,2-d][1,3]thiazole-6,7-diol (compound no. 14)

The title compound was prepared with the above method using prop-2-yn-1-ylbenzene (0.03 ml; 0.27 mmol; 2.00 eq.). The mixture was purified with was purified via Waters pre-HPLC (flow rate 40 mL/min, desired product efflux at $H_2O$/ACN=64/36) to afford 26.3 mg (39%) of the title compound as a white solid once lyophilized.

$^1$H NMR (D$_2$O) δ 7.82 (s, 1H), 7.25-7.40 (m, 5H), 6.47 (d, J=6.8 Hz, 1H), 4.63 (dd, J=12.4, 4.4 Hz, 1H), 4.20 (dd, J=6.8, 6.8 Hz, 1H), 4.06 (s, 2H), 4.01 (m, 2H), 3.47 (dd, J=9.6, 6.8 Hz, 1H), 3.37 (qd, J=7.2, 2.4 Hz, 2H), 1.21 (t, J=6.8 Hz, 3H);

MS (m/z): 390 $[M+H]^+$.

EXAMPLE 4

(3aR,5R,6S,7R,7aR)-2-(ethylamino)-5-{[4-(2-phenylethyl)-1H-1,2,3-triazol-1-yl]methyl}-5,6,7,7a-tetrahydro-3aH-pyrano[3,2-d][1,3]thiazole-6,7-diol (compound no. 6)

The title compound was prepared with the above method using but-3-yn-1-ylbenzene (0.03 ml; 0.22 mmol; 1.50 eq.).

The mixture was purified with Yamazen Channel 1 (neutral condition, 35 g Interchim C18 column, flow rate 30 mL/min, desired product showed up at $H_2O$/ACN=60/40) to give 35.3 mg (47%) of the title compound as a white solid once lyophilized.

$^1$H NMR (D$_2$O) δ 7.42 (s, 1H), 7.01-7.22 (m, 4H), 6.05 (d, J=4.8 Hz, 1H), 4.53 (m, 1H), 4.36 (dd, J=12.4, 12.0 Hz, 1H), 4.01 (dd, J=4.8, 4.8 Hz, 1H), 3.91 (dd, J=4.0, 4.0 Hz, 1H), 3.69 (m, 1H), 3.32 (dd, J=6.8, 3.6 Hz, 1H), 3.09 (m, 2H), 2.90 (m, 2H), 2.85 (m, 2H), 1.00 (t, J=5.6 Hz, 3H);

MS (m/z): 404 $[M+H]^+$.

EXAMPLE 5

(3aR,5R,6S,7R,7aR)-2-(ethylamino)-5-{[4-(3-phenylpropyl)-1H-1,2,3-triazol-1-yl]methyl}-5,6,7,7a-tetrahydro-3aH-pyrano[3,2-d][1,3]thiazole-6,7-diol (compound no. 30)

The title compound was prepared with the above method using pent-4-yn-1-ylbenzene (120.2 μl; 0.787 mmol; 4.00 eq.). The mixture was purified with Waters pre-HPLC (flow rate 60 mL/min, desired product efflux at $H_2O$/ACN=53/47) to give 11.1 mg (11%) of the title compound as a white solid once lyophilized.

$^1$H NMR (MeOH-d4) δ 87.73 (s, 1H), 7.20-7.28 (m, 2H), 7.10-7.20 (m, 3H), 6.50 (d, J=6.8 Hz, 1H), 4.80 (dd, J=14.8, 7.2 Hz, 1H), 4.61 (dd, J=4.8, 4.8 Hz, 1H), 4.19 (dd, J=6.4 Hz, 1H), 3.99 (m, 1H), 3.94 (dd, J=4.0, 4.0 Hz, 1H), 3.41 (m, 3H), 2.70 (dd, J=7.6, 7.6 Hz, 2H), 2.64 (dd, J=7.6, 7.6 Hz, 2H), 1.97 (m, 2H), 1.26 (t, J=7.2 Hz, 3H);

MS (m/z): 417 $[M+H]^+$.

EXAMPLE 6

Methyl 1-{[(3aR,5R,6S,7R,7aR)-2-(ethylamino)-6,7-dihydroxy-5,6,7,7a-tetrahydro-3aH-pyrano[3,2-d][1,3]thiazol-5-yl]methyl}-1H-1,2,3-triazole-4-carboxylate (compound no. 10)

The title compound was prepared with the above method using methyl propiolate (0.03 ml; 0.35 mmol; 2.00 eq.). The mixture was purified with Waters pre-HPLC to give 12.1 mg (15%) of the title compound as a white solid once lyophilized.

$^1$H NMR (D2O) δ 88.56 (s, 1H), 6.53 (d, J=6.8 Hz, 1H), 4.90 (m, 1H), 4.22 (dd, J=6.8, 6.8 Hz, 1H), 4.12 (m, 1H), 4.02 (dd, J=6.8, 6.8 Hz, 1H), 3.93 (s, 3H), 3.46 (dd, J=9.2, 6.4 Hz, 1H), 3.38 (m, 2H), 1.21 (t, J=7.2 Hz, 3H);

MS (m/z): 358 $[M+H]^+$.

EXAMPLE 7

(3aR,5R,6S,7R,7aR)-2-(ethylamino)-5-{[4-(methoxymethyl)-1H-1,2,3-triazol-1-yl]methyl}-5,6,7,7a-tetrahydro-3aH-pyrano[3,2-d][1,3]thiazole-6,7-diol (compound 11)

The title compound was prepared with the above method using 3-methoxyprop-1-yne (0.03 ml; 0.35 mmol; 2.00 eq.). The mixture was purified with Waters pre-HPLC to give 8.2 mg (10%) of the title compound as a white solid once lyophilized.

$^1$H NMR (D2O) δ 88.16 (bs, 1H), 6.49 (d, J=6.8 Hz, 1H), 4.55 (bs, 2H), 4.19 (dd, J=6.8, 6.8 Hz, 1H), 4.05 (m, 1H), 3.99 (dd, J=6.8, 6.8 Hz, 1H), 3.26-3.45 (m, 6H), 2.68 (s, 1H), 1.19 (t, J=7.2 Hz, 3H);

MS (m/z): 344 $[M+H]^+$.

EXAMPLE 8

(3aR,5R,6S,7R,7aR)-5-{[4-(1H-1,2,3-benzotriazol-1-ylmethyl)-1H-1,2,3-triazol-1-yl]methyl}-2-(ethylamino)-5,6,7,7a-tetrahydro-3aH-pyrano[3,2-d][1,3]thiazole-6,7-diol (compound no. 57)

The title compound was prepared with the above method using 1-prop-2-yn-1-yl-1H-1,2,3-benzotriazole (100.66 µl; 0.66 mmol; 3.00 eq.). The mixture was purified with Waters pre-HPLC to give 32.6 mg (27%) of the title compound as a light blue foam once lyophilized.

$^1$H NMR (MeOH-d4) δ 7.81-8.08 (m, 3H), 7.47 (dd, J=5.6, 5.6 Hz, 1H), 7.35 (bs, 1H), 6.41 (d, J=5.2 Hz, 1H), 5.95 (s, 2H), 4.55 (dd, J=11.6, 5.6 Hz, 1H), 4.07 (dd, J=5.2, 5.2 Hz, 1H), 3.88 (dd, J=6.8, 6.8 Hz, 1H), 3.81 (dd, J=4.8, 4.8 Hz, 1H), 3.33 (m, 3H), 1.16 (dd, J=6.0, 6.0 Hz, 1H);

MS (m/z): 431 [M+H]$^+$.

EXAMPLE 9

(3aR,5R,6S,7R,7aR)-2-(ethylamino)-5-{[4-(phenoxymethyl)-1H-1,2,3-triazol-1-yl]methyl}-5,6,7,7a-tetrahydro-3aH-pyrano[3,2-d][1,3]thiazole-6,7-diol (compound no. 58)

The title compound was prepared with the above method using (prop-2-yn-1-yloxy)benzene (112.81 µl; 0.88 mmol; 3.00 eq.). The mixture was purified with Waters pre-HPLC to give 33.1 mg (28%) of the title compound as a white foam once lyophilized.

$^1$H NMR (MeOH-d4) δ 7.95 (s, 1H), 7.18 (dd, J=6.0, 6.0 Hz, 2H), 6.90 (d, J=7.2 Hz, 2H), 6.86 (dd, J=6.4, 6.4 Hz, 1H), 6.44 (d, J=5.2 Hz, 1H), 5.06 (s, 2H), 4.59 (dd, J=11.6, 6.0 Hz, 1H), 4.08 (dd, J=5.2, 5.2 Hz, 1H), 3.93 (dd, J=7.2, 7.2 Hz, 1H), 3.83 (dd, J=5.2, 5.2 Hz, 1H), 3.31 (m, 3H), 1.17 (t, J=6.0 Hz, 3H);

MS (m/z): 406 [M+H]$^+$.

EXAMPLE 10

(3aR,5R,6S,7R,7aR)-5-(azidomethyl)-2-(ethylamino)-5,6,7,7a-tetrahydro-3aH-pyrano[3,2-d][1,3]thiazole-6,7-diol (compound no. 50)

The title compound was prepared with the above method using prop-2-yn-1-ylcyclohexane (127.16 µl; 0.88 mmol; 3.00 eq.). The mixture was purified with Waters pre-HPLC (product efflux at H$_2$O/ACN=53/47) to give 45.2 mg (39.0%) of the title compound as a white foam once lyophilized.

$^1$H NMR (MeOH-d4) δ 7.60 (s, 1H), 6.47 (d, J=5.2 Hz, 1H), 4.71 (dd, J=12.0, 2.0 Hz, 1H), 4.50 (dd, J=11.6, 6.0 Hz, 1H), 4.11 (dd, J=5.2, 5.2 Hz, 1H), 3.89 (ddd, J=2.0, 5.6, 5.6 Hz, 1H), 3.84 (dd, J=5.2, 5.2 Hz, 1H), 3.35 (m, 1H), 3.30 (m, 2H), 2.47 (d, J=5.6 Hz, 2H), 1.44-1.63 (m, 7H), 1.05-1.22 (m, 5H), 0.88 (m, 2H);

MS (m/z): 396 [M+H]$^+$.

EXAMPLE 11

(3aR,5S,6S,7R,7aR)-5-(chloromethyl)-2-(ethylamino)-5,6,7,7a-tetrahydro-3aH-pyrano[3,2-d][1,3]thiazole-6,7-diol (compound no. 32)

In a 5 mL seal vial equipped with a stir bar was added (3aR,5R,6S,7R,7aR)-2-(ethylamino)-5-(hydroxymethyl)-5,6,7,7a-tetrahydro-3aH-pyrano[3,2-d][1,3]thiazole-6,7-diol (30.00 mg; 0.12 mmol; 1.00 eq.) and 1-chloropyrrolidine-2,5-dione (24.20 mg; 0.18 mmol; 1.50 eq.) in N,N-dimethylformamide (1.00 ml) followed by triphenylphosphine (63.38 mg; 0.24 mmol; 2.00 eq.). After the clear solution was stirred at 50° C. for 2 h, color became wine red. The reaction was stirred for overnight before it is concentrated and dissolved in 2 mL MeOH. Yamazen HPLC Channel1 (acidic condition, 220 nm, 55 g Interchim column, product efflux at H$_2$O/ACN=75/25) was used to isolate 5.4 mg (12%) of the title compound as a white solid once lyophilized.

$^1$H NMR (D$_2$O) δ 6.60 (d, J=6.8 Hz, 1H), 4.27 (dd, J=6.8 Hz, 1H), 4.02 (dd, J=7.2 Hz, 2H), 3.90 (m, 2H), 3.75 (dd, J=7.6 Hz, 1H), 3.41 (m, 2H), 1.25 (t, J=7.6 Hz, 3H);

MS (m/z): 267 [M+H]$^+$.

EXAMPLE 12

(3aR,5S,6S,7R,7aR)-5-(bromomethyl)-2-(ethylamino)-5,6,7,7a-tetrahydro-3aH-pyrano[3,2-d][1,3]thiazole-6,7-diol (compound no. 5)

The title compound was prepared with the above method using 1-bromopyrrolidine-2,5-dione (69.89 mg; 0.39 mmol; 1.50 eq.). The mixture was purified by Yamazen C1 (acidic condition, 55 g C18 column from Interchim 30 µm, flow rate 20 mL/min, desired product efflux at (H$_2$O/ACN=65/35) to isolate 23.3 mg (27%) of the title compound as a white solid once lyophilized.

$^1$H NMR (D$_2$O) δ 6.56 (d, J=6.8 Hz, 1H), 4.24 (dd, J=6.8 Hz, 1H), 3.99 (dd, J=7.2 Hz, 1H), 3.92 (m, 1H), 3.74 (m, 1H), 3.70 (m, 2H), 3.38 (m, 2H), 1.21 (t, J=7.6 Hz, 3H);

MS (m/z): 312 [M+H]$^+$.

EXAMPLE 13

(3aR,5S,6S,7R,7aR)-2-(ethylamino)-6,7-dihydroxy-5,6,7,7a-tetrahydro-3aH-pyrano[3,2-d][1,3]thiazole-5-carbaldehyde (compound no. 47)

In a dry sealed vial was added (3aR,5S,6S,7R,7aR)-2-(ethylamino)-6,7-dihydroxy-N-methoxy-N-methyl-5,6,7,7a-tetrahydro-3aH-pyrano[3,2-d][1,3]thiazole-5-carboxamide (70.00 mg; 0.23 mmol; 1.00 eq.) in toluene (1.00 ml) and tetrahydrofuran (1.00 ml). The clear solution was cooled to −78° C. before hydrido(diisobutyl)aluminum (962.81 µl; 1.00 M; 0.96 mmol; 4.20 eq.) was added slowly. The obtained solution was stirred at −78° C. for 3 h before the reaction was quenched by addition of 1 mL H$_2$O at −78° C. The obtained mixture was stirred at this temperature for 5 min before it is warmed up to room temperature. The mixture was filtered and the obtained filtrated was dried with lyophilize to afford the title compound as white solid.

$^1$H NMR (D$_2$O) δ 6.19 (d, J=6.0 Hz, 1H), 5.02 (dd, J=3.0 Hz, 1H), 4.08 (dd, J=6.0 Hz, 1H), 3.92 (dd, J=4.5 Hz, 1H), 3.63 (dd, J=9.5, 5.0 Hz, 1H), 3.40 (m, 1H), 3.11 (m, 2H), 1.02 (t, J=6.5 Hz, 3H);

MS (m/z): 247 [M+H]$^+$; 265 [M+H+18]$^+$.

EXAMPLE 14

(3aR,5S,6S,7R,7aR)-2-[ethyl(methyl)amino]-6,7-dihydroxy-5,6,7,7a-tetrahydro-3aH-pyrano[3,2-d][1,3]thiazole-5-carboxylic acid (compound no. 36)

In a 5 mL sure seal vial was added (3aR,5S,6S,7R,7aR)-2-(ethylamino)-6,7-dihydroxy-5,6,7,7a-tetrahydro-3aH-pyrano[3,2-d][1,3]thiazole-5-carboxylic acid (53.00 mg; 0.20 mmol; 1.00 eq.) in N,N-dimethylformamide (2.00 ml) followed by dipotassium carbonate (55.85 mg; 0.40 mmol; 2.00 eq.) and iodomethane (29.69 µl; 0.40 mmol; 2.00 eq.). The mixture was stirred at room temperature for overnight before it was concentrated, purified by Yamazen C1 (40 g column, 220 nm) and dried with lyophilize to afford 7.3 mg (9.3%) monomethylated compound as white solid and two sets of peaks were found on NMR, ratio=3:1.

$^1$H NMR ($D_2O$) of major peak δ 6.41 (d, J=7.0 Hz, 1H), 5.48 (d, J=7.0 Hz, 1H), 4.30 (dd, J=6.0 Hz, 1H), 4.223 (dd, J=6.5 Hz, 1H), 4.08 (dd, J=6.5 Hz, 1H), 3.80 (s, 3H), 3.41 (m, 2H), 1.24 (t, J=9.0 Hz, 3H);

MS (m/z): 277 $[M+H]^+$.

EXAMPLE 16

Methyl-(3aR,5S,6S,7R,7aR)-2-[(tert-butoxycarbonyl)(ethyl)amino]-6,7-dihydroxy-5,6,7,7a-tetrahydro-3aH-pyrano[3,2-d][1,3]thiazole-5-carboxylate (compound no. 103)

In a dry sure-seal vial was added (3aR,5S,6S,7R,7aR)-2-(ethylamino)-6,7-dihydroxy-5,6,7,7a-tetrahydro-3aH-pyrano[3,2-d][1,3]thiazole-5-carboxylic acid (600.00 mg; 2.17 mmol; 1.00 eq.), di-tert-butyl dicarbonate (568.69 mg; 2.61 mmol; 1.20 eq.) and tBuOH (4.00 ml). The clear solution was stirred at room temperature overnight. The solution was concentrated, diluted with DCM, purified with 40 g Interchim HP column (30 µm). Only one peak was detected, efflux from EtOAc/Hex=55:45, ends at EtOAc/Hex=65:35. The collected solution was concentrated and lyophilized to afford 535.0 mg (66%) of the title compound as a mixture of a partially sticky white foam and white solid.

$^1$H NMR (DMSO) δ 6.01 (d, J=5.0 Hz, 1H), 4.20 (dd, J=4.5 Hz, 1H), 4.79 (dd, J=5.5 Hz, 1H), 4.00 (dd, J=5.5 Hz, 1H), 3.91-3.97 (m, 3H), 3.75 (s, 3H), 1.54 (s, 9H), 1.18 (t, J=7.0 Hz, 3H);

MS (m/z): 377 $[M+H]^+$.

EXAMPLE 17

(3aR,5R,6S,7R,7aR)-5-(azidomethyl)-2-(ethylamino)-5,6,7,7a-tetrahydro-3aH-pyrano[3,2-d][1,3]thiazole-6,7-diol (compound no. 1)

In a 2.5 mL seal vial equipped with a stir bar was added (3aR,5R,6S,7R,7aR)-2-(ethylamino)-5-(hydroxymethyl)-5,6,7,7a-tetrahydro-3aH-pyrano[3,2-d][1,3]thiazole-6,7-diol (150.00 mg; 0.60 mmol; 1.00 eq.) in tetrahydrofuran (2.00 ml) followed by triphenylphosphine (316.90 mg; 1.21 mmol; 2.00 eq.), isopropyl(Z)-(isopropoxyacetyl)diazenecarboxylate (0.25 ml; 1.21 mmol; 2.00 eq.). Diphenyl azidophosphate (0.26 ml; 1.21 mmol; 2.00 eq.) was then added dropwise in 15 min. During the addition, the former obtained green-yellow clear solution slowly turned to turbid and finally became clear again. The mixture was stirred at room temperature for 48 h. The mixture was purified via Yamazen channel 2 and lyophilized to provide 134.6 mg (81%) of the title compound as white solid.

$^1$H NMR (D2O) δ 6.27 (d, J=6.4 Hz, 1H), 4.18 (dd, J=6.4 Hz, 1H), 4.02 (dd, J=4.8 Hz, 1H), 3.71 (m, 1H), 3.56-3.64 (m, 2H), 3.49 (dd, J=13.6, 6.8 Hz, 1H), 3.21 (m, 2H), 1.11 (t, J=7.2 Hz, 3H);

MS (m/z): 289 $[M+H]^+$.

EXAMPLE 18

(2E)-N-[(3aR,5R,6S,7R,7aR)-6,7-dihydroxy-5-(hydroxymethyl)-5,6,7,7a-tetrahydro-3aH-pyrano[3,2-d][1,3]thiazol-2-yl]but-2-enamide (compound no. 19)

To a 10 mL reaction vial was added (3aR,5R,6S,7R,7aR)-5-[(acetyloxy)methyl]-2-[(2E)-but-2-enoylamino]-5,6,7,7a-tetrahydro-3aH-pyrano[3,2-d][1,3]thiazole-6,7-diyl diacetate (40.00 mg; 0.10 mmol; 1.00 eq.) in methanol (2.00 ml) followed by sodium methanolate (0.00 ml; 0.01 mmol; 0.10 eq.). The obtained clear solution was stirred at room temperature for 1 h. LCMS showed a strong peak of SM plus desired product and byproduct (m/z=331). After 5 h, LMCS only showed the product's peak. The solution was diluted with 10 mL MeOH before it was transferred into a 50 mL round-bottom flask. Half spoon resin (Dowex 50WX8) was added. The mixture was gently stirred for 10 sec before it was filtered. 30 mL MeOH was used to rinsed the cake. The obtained solution was concentrated and lyophilized to afford 90.6% of the title compound as a white solid.

$^1$H NMR (MeOH) δ 6.22 (d, J=6.8 Hz, 1H), 5.98 (s, 1H), 5.69 (d, J=0.8 Hz, 1H), 4.15 (dd, J=6.0 Hz, 1H), 4.06 (dd, J=6.0 Hz, 1H), 3.80-3.82 (m, 1H), 3.70 (dd, J=12.4, 6.0 Hz, 1H), 3.58 (m, 2H), 1.93 (s, 3H);

MS (m/z): 274 $[M+H]^+$.

EXAMPLE 19

(3aR,5R,6S,7R,7aR)-5-(aminomethyl)-2-(ethylamino)-5,6,7,7a-tetrahydro-3aH-pyrano[3,2-d][1,3]thiazole-6,7-diol (compound no. 61)

To (3aR,5R,6S,7R,7aR)-5-(azidomethyl)-2-(ethylamino)-5,6,7,7a-tetrahydro-3aH-pyrano[3,2-d][1,3]thiazole-6,7-diol (40.00 mg; 0.15 mmol; 1.00 eq.) in methanol (1.00 ml) was added acetic acid (10.00 µl). The mixture was passed through the H-cube instrument (20% $Pd(OH)_2$) cartridge, full $H_2$, at 40° C., continuously for 1 h. Mixture was concentrated. The desired material was isolated by flash column chromatography (KPNH column, 0 to 80% MeOH/DCM) to afford (3aR,5R,6S,7R,7aR)-5-(aminomethyl)-2-(ethylamino)-5,6,7,7a-tetrahydro-3aH-pyrano[3,2-d][1,3]thiazole-6,7-diol, (10.9 mg, 30%) as a white solid (once lyophilized).

$^1$H NMR (500 MHz, $CD_3OD$) δ 6.29 (d, J=6.4, 1H), 4.06 (t, J=6.1, 1H), 3.93 (t, J=5.4, 1H), 3.55 (ddd, J=9.2, 7.9, 3.0, 1H), 3.39 (dd, J=9.2, 5.1, 1H), 3.30-3.20 (m, 2H), 2.97 (dd, J=13.4, 3.0, 1H), 2.73 (dd, J=13.5, 7.6, 1H), 1.17 (t, J=7.2, 3H);

MS (m/z): 247; 248 $[M+H]^+$

EXAMPLE 20 tert-butyl [(3aR,5R,6S,7R,7aR)-2-(ethylamino)-6,7-dihydroxy-5,6,7,7a-tetrahydro-3aH-pyrano[3,2-d][1,3]thiazol-5-yl]methyl carbonate (compound no. 3)

To (3aR,5R,6S,7R,7aR)-2-(ethylamino)-5-(hydroxymethyl)-5,6,7,7a-tetrahydro-3aH-pyrano[3,2-d][1,3]thiazole-6,7-diol (50.00 mg; 0.20 mmol; 1.00 eq.) in THF (2.00 ml) and DMF (0.05 ml) under nitrogen was added di-tert-butyl dicarbonate (52.74 mg; 0.24 mmol; 1.20 eq.), 4-(dimethylamino)pyridine (4.92 mg; 0.04 mmol; 0.20 eq.) and triethylamine (0.03 ml; 0.24 mmol; 1.20 eq.). The reaction was stirred at room temperature for 24 h. Another 1 eq. of $Boc_2O$ and 0.2 eq. of DMAP were added and the reaction was stirred at room temperature overnight (total stirring time 40 h). The desired material was isolated by flash column chromatography (KPNH column, 0 to 20% MeOH/EtOAc) to afford tert-butyl [(3aR,5R,6S,7R,7aR)-2-(ethylamino)-6,7-dihydroxy-5,6,7,7a-tetrahydro-3aH-pyrano[3,2-d][1,3]thiazol-5-yl]methyl carbonate (5.30 mg, 8%) as a white solid (once lyophilized).

$^1$H NMR (500 MHz, CD$_3$OD) δ 6.23 (d, J=6.3, 1H), 4.28 (dd, J=11.7, 2.3, 1H), 4.16 (dd, J=11.8, 6.5, 1H), 4.06 (t, J=6.1, 1H), 3.93 (t, J=5.5, 1H), 3.75 (t, J=7.0, 1H), 3.48 (dd, J=9.5, 5.2, 1H), 3.29-3.20 (m, 2H), 1.46 (s, 9H), 1.16 (t, J=7.2, 3H);

MS (m/z): 348; 349 [M+H]$^+$.

EXAMPLE 21

(3aR,5S,6S,7R,7aR)-2-(ethylamino)-5-(fluoromethyl)-5,6,7,7a-tetrahydro-3aH-pyrano[3,2-d][1,3]thiazole-6,7-diol (compound no. 4)

To (3aR,5R,6S,7R,7aR)-2-(ethylamino)-5-(hydroxymethyl)-5,6,7,7a-tetrahydro-3aH-pyrano[3,2-d][1,3]thiazole-6,7-diol (100.00 mg; 0.40 mmol; 1.00 eq.) in DCM (3.00 ml) was added (diethylamino)sulfur trifluoride (0.08 ml; 0.60 mmol; 1.50 eq.). The reaction was stirred at room temperature for 2 h. The desired material was isolated by flash column chromatography (KPNH column, 0 to 15% MeOH/EtOAc 15CV). Product obtained, which was still not perfectly pure, was re-purified by flash column chromatography (KPNH column, 0 to 15% MeOH/EtOAc 15CV) again to afford (3aR,5S,6S,7R,7aR)-2-(ethylamino)-5-(fluoromethyl)-5,6,7,7a-tetrahydro-3aH-pyrano[3,2-d][1,3]thiazole-6,7-diol (6.03 mg, 6%) as a white solid (once lyophilized).

$^1$H NMR (500 MHz, CD$_3$OD) δ 6.26 (d, J=6.4, 1H), 4.59 (d, J=3.5, 1H), 4.49 (d, J=3.5, 1H), 4.06 (dd, J=11.2, 5.2, 1H), 3.97-3.86 (m, 1H), 3.78-3.67 (m, 1H), 3.51 (ddd, J=15.0, 9.3, 5.8, 1H), 3.29-3.16 (m, 2H), 1.20-1.12 (m, 3H);

MS (m/z): 250; 251 [M+H]$^+$.

EXAMPLE 22

(3aR,5R,6S,7R,7aR)-5-[(benzyloxy)methyl]-2-(ethylamino)-5,6,7,7a-tetrahydro-3aH-pyrano[3,2-d][1,3]thiazole-6,7-diol (compound no. 8)

To (3aR,4aR,8aS,9R,9aR)-2-(ethylamino)-7-phenyl-3a,4a,5,8a,9,9a-hexahydro[1,3]dioxino[4',5':5,6]pyrano[3,2-d][1,3]thiazol-9-ol (50.00 mg; 0.15 mmol; 1.00 eq.) in THF (1 mL) and molecular sieves (4 Å) was added sodium cyanoborohydride (37.36 mg; 0.59 mmol; 4.00 eq.) and the reaction was stirred at room temperature for 1 h. The reaction was then cooled to 0° C. and hydrogen chloride (0.37 ml; 2.00 M; 0.74 mmol; 5.00 eq.) was slowly added. Reaction was stirred at 0° C. for 15 min and then stirred at room temperature overnight. Reaction mixture was filtered through cellite, washed with DCM, concentrated, diluted again with DCM and washed with NaHCO$_3$. Organic layer was dried (Na$_2$SO$_4$), filtered, concentrated. The desired material was isolated by flash column chromatography (KPNH column) to afford (3aR,5R,6S,7R,7aR)-5-[(benzyloxy)methyl]-2-(ethylamino)-5,6,7,7a-tetrahydro-3aH-pyrano[3,2-d][1,3]thiazole-6,7-diol (12 mg, 24%) as a white solid (once lyophilized).

$^1$H NMR (500 MHz, cd$_3$od) δ 7.38-7.20 (m, 5H), 6.26 (d, J=6.4, 1H), 4.56 (s, 2H), 4.07 (t, J=6.0, 1H), 3.93 (t, J=5.4, 1H), 3.73 (d, J=9.9, 2H), 3.68-3.58 (m, 1H), 3.52 (dd, J=9.0, 5.3, 1H), 3.28-3.12 (m, 2H), 1.16 (t, J=7.2, 3H);

MS (m/z): 338; 339 [M+H]$^+$.

EXAMPLE 23

Tert-butyl [(3aR,5R,6S,7R,7aR)-6,7-dihydroxy-5-(hydroxymethyl)-5,6,7,7a-tetrahydro-3aH-pyrano[3,2-d][1,3]thiazol-2-yl]ethylcarbamate (compound no. 12)

To (3aR,5R,6S,7R,7aR)-2-(ethylamino)-5-(hydroxymethyl)-5,6,7,7a-tetrahydro-3aH-pyrano[3,2-d][1,3]thiazole-6,7-diol (100.00 mg; 0.40 mmol; 1.00 eq.), in tBuOH (2.00 ml) was added di-tert-butyl dicarbonate (105.47 mg; 0.48 mmol; 1.20 eq.). The reaction was stirred at room temperature overnight. The desired product was isolated by prep HPLC (0-15% B, 25 min, 220 nm, neutral conditions) to afford tert-butyl [(3aR,5R,6S,7R,7aR)-6,7-dihydroxy-5-(hydroxymethyl)-5,6,7,7a-tetrahydro-3aH-pyrano[3,2-d][1,3]thiazol-2-yl]ethylcarbamate (83.5 mg, 60%) as a white solid (once lyophilized).

$^1$H NMR (500 MHz, CD$_3$OD) δ 6.09 (d, J=7.3, 1H), 4.13 (s, 1H), 4.04 (s, 1H), 3.99-3.82 (m, 2H), 3.75 (d, J=11.6, 1H), 3.63 (m, 1H), 3.54 (m, 1H), 3.44 (m, 1H), 1.53 (s, 9H), 1.18 (t, J=6.9, 3H);

MS (m/z): 348; 349 [M+H]$^+$.

EXAMPLE 24

(3aR,5R,6S,7R,7aR)-2-(ethylamino)-5-(hydroxymethyl)-7-methoxy-5,6,7,7a-tetrahydro-3aH-pyrano[3,2-d][1,3]thiazol-6-ol (compound no. 15)

To tert-butyl ethyl[(3aR,4aR,8aS,9R,9aR)-9-methoxy-7-phenyl-3a,4a,5,8a,9,9a-hexahydro[1,3]dioxino[4',5':5,6]pyrano[3,2-d][1,3]thiazol-2-yl]carbamate (30.00 mg; 0.07 mmol; 1.00 eq.) in DCM (0.5 mL) was added trifluoroacetic acid (50.00 μl; 0.67 mmol; 10.11 eq.). Reaction stirred at room temperature overnight. The desired material was isolated by flash column chromatography (KPNH column, 10-20% EtOAc/MeOH) to afford (3aR,5R,6S,7R,7aR)-2-(ethylamino)-5-(hydroxymethyl)-7-methoxy-5,6,7,7a-tetrahydro-3aH-pyrano[3,2-d][1,3]thiazol-6-ol (13.7 mg, 78%) as a white solid (once lyophilized).

$^1$H NMR (500 MHz, CD$_3$OD) δ 6.21 (d, J=6.4, 1H), 4.18 (t, J=5.8, 1H), 3.77 (d, J=11.0, 1H), 3.66-3.54 (m, 4H), 3.54-3.49 (m, 3H), 3.29-3.17 (m, 2H), 1.16 (t, J=7.2, 3H);

MS (m/z): 262; 263 [M+H]$^+$.

EXAMPLE 25

(3aR,5R,6S,7R,7aR)—N-ethyl-6,7-dimethoxy-5-(methoxymethyl)-5,6,7,7a-tetrahydro-3aH-pyrano[3,2-d][1,3]thiazol-2-amine (compound no. 13)

To tert-butyl [(3aR,5R,6S,7R,7aR)-6,7-dimethoxy-5-(methoxymethyl)-5,6,7,7a-tetrahydro-3aH-pyrano[3,2-d][1,3]thiazol-2-yl]ethylcarbamate (22.30 mg; 0.06 mmol; 1.00 eq.) in DCM (0.5 mL) was added trifluoroacetic acid (10.00 μl; 0.13 mmol; 2.36 eq.) Reaction stirred at room temperature for 24 h. The desired material was isolated by flash column chromatography (KPNH column, 10-50% EtOAC/Hex) to afford (3aR,5R,6S,7R,7aR)—N-ethyl-6,7-dimethoxy-5-(methoxymethyl)-5,6,7,7a-tetrahydro-3aH-pyrano[3,2-d][1,3]thiazol-2-amine (13.1 mg, 79%) as a colorless oil (once lyophilized).

$^1$H NMR (500 MHz, CD$_3$OD) δ 6.13 (d, J=6.5, 1H), 4.38 (dd, J=5.3, 3.8, 1H), 3.86 (dd, J=3.3, 2.0, 1H), 3.58-3.51 (m, 2H), 3.50 (s, 3H), 3.47 (dd, J=11.0, 6.0, 2H), 3.43 (s, 3H), 3.35 (s, 3H), 3.30-3.16 (m, 2H), 1.16 (t, J=7.2, 3H);

MS (m/z): 290; 291 [M+H]$^+$.

EXAMPLE 26

Tert-butyl {(3aR,5R,6S,7R,7aR)-5-[(benzyloxy)methyl]-6,7-dihydroxy-5,6,7,7a-tetrahydro-3aH-pyrano[3,2-d][1,3]thiazol-2-yl}ethylcarbamate (compound no. 16)

To (3aR,5R,6S,7R,7aR)-5-[(benzyloxy)methyl]-2-(ethylamino)-5,6,7,7a-tetrahydro-3aH-pyrano[3,2-d][1,3]thiazole-6,7-diol (100.00 mg; 0.30 mmol; 1.00 eq.) in tBuOH (2.00 ml) was added di-tert-butyl dicarbonate (70.94 mg; 0.33 mmol; 1.10 eq.). The reaction was stirred at 37° C. overnight. The desired product was isolated by prep HPLC (neutral conditions, 20-60% B, 20 min, 220 nm) to afford tert-butyl {(3aR,5R,6S,7R,7aR)-5-[(benzyloxy)methyl]-6,7-dihydroxy-5,6,7,7a-tetrahydro-3aH-pyrano[3,2-d][1,3]thiazol-2-yl}ethylcarbamate (48.4 mg, 37%) as a white solid (once lyophilized).

$^1$H NMR (500 MHz, CD$_3$OD) δ 7.42-7.19 (m, 5H), 6.08 (d, J=6.6, 1H), 4.56 (s, 2H), 4.13 (d, J=7.0, 1H), 4.04 (s, 1H), 3.99-3.83 (m, 2H), 3.70 (d, J=10.9, 1H), 3.67-3.52 (m, 3H), 1.54 (s, 9H), 1.18 (t, J=7.0, 3H);
MS (m/z): 439; 440 [M+H]$^+$.

EXAMPLE 27

(3aR,4aR,8aR,9R,9aR)-2-[(tert-butoxycarbonyl)(ethyl)amino]-7-phenyl-3a,4a,5,8a,9,9a-hexahydro[1,3]dioxino[4',5':5,6]pyrano[3,2-d][1,3]thiazol-9-yl methanesulfonate (compound no. 29)

To tert-butyl ethyl[(3aR,4aR,8aS,9R,9aR)-9-hydroxy-7-phenyl-3a,4a,5,8a,9,9a-hexahydro[1,3]dioxino[4',5':5,6]pyrano[3,2-d][1,3]thiazol-2-yl]carbamate (199.00 mg; 0.46 mmol; 1.00 eq.) in DCM (2.00 ml) was added methanesulfonyl chloride (0.05 ml; 0.68 mmol; 1.50 eq.) and N,N-diethylethanamine (0.09 ml; 0.68 mmol; 1.50 eq.). The reaction was stirred at room temperature for 2 h. The desired product was isolated by flash chromatography (KPNH, 20 to 75% EtOAc/Hex) to afford (3aR,4aR,8aR,9R,9aR)-2-[(tert-butoxycarbonyl)(ethyl)amino]-7-phenyl-3a,4a,5,8a,9,9a-hexahydro[1,3]dioxino[4',5':5,6]pyrano[3,2-d][1,3]thiazol-9-yl methanesulfonate (90 mg, 38%) as a white solid (once lyophilized).

$^1$H NMR (500 MHz, CD$_3$OD) δ 7.48 (s, 2H), 7.42-7.21 (m, 3H), 6.33 (d, J=7.4, 1H), 5.70 (s, 1H), 4.76-4.63 (m, 1H), 4.38-4.25 (m, 2H), 4.07 (s, 1H), 3.98-3.73 (m, 4H), 3.08 (s, 3H), 1.55 (s, 9H), 1.19 (t, J=7.0, 3H);
MS (m/z): 515; 537 [M+Na]$^+$.

EXAMPLE 28

(3aR,5S,6S,7R,7aR)—N-(2-biphenyl-4-ylethyl)-2-(ethylamino)-6,7-dihydroxy-5,6,7,7a-tetrahydro-3aH-pyrano[3,2-d][1,3]thiazole-5-carboxamide (compound no. 23)

To (3aR,5S,6S,7R,7aR)-2-(ethylamino)-6,7-dihydroxy-5,6,7,7a-tetrahydro-3aH-pyrano[3,2-d][1,3]thiazole-5-carboxylic acid (70.00 mg; 0.27 mmol; 1.00 eq.) in DMSO (1.00 ml) was added 1-hydroxylbenzotriazole (72.13 mg; 0.53 mmol; 2.00 eq.), N-[3-(dimethylamino)propyl]-N'-ethylcarbodiimide hydrochloride (102.33 mg; 0.53 mmol; 2.00 eq.) and 2-(4-biphenyl)ethylamine (105.30 mg; 0.53 mmol; 2.00 eq.). The reaction was stirred at room temperature overnight. The desired material was isolated by flash column chromatography (KPNH column, 0-20% MeOH/EtOAc) to afford (3aR,5S,6S,7R,7aR)—N-(2-biphenyl-4-ylethyl)-2-(ethylamino)-6,7-dihydroxy-5,6,7,7a-tetrahydro-3aH-pyrano[3,2-d][1,3]thiazole-5-carboxamide (20.9 mg, 18%) as a white solid (once lyophilized).

$^1$H NMR (500 MHz, CD$_3$OD) δ 7.56 (dd, J=20.6, 7.9, 4H), 7.41 (t, J=7.7, 2H), 7.30 (d, J=8.0, 3H), 6.21 (d, J=6.2, 1H), 4.15 (t, J=5.6, 1H), 4.04 (t, J=4.7, 1H), 3.91 (d, J=8.7, 1H), 3.77 (dd, J=8.3, 3.9, 1H), 3.48 (t, J=6.2, 2H), 3.29-3.16 (m, 2H), 2.85 (t, J=7.1, 2H), 1.16 (t, J=7.2, 3H);
MS (m/z): 442; 443 [M+H]$^+$.

EXAMPLE 29

(3aR,5S,6S,7R,7aR)-2-(ethylamino)-6,7-dihydroxy-N,N-dimethyl-5,6,7,7a-tetrahydro-3aH-pyrano[3,2-d][1,3]thiazole-5-carboxamide (compound no. 28)

To (3aR,5S,6S,7R,7aR)-2-(ethylamino)-6,7-dihydroxy-5,6,7,7a-tetrahydro-3aH-pyrano[3,2-d][1,3]thiazole-5-carboxylic acid (70.00 mg; 0.27 mmol; 1.00 eq.) in DMSO (1.00 ml) was added 1-hydroxylbenzotriazole (72.13 mg; 0.53 mmol; 2.00 eq.), N-[3-(dimethylamino)propyl]-N'-ethylcarbodiimide hydrochloride (102.33 mg; 0.53 mmol; 2.00 eq.), dimethylamine hydrochloride (43.53 mg; 0.53 mmol; 2.00 eq.) and n,n-diisopropylethylamine (0.09 ml; 0.53 mmol; 2.00 eq.). The reaction was stirred at room temperature overnight. The desired material was isolated by prep HPLC (0% B for 10 min, then to 30% B for 10 min, 220 nm, 0.1% TFA) to afford (3aR,5S,6S,7R,7aR)-2-(ethylamino)-6,7-dihydroxy-N,N-dimethyl-5,6,7,7a-tetrahydro-3aH-pyrano[3,2-d][1,3]thiazole-5-carboxamide (6.4 mg, 6%) as a white solid (once lyophilized).

$^1$H NMR (500 MHz, CD$_3$OD) δ 6.61 (d, J=4.6, 1H), 4.54 (d, J=6.8, 1H), 4.25 (s, 1H), 3.99 (s, 2H), 3.79-3.66 (m, 2H), 3.44 (s, 3H), 3.27-3.18 (m, 3H), 1.29 (t, J=7.2, 3H);
MS (m/z): 289; 290 [M+H]$^+$.

EXAMPLE 30

(3aR,5S,6S,7R,7aR)-2-(ethylamino)-6,7-dihydroxy-N-phenyl-5,6,7,7a-tetrahydro-3aH-pyrano[3,2-d][1,3]thiazole-5-carboxamide (compound no. 31)

In a similar manner to EXAMPLE 28, (3aR,5S,6S,7R,7aR)-2-(ethylamino)-6,7-dihydroxy-N-phenyl-5,6,7,7a-tetrahydro-3aH-pyrano[3,2-d][1,3]thiazole-5-carboxamide was obtained from (3aR,5S,6S,7R,7aR)-2-(ethylamino)-6,7-dihydroxy-5,6,7,7a-tetrahydro-3aH-pyrano[3,2-d][1,3]thiazole-5-carboxylic acid (100.00 mg; 0.38 mmol; 1.00 eq.) and aniline (0.05 ml; 0.57 mmol; 1.50 eq.). Isolated 9.3 mg (5%) of the title compound as a white solid.

$^1$H NMR (500 MHz, CD$_3$OD) δ 7.60 (d, J=8.6, 2H), 7.33 (t, J=7.6, 2H), 7.15 (d, J=7.3, 1H), 6.69 (s, 1H), 4.30 (s, 1H), 4.25 (d, J=8.2, 1H), 3.97 (d, J=28.3, 2H), 3.45 (m, 2H), 1.31 (t, J=7.3, 3H);
MS (m/z): 337; 338 [M+H]$^+$.

EXAMPLE 31

(3aR,5S,6S,7R,7aR)-2-(ethylamino)-6,7-dihydroxy-N-[2-(4-phenoxyphenyl)ethyl]-5,6,7,7a-tetrahydro-3aH-pyrano[3,2-d][1,3]thiazole-5-carboxamide (compound no. 33)

In a similar manner to EXAMPLE 28, (3aR,5S,6S,7R,7aR)-2-(ethylamino)-6,7-dihydroxy-N-[2-(4-phenoxyphenyl)ethyl]-5,6,7,7a-tetrahydro-3aH-pyrano[3,2-d][1,3]thiazole-5-carboxamide was obtained from (3aR,5S,6S,7R,7aR)-2-(ethylamino)-6,7-dihydroxy-5,6,7,7a-tetrahydro-3aH-pyrano[3,2-d][1,3]thiazole-5-carboxylic acid (100.00 mg; 0.38 mmol; 1.00 eq.) and 2-(4-phenoxyphenyl)ethanamine (0.11 ml; 0.57 mmol; 1.50 eq.). Isolated 7.3 mg (4%) of the title compound as a white solid.

$^1$H NMR (500 MHz, CD$_3$OD) δ 8.02 (s, 1H), 7.23 (t, J=7.7, 2H), 7.12 (d, J=8.3, 2H), 6.98 (t, J=7.0, 1H), 6.83 (dd, J=16.6, 8.5, 3H), 6.46 (s, 1H), 4.19 (s, 1H), 3.93 (d, J=8.3, 1H), 3.89 (s, 1H), 3.74 (s, 1H), 3.43-3.26 (m, 4H), 2.72 (t, J=7.2, 2H), 1.19 (t, J=7.3, 3H);

MS (m/z): 458; 458 [M]$^+$.

EXAMPLE 32

Methyl-(3aR,5S,6S,7R,7aR)-2-(ethylamino)-6,7-dihydroxy-5,6,7,7a-tetrahydro-3aH-pyrano[3,2-d][1,3]thiazole-5-carboxylate (compound no. 42)

To (3aR,5S,6S,7R,7aR)-2-(ethylamino)-6,7-dihydroxy-5,6,7,7a-tetrahydro-3aH-pyrano[3,2-d][1,3]thiazole-5-carboxylic acid (100.00 mg; 0.38 mmol; 1.00 eq.) in methanol (1.00 ml) was added thionyl chloride (0.05 ml; 0.76 mmol; 2.00 eq.). The reaction was stirred at room temperature for 1 h. The desired material was isolated by flash column chromatography (silica gel column, 0 to 50% MeOH/DCM, 15CV) to afford methyl (3aR,5S,6S,7R,7aR)-2-(ethylamino)-6,7-dihydroxy-5,6,7,7a-tetrahydro-3aH-pyrano[3,2-d][1,3]thiazole-5-carboxylate (81.4 mg, 77%) as an off white solid (once lyophilized).

$^1$H NMR (500 MHz, CD$_3$OD) δ 6.30 (d, J=4.8, 1H), 4.24 (d, J=5.6, 1H), 4.15 (t, J=4.6, 1H), 4.08 (t, J=4.5, 1H), 3.98 (t, J=5.2, 1H), 3.75 (s, 3H), 3.43-3.32 (m, 2H), 1.23 (t, J=7.3, 3H);

MS (m/z): 276; 277 [M+H]$^+$.

EXAMPLE 33

(3aR,5S,6S,7R,7aR)-2-(ethylamino)-6,7-dihydroxy-N-methoxy-N-methyl-5,6,7,7a-tetrahydro-3aH-pyrano[3,2-d][1,3]thiazole-5-carboxamide (compound no. 45)

To (3aR,5S,6S,7R,7aR)-2-(ethylamino)-6,7-dihydroxy-5,6,7,7a-tetrahydro-3aH-pyrano[3,2-d][1,3]thiazole-5-carboxylic acid (2.00 g; 7.63 mmol; 1.00 eq.) in DMF (10.00 ml) was added n,o-dimethylhydroxylamine hydrochloride (1 115.70 mg; 11.44 mmol; 1.50 eq.), n,n-di-iso-propylethylamine (3.33 ml; 19.06 mmol; 2.50 eq.) and then 2,4,6-tripropyl-1,3,5,2,4,6-trioxatriphosphinane 2,4,6-trioxide (3.37 ml; 11.44 mmol; 1.50 eq.) (T3P). Reaction was stirred at room temperature for 2 h. The reaction mixture was heated to 65° C. to fully dissolve starting material. Reaction was then stirred at room temperature overnight, concentrated to reduce volume of DMF to 2-3 mL, and the desired product was isolated by flash chromatography (silica gel column, 0 to 50% MeOH/DCM) to afford (3aR,5S,6S,7R,7aR)-2-(ethylamino)-6,7-dihydroxy-N-methoxy-N-methyl-5,6,7,7a-tetrahydro-3aH-pyrano[3,2-d][1,3]thiazole-5-carboxamide (1.23 g, 52%) as a light yellow solid (once lyophilized).

$^1$H NMR (500 MHz, CD$_3$OD) δ 6.26 (d, J=6.0, 1H), 4.60 (s, 1H), 4.11 (s, 1H), 4.00 (s, 2H), 3.77 (s, 3H), 3.36-3.33 (m, 3H), 3.28-3.18 (m, 2H), 1.17 (t, J=7.2, 3H);

MS (m/z): 305; 306 [M+H]$^+$.

EXAMPLE 34

(3aR,5R,6R,7R,7aR)-2-(ethylamino)-6-hydroxy-5-(hydroxymethyl)-5,6,7,7a-tetrahydro-3aH-pyrano[3,2-d][1,3]thiazol-7-yl methanesulfonate (compound no. 46)

To (3aR,4aR,8aR,9R,9aR)-2-[(tert-butoxycarbonyl)(ethyl)amino]-7-phenyl-3a,4a,5,8a,9,9a-hexahydro[1,3]dioxino[4',5':5,6]pyrano[3,2-d][1,3]thiazol-9-yl methanesulfonate (30.00 mg; 0.06 mmol; 1.00 eq.) in DCM (100.00 μl) was added trifluoroacetic acid (10.00 μl; 0.13 mmol; 2.31 eq.). The reaction was stirred at room temperature for 3 h. The desired product was isolated by flash chromatography (KPNH, 0 to 50% MeOH/DCM). To afford (3aR,5R,6R,7R,7aR)-2-(ethylamino)-6-hydroxy-5-(hydroxymethyl)-5,6,7,7a-tetrahydro-3aH-pyrano[3,2-d][1,3]thiazol-7-yl methanesulfonate (19.2 mg, 64%) as a white solid (once lyophilized).

$^1$H NMR (500 MHz, CD$_3$OD) δ 6.33 (d, J=6.4, 1H), 4.89 (t, J=5.6, 1H), 4.27 (t, J=6.1, 1H), 3.81-3.70 (m, 2H), 3.70-3.61 (m, 1H), 3.36-3.33 (m, 2H), 3.25 (dd, J=13.9, 6.7, 1H), 3.22-3.18 (m, 3H), 1.16 (dd, J=8.8, 5.7, 3H);

MS (m/z): 326; 327 [M+H]$^+$.

EXAMPLE 35

(3aR,5R,6S,7R,7aR)-5-[(benzylamino)methyl]-2-(ethylamino)-5,6,7,7a-tetrahydro-3aH-pyrano[3,2-d][1,3]thiazole-6,7-diol (compound no. 48)

To (3aR,5S,6S,7R,7aR)-2-(ethylamino)-6,7-dihydroxy-5,6,7,7a-tetrahydro-3aH-pyrano[3,2-d][1,3]thiazole-5-carbaldehyde (76.00 mg; 0.31 mmol; 1.00 eq.) in methanol (1.00 ml) was added benzylamine (0.05 ml; 0.46 mmol; 1.50 eq.), and sodium cyanoborohydride (9.70 mg; 0.15 mmol; 0.50 eq.) in 0.5 mL MeOH. The reaction was stirred at room temperature for 2 h. The desired product was isolated by prep HPLC (0% B for 10 min, then 0 to 30% B over 10 min, 0.1% TFA, 220 nm) to afford (3aR,5R,6S,7R,7aR)-5-[(benzylamino)methyl]-2-(ethylamino)-5,6,7,7a-tetrahydro-3aH-pyrano[3,2-d][1,3]thiazole-6,7-diol (12.2 mg, 12%) as a white solid (once lyophilized).

$^1$H NMR (500 MHz, CD$_3$OD) δ 7.57-7.38 (m, 5H), 6.63 (d, J=6.4, 1H), 4.29 (d, J=2.6, 2H), 4.24 (dd, J=11.9, 5.1, 1H), 4.02 (t, J=9.1, 1H), 3.90 (t, J=6.6, 1H), 3.55 (d, J=13.3, 1H), 3.44 (dt, J=13.0, 6.7, 3H), 3.26 (dd, J=13.2, 9.7, 1H), 1.30 (t, J=7.3, 3H);

MS (m/z): 337; 338 [M+H]$^+$.

EXAMPLE 36

Methyl-[(3aR,5R,6S,7R,7aR)-6,7-dihydroxy-5-(hydroxymethyl)-5,6,7,7a-tetrahydro-3aH-pyrano[3,2-d][1,3]thiazol-2-yl]ethylcarbamate (compound no. 49)

To (3aR,5R,6S,7R,7aR)-2-(ethylamino)-5-(hydroxymethyl)-5,6,7,7a-tetrahydro-3aH-pyrano[3,2-d][1,3]thiazole-6,7-diol (100.00 mg; 0.40 mmol; 1.00 eq.) in dry THF (12 mL) was added N-ethyl-N-isopropylpropan-2-amine (0.09 ml; 0.52 mmol; 1.30 eq.). The mixture was cooled to 0° C. then methyl chloroformate (0.05 ml, 0.60 mmol; 1.50 eq.) was added dropwise. The reaction was stirred at room temperature for 2 h. The desired product was isolated by flash chromatography (KPNH column, 10 to 100% MeOH/DCM) to afford methyl [(3aR,5R,6S,7R,7aR)-6,7-dihydroxy-5-(hydroxymethyl)-5,6,7,7a-tetrahydro-3aH-pyrano[3,2-d][1,3]thiazol-2-yl]ethylcarbamate (19.6 mg, 16%) as a white solid (once lyophilized).

$^{1}$H NMR (500 MHz, CD$_3$OD) δ 6.13 (d, J=6.8, 1H), 4.20-4.14 (m, 1H), 4.06 (t, J=4.7, 1H), 3.98 (ddd, J=28.5, 13.7, 6.9, 2H), 3.83 (s, 3H), 3.78-3.73 (m, 1H), 3.64 (dd, J=12.1, 6.2, 1H), 3.56 (dd, J=9.2, 4.5, 1H), 3.47-3.40 (m, 1H), 1.19 (t, J=7.0, 3H);

MS (m/z): 306; 307 [M+H]$^+$.

EXAMPLE 37

(3aR,5R,6S,7R,7aR)-5-[(dimethylamino)methyl]-2-(ethylamino)-5,6,7,7a-tetrahydro-3aH-pyrano[3,2-d][1,3]thiazole-6,7-diol (compound no. 51)

To (3aR,5S,6S,7R,7aR)-2-(ethylamino)-6,7-dihydroxy-5,6,7,7a-tetrahydro-3aH-pyrano[3,2-d][1,3]thiazole-5-carbaldehyde (40.00 mg; 0.16 mmol; 1.00 eq.) in MeOH (1.00 ml) was added dimethylamine hydrochloride (15.89 mg; 0.19 mmol; 1.20 eq.), and sodium cyanoborohydride (5.10 mg; 0.08 mmol; 0.50 eq.) in 0.5 mL MeOH. The reaction was stirred at room temperature for 15 min. The desired product was isolated by flash chromatography (KPNH column, 0 to 100% MeOH/DCM, 15CV) to afford (3aR,5R,6S,7R,7aR)-5-[(dimethylamino)methyl]-2-(ethylamino)-5,6,7,7a-tetrahydro-3aH-pyrano[3,2-d][1,3]thiazole-6,7-diol (9.6 mg, 21%) as a white solid (once lyophilized).

$^{1}$H NMR (500 MHz, CD$_3$OD) δ 6.24 (d, J=6.5, 1H), 4.11 (t, J=5.8, 1H), 3.98 (t, J=4.8, 1H), 3.71 (td, J=9.0, 2.0, 1H), 3.25 (ddd, J=18.0, 10.1, 6.2, 3H), 2.71 (dd, J=13.3, 2.1, 1H), 2.51 (dd, J=13.2, 9.0, 1H), 2.28 (s, 6H), 1.16 (t, J=7.2, 3H);

MS (m/z): 275; 276 [M+H]$^+$.

EXAMPLE 38

1-[(3aR,5S,6S,7R,7aR)-2-(ethylamino)-6,7-dihydroxy-5,6,7,7a-tetrahydro-3aH-pyrano[3,2-d][1,3]thiazol-5-yl]-3-phenylpropan-1-one (compound no. 59)

To (3aR,5S,6S,7R,7aR)-2-(ethylamino)-6,7-dihydroxy-N-methoxy-N-methyl-5,6,7,7a-tetrahydro-3aH-pyrano[3,2-d][1,3]thiazole-5-carboxamide (100.00 mg; 0.33 mmol; 1.00 eq.) in THF (1.00 ml) was added dropwise phenethyl magnesium bromide (1.96 ml; 1.00 M; 1.96 mmol; 6.00 eq.). The reaction was stirred at room temperature for 3 h, then phenethyl magnesium bromide (1.96 ml; 1.00 M; 1.96 mmol; 6.00 eq.) was slowly added again and it was continued to stir at room temperature overnight. Another phenethyl magnesium bromide (1.96 ml; 1.00 M; 1.96 mmol; 6.00 eq.) was added and the reaction was stirred at room temperature overnight. It was added water, concentrated, added more water, and lyophilized. It was used half of crude in next step. The other half was purified by prep HPLC (10% B for 5 min then up to 40% B over 20 min, 0.1% TFA, 220 nm) to afford 1-[(3aR,5S,6S,7R,7aR)-2-(ethylamino)-6,7-dihydroxy-5,6,7,7a-tetrahydro-3aH-pyrano[3,2-d][1,3]thiazol-5-yl]-3-phenylpropan-1-one (12.7 mg, 8%) as a white solid (once lyophilized).

$^{1}$H NMR (500 MHz, CD$_3$OD) δ 7.31-7.08 (m, 5H), 6.52 (d, J=6.3, 1H), 4.29 (s, 1H), 4.15-4.03 (m, 2H), 3.92 (s, 1H), 3.41 (d, J=6.6, 2H), 2.92 (dd, J=18.5, 5.9, 4H), 1.28 (t, J=7.3, 3H);

MS (m/z): 350; 351 [M+H]$^+$.

EXAMPLE 39

(3aR,5R,6S,7R,7aR)-2-Ethylamino-5-((S)-1-hydroxy-3-phenyl-propyl)-5,6,7,7a-tetrahydro-3aH-pyrano[3,2-d]thiazole-6,7-diol (compound no. 53)

To crude 1-[(3aR,5S,6S,7R,7aR)-2-(ethylamino)-6,7-dihydroxy-5,6,7,7a-tetrahydro-3aH-pyrano[3,2-d][1,3]thiazol-5-yl]-3-phenylpropan-1-one (200.00 mg; 0.57 mmol; 1.00 eq.) in MeOH (3.00 ml) was added sodium borohydride (21.59 mg; 0.57 mmol; 1.00 eq.). Reaction was stirred at room temperature for 30 min. The desired product was isolated by prep HPLC (0% B for 10 min, then up to 30% B for 10 min, 0.1% TFA, 220 nm) to afford (3aR,5R,6S,7R,7aR)-2-Ethylamino-5-((S)-1-hydroxy-3-phenyl-propyl)-5,6,7,7a-tetrahydro-3aH-pyrano[3,2-d]thiazole-6,7-diol (1.9 mg, 1%) as a white solid (once lyophilized).

$^{1}$H NMR (500 MHz, CD$_3$OD) δ 7.29-7.18 (m, 4H), 7.15 (t, J=7.2, 1H), 6.62 (d, J=6.5, 1H), 4.21 (t, J=6.4, 1H), 3.91 (t, J=6.1, 1H), 3.87 (m, 2H), 3.83-3.76 (m, 1H), 3.50-3.37 (m, 2H), 2.85-2.74 (m, 1H), 2.71-2.56 (m, 1H), 1.92 (d, J=9.1, 1H), 1.78 (s, 1H), 1.28 (t, J=7.3, 3H);

MS (m/z): 352; 353 [M+H]$^+$.

Arbitrary assigned stereochemistry of 6-alcohol.

EXAMPLE 40

(3aR,5R,6S,7R,7aR)-2-Ethylamino-5-((R)-1-hydroxy-3-phenyl-propyl)-5,6,7,7a-tetrahydro-3aH-pyrano[3,2-d]thiazole-6,7-diol (compound no. 54)

(3aR,5R,6S,7R,7aR)-2-Ethylamino-5-((R)-1-hydroxy-3-phenyl-propyl)-5,6,7,7a-tetrahydro-3aH-pyrano[3,2-d]thiazole-6,7-diol was the other isomer isolated from 1-[(3aR,5S,6S,7R,7aR)-2-(ethylamino)-6,7-dihydroxy-5,6,7,7a-tetrahydro-3aH-pyrano[3,2-d][1,3]thiazol-5-yl]-3-phenylpropan-1-one (1.5 mg, 1%).

$^{1}$H NMR (500 MHz, CD$_3$OD) δ 7.19-7.08 (m, 4H), 7.05 (t, J=7.2, 1H), 6.49 (d, J=6.7, 1H), 4.15 (t, J=6.3, 1H), 3.83 (t, J=5.5, 1H), 3.75 (d, J=9.5, 1H), 3.64-3.56 (m, 1H), 3.56-3.48 (m, 1H), 3.37-3.26 (m, 2H), 2.82-2.66 (m, 1H), 2.55 (ddd, J=13.5, 9.7, 6.9, 1H), 1.86-1.56 (m, 2H), 1.18 (t, J=7.3, 3H);

MS (m/z): 352; 353 [M+H]$^+$.

Arbitrary assigned stereochemistry of 6-alcohol.

EXAMPLE 41

1-[(3aR,5S,6S,7R,7aR)-2-(ethylamino)-6,7-dihydroxy-5,6,7,7a-tetrahydro-3aH-pyrano[3,2-d][1,3]thiazol-5-yl]-4-phenylbutan-1-one (compound no. 60)

In a similar manner to EXAMPLE 38, 1-[(3aR,5S,6S,7R,7aR)-2-(ethylamino)-6,7-dihydroxy-5,6,7,7a-tetrahydro-3aH-pyrano[3,2-d][1,3]thiazol-5-yl]-4-phenylbutan-1-one was obtained from 1-[(3aR,5S,6S,7R,7aR)-2-(ethylamino)-6,7-dihydroxy-N-methoxy-N-methyl-5,6,7,7a-tetrahydro-3aH-pyrano[3,2-d][1,3]thiazole-5-carboxamide (100.00 mg; 0.33 mmol; 1.00 eq.) and 3-(phenyl)propyl magnesium bromide (1.96 ml; 1.00 M; 1.96 mmol; 6.00 eq.) as a white sticky solid (once lyophilized) (16.5 mg, 11%).

$^{1}$H NMR (500 MHz, CD$_3$OD) δ 7.26 (t, J=7.6, 2H), 7.17 (d, J=6.7, 3H), 6.53 (d, J=6.2, 1H), 4.29 (s, 1H), 4.09 (d, J=7.4, 1H), 4.05 (s, 1H), 3.91 (s, 1H), 3.41 (d, J=7.1, 2H), 2.62 (t, J=7.5, 4H), 1.91 (dd, J=15.1, 7.4, 2H), 1.29 (t, J=7.3, 3H);

MS (m/z): 364; 365 [M+H]$^+$.

EXAMPLE 42

(3aR,5R,6S,7R,7aR)-2-(ethylamino)-5-((R)1-hydroxy-4-phenylbutyl)-5,6,7,7a-tetrahydro-3aH-pyrano[3,2-d][1,3]thiazole-6,7-diol (compound no. 55)

In a similar manner to EXAMPLE 39, (3aR,5R,6S,7R,7aR)-2-(ethylamino)-5-((R)1-hydroxy-4-phenylbutyl)-5,6,7,7a-tetrahydro-3aH-pyrano[3,2-d][1,3]thiazole-6,7-diol was obtained as a colorless oil from 1-[(3aR,5S,6S,7R,7aR)-2-(ethylamino)-6,7-dihydroxy-5,6,7,7a-tetrahydro-3aH-pyrano[3,2-d][1,3]thiazol-5-yl]-3-phenylpropan-1-one (200.00 mg; 0.57 mmol; 1.00 eq.) (4 mg, 2%).

$^1$H NMR (500 MHz, CD$_3$OD) δ 7.39-7.03 (m, 5H), 6.59 (d, J=6.6, 1H), 4.23 (s, 1H), 3.92 (s, 2H), 3.62 (d, J=3.2, 2H), 3.51-3.37 (m, 2H), 2.81-2.53 (m, 2H), 1.87 (s, 1H), 1.80-1.44 (m, 3H), 1.28 (t, J=7.3, 3H);

MS (m/z): 366; 367 [M+H]$^+$.

Arbitrary assigned stereochemistry of 6-alcohol.

EXAMPLE 43

(3aR,5R,6S,7R,7aR)-2-(ethylamino)-5-((S)1-hydroxy-4-phenylbutyl)-5,6,7,7a-tetrahydro-3aH-pyrano[3,2-d][1,3]thiazole-6,7-diol (compound no. 56)

In a similar manner to EXAMPLE 38, (3aR,5R,6S,7R,7aR)-2-(ethylamino)-5-((S)1-hydroxy-4-phenylbutyl)-5,6,7,7a-tetrahydro-3aH-pyrano[3,2-d][1,3]thiazole-6,7-diol was obtained as a colorless oil from 1-[(3aR,5S,6S,7R,7aR)-2-(ethylamino)-6,7-dihydroxy-5,6,7,7a-tetrahydro-3aH-pyrano[3,2-d][1,3]thiazol-5-yl]-3-phenylpropan-1-one (200.00 mg; 0.57 mmol; 1.00 eq.) (2.4 mg, 1%).

$^1$H NMR (500 MHz, CD$_3$OD) δ 7.24 (d, J=7.6, 3H), 7.19 (s, 2H), 6.61 (d, J=6.5, 1H), 4.18 (t, J=6.5, 1H), 3.90 (s, 2H), 3.84-3.70 (m, 1H), 3.51-3.38 (m, 3H), 2.64 (s, 2H), 1.78 (dd, J=16.7, 9.3, 1H), 1.58 (d, J=63.1, 3H), 1.28 (t, J=7.2, 3H);

MS (m/z): 366; 367 [M+H]$^+$.

Arbitrary assigned stereochemistry of 6-alcohol.

EXAMPLE 44

Phenyl-[(3aR,5R,6S,7R,7aR)-6,7-dihydroxy-5-(hydroxymethyl)-5,6,7,7a-tetrahydro-3aH-pyrano[3,2-d][1,3]thiazol-2-yl]ethylcarbamate (compound no. 63)

In a similar manner to EXAMPLE 36, phenyl [(3aR,5R,6S,7R,7aR)-6,7-dihydroxy-5-(hydroxymethyl)-5,6,7,7a-tetrahydro-3aH-pyrano[3,2-d][1,3]thiazol-2-yl]ethylcarbamate was obtained from (3aR,5R,6S,7R,7aR)-2-(ethylamino)-5-(hydroxymethyl)-5,6,7,7a-tetrahydro-3aH-pyrano[3,2-d][1,3]thiazole-6,7-diol (100.00 mg; 0.40 mmol; 1.00 eq.) and phenyl chloridocarbonate (0.05 ml; 0.40 mmol; 1.00 eq.). 96 mg (65%) of the title compound were isolated as a white solid.

$^1$H NMR (500 MHz, CD$_3$OD) δ 7.43 (t, J=7.8, 2H), 7.28 (t, J=7.4, 1H), 7.18 (d, J=8.4, 2H), 6.17 (d, J=6.9, 1H), 4.27-4.19 (m, 1H), 4.19-4.10 (m, 2H), 4.09 (t, J=4.7, 1H), 3.76 (dd, J=12.0, 2.2, 1H), 3.64 (dd, J=12.0, 6.2, 1H), 3.58 (dd, J=9.0, 4.3, 1H), 3.51-3.44 (m, 1H), 1.34 (t, J=6.9, 3H);

MS (m/z): 368; 369 [M+H]$^+$.

EXAMPLE 45 benzyl [(3aR,5R,6S,7R,7aR)-6,7-dihydroxy-5-(hydroxymethyl)-5,6,7,7a-tetrahydro-3aH-pyrano[3,2-d][1,3]thiazol-2-yl]ethylcarbamate (compound no. 62)

In a similar manner to EXAMPLE 36, benzyl [(3aR,5R,6S,7R,7aR)-6,7-dihydroxy-5-(hydroxymethyl)-5,6,7,7a-tetrahydro-3aH-pyrano[3,2-d][1,3]thiazol-2-yl]ethylcarbamate was obtained from (3aR,5R,6S,7R,7aR)-2-(ethylamino)-5-(hydroxymethyl)-5,6,7,7a-tetrahydro-3aH-pyrano[3,2-d][1,3]thiazole-6,7-diol (100.00 mg; 0.40 mmol; 1.00 eq.) benzyl chloridocarbonate (0.06 ml, 0.40 mmol; 1.00 eq.). 69 mg (45%) of the title compound were isolated as a white solid.

$^1$H NMR (500 MHz, CD$_3$OD) δ 7.43 (t, J=7.8, 2H), 7.28 (t, J=7.4, 1H), 7.18 (d, J=8.4, 2H), 6.17 (d, J=6.9, 1H), 4.27-4.19 (m, 1H), 4.19-4.10 (m, 2H), 4.09 (t, J=4.7, 1H), 3.76 (dd, J=12.0, 2.2, 1H), 3.64 (dd, J=12.0, 6.2, 1H), 3.58 (dd, J=9.0, 4.3, 1H), 3.51-3.44 (m, 1H), 1.34 (t, J=6.9, 3H);

MS (m/z): 382; 383 [M+H]$^+$.

EXAMPLE 46

N-((3aR,5R,6S,7R,7aR)-6,7-Dihydroxy-5-hydroxymethyl-5,6,7,7a-tetrahydro-3aH-pyrano[3,2-d]thiazol-2-yl)-N-ethyl-3,3-dimethyl-butyramide (compound no. 104)

N-((3aR,5R,6S,7R,7aR)-6,7-dihydroxy-5-hydroxymethyl-5,6,7,7a-tetrahydro-3aH-pyrano[3,2-d]thiazol-2-yl)-N-ethyl-3,3-dimethyl-butyramide was obtained from (3aR,5R,6S,7R,7aR)-2-Ethylamino-5-hydroxymethyl-5,6,7,7a-tetrahydro-3aH-pyrano[3,2-d]thiazol-6,7-diol (200.00 mg; 0.81 mmol; 1.00 eq.) and 3,3-dimethylbutyric acid (0.12 ml; 0.97 mmol; 1.20 eq.). 40.0 mg (10.8%) of the title compound were isolated as a white solid.

$^1$H NMR (500 MHz, CD$_3$OD) δ 6.26 (d, J=7.1, 1H), 4.27-4.18 (m, 1H), 4.07 (t, J=5.1, 1H), 3.99 (dt, J=14.8, 7.7, 2H), 3.78 (dd, J=12.0, 2.2, 1H), 3.67 (dd, J=12.1, 6.2, 1H), 3.57 (dd, J=9.0, 4.7, 1H), 3.53-3.46 (m, 1H), 2.62 (q, J=16.1, 2H), 1.29 (t, J=7.1, 3H), 1.09 (s, 9H);

MS (m/z): 346; 347 [M+H]$^+$.

EXAMPLE 47

2-Ethylamino-5-[4-(1-hydroxy-1-phenyl-ethyl)-[1,2,3]triazol-1-ylmethyl]-5,6,7,7a-tetrahydro-3aH-pyrano[3,2-d]thiazol-6,7-diol (compound no. 67)

In a 10 mL rb flask was added (3aR,5R,6S,7R,7aR)-5-(azidomethyl)-2-(ethylamino)-5,6,7,7a-tetrahydro-3aH-pyrano[3,2-d][1,3]thiazole-6,7-diol (40 mg, 0.15 mmol, 1.00 eq.), copper turnings (66 mg; 1.05 mmol; 7.00 eq.) and copper (II)sulfate pentahydrate (7.5 mg; 0.03 mmol; 0.20 eq.). The flask was evacuated and filled with nitrogen. This procedure was repeated twice before ethanol (0.5 ml)/water (0.7 ml)/2-methylpropan-2-ol (1.3 ml) and 2-phenylbut-3-yn-2-ol (22 mg; 0.45 mmol; 3.00 eq.) was added into the mixture and stirred for 24 h to get the reaction completed. Product formation was confirmed by LCMS. The solution was diluted with 2 mL H$_2$O, dried and separated with mass based prep HPLC to afford the desired product.

Yield: 21% (16 mg, off-white solid).

The following compounds were prepared in a similar manner.

Compound no. 95
    400 MHz, DMSO-d6: δ 10.41 (s, 1H), 7.37-8.09 (m, 5H), 6.52 (s, 1H), 5.70-5.79 (m, 4H), 4.32-4.71 (m, 3H), 4.04-4.06 (m, 1H), 3.74-3.78 (m, 2H), 3.25-3.44 (m, 3H), 1.05 (t, J=7.13 Hz, 3H).
    LCMS: (Method A) 498.0 (M+H), RT 2.65 min, 99.1% (Max), 99.3% (254 nm).
    HPLC: (Method A) RT 2.64 min, 99.41% (Max), 99.21% (254 nm).
Compound no. 65
    400 MHz, DMSO-d6: δ 7.88 (s, 1H), 5.81 (s, 1H), 5.17 (s, 2H), 4.50-4.71 (m, 2H), 4.11-4.14 (m, 1H), 3.36-3.44 (m, 7H), 2.17 (s, 3H), 1.99 (s, 3H), 1.81 (s, 3H), 1.14 (t, J=7.12 Hz, 3H).
    LCMS: (Method A) 422.2 (M+H-TFA), RT 1.86 min, 91.11% (Max), 93.37% (220 nm).
Compound no. 96
    400 MHz, DMSO-d6: δ 10.49 (s, 1H), 10.18 (s, 1H), 8.04 (s, 1H), 6.49-6.50 (m, 1H), 5.84 (s, 2H), 5.30-5.36 (m, 2H), 4.51-4.75 (m, 2H), 4.11-4.14 (m, 1H), 3.80-3.90 (m, 2H), 3.41-3.48 (m, 2H), 2.50 (s, 1H), 2.11 (s, 1H), 1.13 (s, 1H).
    LCMS: (Method B) 409.3 (M+H), RT 2.82 min, 95.76% (Max), 93.66% (254 nm).
    HPLC: (Method A) RT 2.82 min, 96.99% (Max), 96.51% (220 nm).
Compound no. 97
    400 MHz, DMSO-d6: δ 10.42 (s, 1H), 10.08 (s, 1H), 8.07 (s, 1H), 7.26-7.85 (m, 5H), 6.50 (d, J=6.52 Hz, 1H), 5.84 (s, 2H), 5.50 (s, 2H), 4.72-4.77 (m, 1H), 4.54-4.60 (m, 1H), 4.10-4.13 (m, 1H), 3.50-3.88 (m, 2H), 3.34-3.37 (m, 2H), 1.16 (t, J=Hz, 3H).
    LCMS: (Method A) 462.0 (M+H), RT 1.46 min, 96.39% (Max), 95.56% (254 nm).
    HPLC: (Method B) RT 3.61 min, 98.15% (Max), 97.65% (220 nm).
Compound no. 66
    400 MHz, DMSO-d6: δ 8.12 (s, 1H), 7.90 (s, 1H), 6.76-6.77 (m, 2H), 6.16 (s, 1H), 5.96-5.97 (m, 2H), 5.23-5.27 (m, 2H), 5.12 (s, 2H), 4.62-4.66 (m, 1H), 4.38-4.44 (m, 1H), 3.97 (t, J=5.92 Hz, 1H), 3.79-3.82 (m, 1H), 3.65-3.69 (m, 1H), 3.10-3.15 (m, 2H), 1.04 (t, J=7.18 Hz, 3H).
    LCMS: (Method A) 479.0 (M+H), RT 2.11 min, 96.40% (Max), 97.40% (220 nm).
    HPLC: (Method A) RT 2.08 min, 96.98% (Max), 96.57% (220 nm).
Compound no. 67
    400 MHz, DMSO-d6: δ 10.42 (s, 1H), 10.10 (s, 1H), 7.78 (s, 1H), 7.18-7.44 (m, 5H), 6.52-6.53 (m, 1H), 5.85-5.87 (m, 3H), 4.68-4.72 (m, 1H), 4.52-4.54 (m, 1H), 4.11-4.14 (m, 1H), 3.87-3.89 (m, 1H), 3.78-3.81 (m, 1H), 3.34-3.40 (m, 2H), 1.79 (s, 3H), 1.14 (t, J=7.04 Hz, 3H).
    LCMS: (Method A) 420.3 (M+H-TFA), RT 2.21 min, 91.36% (Max), 91.49% (220 nm).
    HPLC: (Method A) RT 2.28 min, 95.50% (Max), 95.05% (220 nm).
Compound no. 68
    400 MHz, DMSO-d6: δ 7.73 (s, 1H), 7.23-7.39 (m, 5H), 6.17 (s, 1H), 5.94-5.97 (m, 1H), 5.75-5.79 (m, 1H), 5.21 (s, 2H), 4.60-4.64 (m, 1H), 4.40-4.42 (m, 1H), 3.99 (s, 1H), 3.81-3.82 (m, 1H), 3.12-3.73 (m, 1H), 3.46-3.48 (m, 1H), 3.40-3.42 (m, 1H), 3.12-3.24 (m, 2H), 1.04 (t, J=Hz, J=7.18 Hz, 3H).
    LCMS: (Method A) 406.2 (M+H), RT 1.97 min, 96.77% (Max), 96.00% (220 nm).
    HPLC: (Method A) RT 1.98 min, 96.70% (Max), 96.73% (220 nm).

Compound no. 69
    400 MHz, DMSO-d6: δ 8.12-8.21 (m, 3H), 7.93 (s, 1H), 7.45-7.47 (m, 2H), 7.43-7.43 (m, 2H), 7.18-7.21 (m, 2H), 6.05 (d, J=6.20 Hz, 1H), 5.64 (s, 2H), 5.09-5.15 (m, 2H), 4.53-4.57 (m, 1H), 4.29-4.33 (m, 1H), 3.90-3.93 (m, 1H), 3.76-3.77 (m, 1H), 3.62 (s, 1H), 3.04-3.09 (m, 2H), 1.00 (t, J=7.16 Hz, 3H).
    LCMS: (Method A) 479.3 (M+H), RT 3.54 min, 99.26% (Max), 99.20% (220 nm).
    HPLC: (Method A) RT 3.63 min, 98.78% (Max), 99.17% (220 nm).
Compound no. 98
    400 MHz, DMSO-d6: δ 8.58 (s, 1H), 8.28 (s, 1H), 8.00-8.21 (m, 1H), 7.58-7.71 (m, 3H), 7.35-7.45 (m, 5H), 6.51 (s, 1H), 6.25 (s, 2H), 5.23-5.42 (m, 2H), 4.73-4.77 (m, 1H), 4.53-4.55 (m, 1H), 4.00-4.02 (m, 1H), 3.39-3.41 (m, 1H), 3.13-3.14 (m, 2H), 1.04 (t, J=7.12 Hz, 3H).
    LCMS: (Method A) 555.0 (M+H), RT 3.802 min, 97.82% (Max), 98.36% (254 nm).
    HPLC: (Method A) RT 3.78 min, 99.12% (Max), 98.58% (254 nm).
Compound no. 99
    400 MHz, DMSO-d6: δ 10.33 (s, 1H), 10.19 (s, 1H), 7.55 (s, 1H), 7.23-7.33 (m, 2H), 6.49 (d, J=6.52 Hz, 1H), 5.79 (s, 2H), 4.63-4.67 (m, 1H), 3.79-4.49 (m, 4H), 1.23-1.35 (m, 2H), 1.12-1.16 (m, 2H), 1.05 (t, J=7.00 Hz, 3H).
    LCMS: (Method A) 416.0 (M+H), RT 2.98 min, 94.30% (Max), 94.52% (220 nm).
    HPLC: (Method A) RT 2.97 min, 95.23% (Max), 95.12% (220 nm).
Compound no. 100
    400 MHz, DMSO-d6: δ 10.23 (s, 1H), 7.82 (s, 1H), 7.13-7.30 (m, 5H), 6.53 (s, 1H), 5.62 (s, 2H), 4.10-4.69 (m, 3H), 3.24-3.81 (m, 5H), 2.50-2.50 (m, 2H), 2.03-2.06 (m, 2H), 1.69-1.71 (m, 2H), 1.53-1.55 (m, 2H), 1.10 (t, J=7.20 Hz, 3H).
    LCMS: (Method A) 444.3 (M+H), RT 3.35 min, 98.21% (Max), 97.86% (254 nm).
    HPLC: (Method A) RT 3.35 min, 98.84% (Max), 98.87% (220 nm).
Compound no. 70
    400 MHz, DMSO-d6: δ 8.12 (s, 1H), 8.01 (d, J=3.76 Hz, 1H), 7.56-7.59 (m, 2H), 7.41-7.47 (m, 1H), 7.36-7.41 (m, 3H), 6.13-6.13 (m, 1H), 5.28-5.32 (m, 2H), 4.69-4.73 (m, 1H), 4.47-4.53 (m, 1H), 3.96-3.99 (m, 1H), 3.79-3.81 (m, 1H), 3.64-3.64 (m, 1H), 3.14 (q, J=7.08 Hz, 2H), 1.04 (t, J=6.64 Hz, 3H).
    LCMS: (Method A) 474.0 (M+H), RT 2.88 min, 96.13% (Max), 95.61% (220 nm).
    HPLC: (Method A) RT 3.05 min, 96.05% (Max), 95.31% (220 nm).
Compound no. 71
    400 MHz, DMSO-d6: δ 7.75 (s, 1H), 7.12-7.16 (m, 2H), 6.78-6.80 (m, 2H), 6.60-6.63 (m, 1H), 6.14 (s, 1H), 5.26 (s, 2H), 4.53-4.63 (m, 3H), 4.37-4.39 (m, 1H), 3.11-3.96 (m, 6H), 2.92 (s, 3H), 2.49 (s, 1H), 1.04 (t, J=7.12 Hz, 3H).
    LCMS: (Method A) 419.3 (M+H), RT 1.72 min, 98.06% (Max), 98.21% (220 nm).
    HPLC: (Method A) RT 1.72 min, 98.02% (Max), 97.98% (220 nm).
Compound no. 72
    400 MHz, DMSO-d6: δ 8.12 (s, 1H), 7.23-7.28 (m, 2H), 7.13-7.15 (m, 2H), 7.03-7.06 (m, 1H), 6.21-6.35 (m, 1H), 5.29-5.40 (m, 2H), 5.15 (s, 2H), 4.68-4.72 (m, 1H), 4.50-4.52 (m, 1H), 4.01-4.02 (m, 1H), 3.76-3.82 (m, 2H), 3.17-3.19 (m, 2H), 1.07 (t, J=7.16 Hz, 3H).
    LCMS: (Method A) 484.0 (M+H), RT. 3.19 min, 97.31% (Max), 97.72% (220 nm).

HPLC: (Method A) RT 3.22 min, 98.55% (Max), 98.65% (220 nm).

Compound no. 73

400 MHz, DMSO-d6: δ 8.12 (s, 1H), 7.36-7.56 (m, 4H), 6.28 (s, 1H), 5.40 (s, 2H), 5.20 (s, 2H), 4.68-4.72 (m, 1H), 4.46-4.52 (m, 1H), 4.01-4.11 (m, 1H), 3.75-3.83 (m, 2H), 3.32 (s, 1H), 3.17-3.17 (m, 2H), 1.06 (t, J=7.16 Hz, 3H).

LCMS: (Method A) 431.3 (M+H), RT 2.55 min, 97.26% (Max), 97.44% (220 nm).

HPLC: (Method A) RT 2.58 min, 96.52% (Max), 96.44% (220 nm).

Compound no. 74

400 MHz, DMSO-d6: δ 8.10-8.13 (m, 1H), 7.31-7.34 (m, 2H), 7.06 (d, J=8.96 Hz, 2H), 6.19 (s, 1H), 5.32 (s, 2H), 5.12 (s, 2H), 4.67-4.70 (m, 1H), 4.44-4.49 (m, 1H), 4.00 (t, J=5.20 Hz, 1H), 3.81 (d, J=4.40 Hz, 1H), 3.70-3.72 (m, 1H), 3.12-3.14 (m, 2H), 1.05 (t, J=7.20 Hz, 3H).

LCMS: (Method A) 422.0 (M+H), RT 2.09 min, 98.95% (Max), 98.60% (220 nm).

HPLC: (Method A) RT 2.13 min, 98.35% (Max), 98.44% (220 nm).

Compound no. 75

400 MHz, DMSO-d6: δ 8.10 (s, 1H), 7.21-7.25 (m, 1H), 6.87-6.96 (m, 3H), 6.24 (s, 1H), 5.40-5.43 (m, 2H), 5.16-5.19 (m, 1H), 4.71 (d, J=2.28 Hz, 2H), 4.45-4.68 (m, 3H), 3.99-4.02 (m, 1H), 3.73-3.83 (m, 3H), 3.16-3.37 (m, 3H), 1.04 (t, J=Hz, J=7.18 Hz, 3H).

LCMS: (Method A) 436.3 (M+H), RT 2.02 min, 98.91% (Max), 98.75% (220 nm).

HPLC: (Method A) RT 2.13 min, 98.60% (Max), 98.98% (220 nm).

Compound no. 76

400 MHz, DMSO-d6: δ 8.13 (s, 1H), 8.08 (s, 1H), 7.20-7.24 (m, 1H), 6.86-6.98 (m, 3H), 6.17 (d, J=5.68 Hz, 2H), 5.10-5.28 (m, 5H), 4.66-4.70 (m, 2H), 4.43-4.49 (m, 1H), 3.97-4.00 (m, 1H), 3.41-3.74 (m, 2H), 3.11-3.41 (m, 3H), 1.30 (d, J=6.44 Hz, 3H), 1.06 (t, J=Hz, 3H).

LCMS: (Method A) 450.0 (M+H), RT 2.26 min, 95.99% (Max), 97.05% (220 nm).

HPLC: (Method A) RT 2.27 min, 97.61% (Max), 97.24% (220 nm).

Compound no. 101

400 MHz, DMSO-d6: δ 8.14 (s, 1H), 6.95-7.08 (m, 1H), 6.51-6.52 (m, 1H), 6.32-6.34 (m, 2H), 5.85 (s, 2H), 5.02 (s, 2H), 4.74-4.77 (m, 1H), 4.56-4.62 (m, 1H), 3.37-4.16 (m, 7H), 1.14 (t, J=7.10 Hz, 3H).

LCMS: (Method B) 421.0 (M+H-TFA), RT 3.49 min, 90.91% (Max), 91.70% (220 nm).

HPLC: (Method B) RT 3.60 min, 93.91% (Max), 93.29% (254 nm).

Compound no. 77

400 MHz, DMSO-d6: δ 8.09 (s, 1H), 7.14-7.18 (m, 1H), 6.75-6.84 (m, 3H), 6.26 (s, 1H), 5.21-5.40 (m, 2H), 5.08 (s, 2H), 4.68-4.72 (m, 1H), 4.46-4.52 (m, 1H), 4.02 (s, 1H), 3.74-3.81 (m, 2H), 3.17-3.31 (m, 3H), 2.27 (s, 3H), 1.07 (t, J=7.12 Hz, 3H).

LCMS: (Method A) 420.0 (M+H), RT 2.98 min, 98.18% (Max), 98.30% (220 nm).

HPLC: (Method A) RT 2.98 min, 97.94% (Max), 97.94% (220 nm).

Compound no. 78

400 MHz, DMSO-d6: δ 8.11 (s, 1H), 7.29-7.33 (m, 1H), 6.99-7.15 (m, 3H), 6.20 (s, 1H), 5.33-5.42 (m, 2H), 5.15 (s, 2H), 4.67-4.71 (m, 1H), 4.44-4.50 (m, 1H), 3.98-4.01 (m, 1H), 3.71-3.82 (m, 2H), 3.14-3.15 (m, 2H), 1.03 (t, J=7.16 Hz, 3H).

LCMS: (Method A) 440.0 (M+H), RT 3.10 min, 99.03% (Max), 99.09% (220 nm).

HPLC: (Method A) RT 3.23 min, 97.75% (Max), 97.80% (220 nm).

Compound no. 79

400 MHz, DMSO-d6: δ 8.13 (s, 1H), 7.29-7.35 (m, 1H), 6.85-6.96 (m, 1H), 6.75-6.80 (m, 2H), 6.23 (s, 1H), 5.23-5.39 (m, 2H), 5.14 (s, 2H), 4.67-4.72 (m, 1H), 4.49-4.51 (m, 1H), 3.99-4.01 (m, 1H), 3.74-3.81 (m, 2H), 3.15-3.35 (m, 3H), 1.06 (s, 3H).

LCMS: (Method A) 424.3 (M+H), RT. 2.80 min, 97.86% (Max), 97.89% (220 nm).

HPLC: (Method A) RT 2.94 min, 97.98% (Max), 97.64% (220 nm).

Compound no. 80

400 MHz, DMSO-d6: δ 8.09 (s, 1H), 7.16-7.20 (m, 1H), 6.51-6.62 (m, 3H), 6.19 (s, 1H), 5.25-5.30 (m, 2H), 5.09 (s, 2H), 4.66-4.70 (m, 1H), 4.44-4.49 (m, 1H), 3.97-4.00 (m, 1H), 3.75-3.81 (m, 2H), 3.72 (s, 3H), 3.12-3.31 (m, 3H), 1.06 (t, J=7.16 Hz, 3H).

LCMS: (Method A) 436.0 (M+H), RT 2.69 min, 97.54% (Max), 97.45% (220 nm).

HPLC: (Method A) RT 2.72 min, 97.47% (Max), 97.85% (220 nm).

Compound no. 81

400 MHz, DMSO-d6: δ 8.21 (s, 1H), 7.38-7.60 (m, 4H), 6.13 (d, J=6.24 Hz, 1H), 5.24 (s, 3H), 4.66-4.70 (m, 1H), 4.43-4.48 (m, 1H), 3.69-3.82 (m, 3H), 3.56 (s, 1H), 3.08-3.32 (m, 6H), 1.03 (t, J=7.20 Hz, 3H).

LCMS: (Method A) 484.0 (M+H), RT 2.16 min, 97.59% (Max), 97.27% (220 nm).

HPLC: (Method A) RT 2.14 min, 97.49% (Max), 97.73% (220 nm).

Compound no. 82

400 MHz, DMSO-d6: δ 10.39 (s, 1H), 10.06 (s, 1H), 8.22 (s, 1H), 7.46-7.74 (m, 4H), 7.09-7.13 (m, 1H), 6.50-6.52 (m, 1H), 5.84 (s, 2H), 5.33 (s, 2H), 4.77-4.80 (m, 1H), 4.58-4.64 (m, 1H), 3.35-4.16 (m, 5H), 1.14 (t, J=7.11 Hz, 3H).

LCMS: (Method A) 431.3 (M+H), RT 2.55 min, 97.92% (Max), 97.59% (220 nm).

HPLC: (Method A) RT 2.56 min, 97.37% (Max), 97.39% (220 nm).

Compound no. 102

400 MHz, DMSO-d6: δ 10.54 (s, 1H), 10.17 (s, 1H), 8.13-8.22 (m, 4H), 6.99-7.41 (m, 4H), 6.52 (d, J=6.28 Hz, 1H), 5.89 (s, 2H), 5.25 (s, 2H), 4.74-4.79 (m, 1H), 4.56-4.61 (m, 1H), 3.81-4.14 (m, 5H), 1.16 (t, J=7.12 Hz, 3H).

LCMS: (Method A) 435.3 (M+H), RT 1.69 min, 95.12% (Max), 95.13% (220 nm).

HPLC: (Method A) RT 1.70 min, 96.42% (Max), 96.51% (220 nm).

Compound no. 83

400 MHz, DMSO-d6: δ 8.57 (s, 1H), 8.21 (s, 1H), 7.29-7.42 (m, 3H), 7.02-7.05 (m, 1H), 6.51-6.57 (m, 1H), 5.99 (s, 1H), 5.87 (s, 1H), 5.26 (d, J=3.36 Hz, 2H), 4.60-4.80 (m, 2H), 4.06-4.27 (m, 3H), 2.52-2.58 (m, 2H), 1.16 (t, J=7.13 Hz, 3H).

LCMS: (Method A) 449.3 (M+H), RT 1.81 min, 94.91% (Max), 95.54% (220 nm).

HPLC: (Method A) RT 1.79 min, 94.46% (Max), 94.54% (220 nm).

Compound no. 84

400 MHz, DMSO-d6: δ 9.02 (s, 1H), 8.11 (s, 1H), 6.71-7.06 (m, 4H), 6.19 (d, J=5.48 Hz, 1H), 5.11-5.31 (m, 2H), 5.09 (s, 2H), 4.66-4.70 (m, 1H), 4.44-4.50 (m, 1H), 3.97-4.00 (m, 1H), 3.41-3.82 (m, 3H), 3.14 (q, J=7.04 Hz, 2H), 1.05 (t, J=6.80 Hz, 3H).

LCMS: (Method A) 422.0 (M+H), RT 2.23 min, 95.82% (Max), 96.66% (220 nm).

HPLC: (Method A) RT 2.20 min, 96.51% (Max), 96.26% (220 nm).

Compound no. 85

400 MHz, DMSO-d6: δ 8.08 (s, 1H), 8.06 (s, 1H), 7.42-7.44 (m, 1H), 6.92-7.20 (m, 3H), 6.92-6.96 (m, 1H), 6.16 (d, J=5.04 Hz, 1H), 5.13-5.41 (m, 4H), 4.93-4.96 (m, 2H), 4.67-4.71 (m, 1H), 4.46-4.48 (m, 1H), 3.11-4.21 (m, 6H), 1.22 (d, J=6.04 Hz, 3H), 1.04 (t, J=7.08 Hz, 3H).

LCMS: (Method A) 450.3 (M+H), RT 2.35 min, 95.58% (Max), 95.57% (220 nm).

HPLC: (Method A) RT 2.47 min, 97.29% (Max), 97.24% (220 nm).

Compound no. 86

400 MHz, DMSO-d6: δ 8.11 (s, 1H), 7.29-7.43 (m, 3H), 6.94-6.99 (m, 1H), 6.53 (s, 1H), 6.15-6.17 (m, 1H), 5.22-5.41 (m, 4H), 4.67-4.71 (m, 1H), 4.47-4.49 (m, 1H), 3.96-3.98 (m, 1H), 3.80-3.82 (m, 1H), 3.38 (s, 1H), 3.12 (q, J=6.68 Hz, 2H), 1.04 (t, J=7.16 Hz, 3H).

LCMS: (Method A) 440.0 (M+H), RT 2.94 min, 98.26% (Max), 98.21% (220 nm).

HPLC: (Method A) RT 3.10 min, 98.12% (Max), 98.13% (220 nm).

Compound no. 87

400 MHz, DMSO-d6: δ 8.07 (s, 1H), 7.09-7.17 (m, 3H), 6.83-6.87 (m, 1H), 6.15 (s, 1H), 5.12-5.34 (m, 4H), 4.67-4.70 (m, 1H), 4.42-4.48 (m, 1H), 3.98-4.01 (m, 1H), 3.80-3.83 (m, 1H), 3.70-3.72 (m, 1H), 3.32 (s, 1H), 2.11 (s, 3H), 1.04 (t, J=7.12 Hz, 3H).

LCMS: (Method A) 420.3 (M+H), RT 2.96 min, 98.43% (Max), 98.19% (220 nm).

HPLC: (Method A) RT 2.98 min, 97.54% (Max), 97.51% (220 nm).

Compound no. 88

400 MHz, DMSO-d6: δ 8.10 (s, 1H), 6.86-7.12 (m, 4H), 6.17 (s, 1H), 5.13-5.31 (m, 2H), 5.07 (s, 2H), 4.66-4.70 (m, 1H), 4.43-4.49 (m, 1H), 3.72-3.98 (m, 6H), 3.35-3.36 (m, 1H), 3.13 (q, J=7.16 Hz, 2H), 1.04 (t, J=7.16 Hz, 3H).

LCMS: (Method A) 436.0 (M+H), RT 2.52 min, 98.68% (Max), 98.77% (220 nm).

HPLC: (Method A) RT 2.49 min, 98.98% (Max), 98.82% (220 nm).

Compound no. 89

400 MHz, DMSO-d6: δ 8.13 (s, 1H), 7.11-7.36 (m, 4H), 6.12-6.14 (m, 1H), 5.19-5.21 (m, 2H), 4.66-4.70 (m, 1H), 4.42-4.48 (m, 1H), 3.69-4.12 (m, 3H), 3.10-3.12 (m, 2H), 1.03 (t, J=7.12 Hz, 3H).

LCMS: (Method A) 424.0 (M+H), RT 2.70 min, 96.44% (Max), 96.59% (220 nm).

HPLC: (Method A) RT 2.71 min, 98.53% (Max), 98.49% (220 nm).

Compound no. 90

400 MHz, DMSO-d6: δ 8.10 (s, 1H), 7.24 (d, J=8.52 Hz, 2H), 6.95 (q, J=8.72 Hz, 2H), 6.29 (s, 1H), 5.48-5.61 (m, 2H), 5.09 (s, 2H), 5.01-5.02 (m, 1H), 4.64-4.72 (m, 3H), 4.47-4.53 (m, 1H), 4.02-4.05 (m, 2H), 3.35 (s, 1H), 3.19-3.21 (m, 2H), 1.29 (d, J=6.22 Hz, 3H), 1.03 (t, J=7.20 Hz, 3H).

LCMS: (Method A) 450.0 (M+H), RT 2.14 min, 91.11% (Max), 93.37% (220 nm).

HPLC: (Method A) RT 2.14 min, 94.18% (Max), 94.06% (220 nm).

Compound no. 91

400 MHz, DMSO-d6: δ 8.13 (s, 1H), 8.07 (s, 1H), 7.08 (d, J=8.24 Hz, 2H), 6.90 (d, J=8.60 Hz, 2H), 6.18 (s, 1H), 5.26-5.33 (m, 2H), 4.43-4.69 (m, 2H), 3.97-3.99 (m, 1H), 3.70-3.82 (m, 2H), 3.11-3.17 (m, 2H), 2.22 (s, 3H), 1.05 (t, J=7.16 Hz, 3H).

LCMS: (Method A) 420.0 (M+H), RT 2.97 min, 98.63% (Max), 98.27% (220 nm).

HPLC: (Method A) RT 3.06 min, 98.62% (Max), 98.64% (220 nm).

Compound no. 92

400 MHz, DMSO-d6: δ 8.10 (s, 1H), 7.31-7.34 (m, 2H), 7.04-7.07 (m, 2H), 6.19 (s, 1H), 5.30-5.39 (m, 2H), 5.12 (s, 2H), 4.66-4.70 (m, 1H), 4.44-4.49 (m, 1H), 3.98-4.01 (m, 1H), 3.70-3.82 (m, 1H), 3.12-3.15 (m, 2H), 1.07 (t, J=7.18 Hz, 3H).

LCMS: (Method A) 440.0 (M+H), RT 3.11 min, 96.14% (Max), 97.82% (220 nm).

HPLC: (Method A) RT 3.13 min, 98.16% (Max), 98.14% (220 nm).

Compound no. 93

400 MHz, DMSO-d6: δ 8.09 (s, 1H), 7.02-7.14 (m, 4H), 6.20 (s, 1H), 5.21-5.50 (m, 2H), 5.12 (s, 2H), 4.66-4.70 (m, 1H), 4.44-4.49 (m, 1H), 3.99-4.00 (m, 1H), 3.70-3.32 (m, 3H), 3.14-3.16 (m, 2H), 1.05 (t, J=7.16 Hz, 3H).

LCMS: (Method A) 424.3 (M+H), RT 2.73 min, 99.27% (Max), 99.37% (220 nm).

HPLC: (Method A) RT 2.76 min, 99.26% (Max), 99.03% (220 nm).

Compound no. 94

400 MHz, DMSO-d6: δ 8.08 (s, 1H), 7.29 (dd, J=2.16, 6.74 Hz, 2H), 6.94 (dd, J=2.12, 6.72 Hz, 2H), 6.19 (s, 1H), 5.28 (s, 2H), 5.08 (s, 2H), 4.66-4.69 (m, 1H), 4.44-4.49 (m, 1H), 3.73-3.99 (m, 3H), 3.32-0.00 (m, 1H), 3.16-0.00 (m, 2H), 1.24 (s, 9H), 1.05 (t, J=7.24 Hz, 3H).

LCMS: (Method A) 462.3 (M+H), RT 3.87 min, 98.04% (Max), 98.10% (220 nm).

HPLC: (Method A) RT 3.86 min, 97.12% (Max), 97.35% (220 nm).

EXAMPLE 48

(3aR,5S,6S,7R,7aR)-2-(ethylamino)-6,7-dihydroxy-5,6,7,7a-tetrahydro-3aH-pyrano[3,2-d]thiazole-5-carboxylic acid The carboxylic acid intermediate of Schemes 1 to 3 was synthesized as follows: To a suspension of (3aR,5R,6S,7R,7aR)-2-(ethylamino)-5-(hydroxymethyl)-5,6,7,7a-tetrahydro-3aH-pyrano[3,2-d]thiazole-6,7-diol (23 g, 93 mmol) in 1:1 THF/aqueous NaHCO$_3$ (1200 mL) was added TEMPO (3.2 g, 20 mmol) and potassium bromide (3.5 g, 30 mmol). The mixture was then cooled to 0° C. and a solution of sodium hypochlorite (190 mL, 9% active chlorine basis) was added, dropwise. After 1 h, additional amounts of sodium hypochlorite solution (95 mL) and TEMPO (1.6 g, 10 mmol) were added. After TLC analysis indicated the reaction was complete, the reaction solution was extracted with diethyl ether (2×250 mL). The aqueous layer was acidified with 5N HCl to pH 5-6, and then concentrated under reduced pressure. The residue was purified by flash chromatography on silica gel using a gradient of methanol/dichloromethane (1% to 50%) to afford the title compound (23 g).

MS (m/z): 263 [M+H]$^+$.

EXAMPLE 49

Human O-GlcNAcase Enzyme Inhibition Assay

A TTP LabTech Mosquito liquid handler instrument pipetted 100 nL of the appropriate concentration of a solution of inhibitor in 100% DMSO (for a dose response curve calculation) into each well of a 384-well plate (Aurora Biotechnologies, Part #30311). The following reaction components were added to a final volume of 10 μL in McIlvaine's Buffer (pH 6.5):

20 nM His-Tagged hOGA and 10 μM Fluoroscein mono-beta-D-(2-deoxy-2-N-acetyl) glucopyranoside (FL-GlcNAc; Marker Gene Technologies Inc, Part #M1485). The plate was incubated for 60 min at room temperature and then the reaction was terminated by the addition of 10 μL of stop buffer (200 mM glycine, pH 10.75). The plate was read on an Envision platform in a fluorescent format using the top mirror with 485 nm+dampener as the excitation filter setting and 520 nm as the emission filter setting. The amount of fluorescence measured was plotted against the concentration of inhibitor to produce a sigmoidal dose response curve, from which an $IC_{50}$ was calculated.

EXAMPLE 50

Assay for the Determination of Cellular Activity for Compounds that Inhibit O-GlcNAcase Activity Inhibition of O-GlcNAcase, which removes O-GlcNAc from cellular proteins, results in an increase in the level of O-GlcNAcylated proteins in cells. An increase in the O-GlcNAcylation of cellular proteins can be measured by an antibody, such as CTD110.6, that binds O-GlcNAcylated proteins. The amount of O-GlcNAcylated protein can be determined by the enzyme linked immunoabsorbant assay (ELISA) technique.

Cell lines, such as rat B35, rat PC-12 and human SH-SY5Y cells, expressing endogenous levels of O-GlcNAcase, could be utilized. Cells were plated in 96-well plates at a density of approximately 10,000 cells/well. Compounds to be tested were dissolved in DMSO as 10 mM stock solution, and then diluted first with DMSO and then culture media using the Bravo workstation. Cells were treated with diluted compounds for approximately 16 hours. Typically, eight 4-fold dilutions steps, starting at 25 μM were used to reach a final concentration of inhibitor desired to measure a compound concentration dependent response in cells. To prepare a cell lysate, the media from compound treated cells were removed, and the cells were washed once with Dulbecco's phosphate buffered saline (DPBS) and then lysed for 30 minutes in 100 μl/well of ice cold RIPA buffer containing a protease inhibitor cocktail.

The ELISA portion of the assay was performed in EIA/RIA plates that were coated overnight at 4 C with 80 μl/well of cell lysate. The following day the wells were washed 6 times with 200 μl of wash buffer (0.05% Tween20 in DPBS). The wells were blocked with 200 μl blocking buffer (1% BSA, 0.05% Tween20 in DPBS) for 1 h at room temperature. Each well was then washed 6 times with 200 μl of wash buffer. The anti-O-GlcNAc antibody CTD110.6 (Covance, Princeton, N.J.) was added at 100 μl/well at a concentration of 10 μg/ml. The plates were incubated for 1 h at room temperature. The wells were then washed 6 times with 200 μl/well of wash buffer. To detect the amount of CTD110.6 bound to the cell lysate, alkaline phosphatase conjugated goat anti-mouse IgM (diluted 1:500 in blocking buffer) was added at 100 μl/well and incubated for 45 min at room temperature. Each well was then washed 6 times with 200 μl/well of wash buffer. PNPP tablets dissolved in diethanolamine substrate buffer and 100 μl/well were added as detection reagent. The detection reaction was incubated for 25 min at room temperature and absorbance was read at 405 nm.

The amount of O-GlcNAcylated protein, as detected by the ELISA assay, was plotted for each concentration of test compound using standard curve fitting algorithms for sigmoidal dose response curves. The values for a four parameter logistic curve fit of the data were determined, with the inflection point of the curve being the potency value for the test compound.

EXAMPLE 51

Pharmaceutical Preparations (A) Injection vials: A solution of 100 g of an active ingredient according to the invention and 5 g of disodium hydrogen phosphate in 3 l of bi-distilled water was adjusted to pH 6.5 using 2 N hydrochloric acid, sterile filtered, transferred into injection vials, lyophilized under sterile conditions and sealed under sterile conditions. Each injection vial contained 5 mg of active ingredient.

(B) Suppositories: A mixture of 20 g of an active ingredient according to the invention was melted with 100 g of soy lecithin and 1400 g of cocoa butter, poured into moulds and allowed to cool. Each suppository contained 20 mg of active ingredient.

(C) Solution: A solution was prepared from 1 g of an active ingredient according to the invention, 9.38 g of $NaH_2PO_4.2H_2O$, 28.48 g of $Na_2HPO_4.12H_2O$ and 0.1 g of benzalkonium chloride in 940 ml of bi-distilled water. The pH was adjusted to 6.8, and the solution was made up to 1 l and sterilized by irradiation. This solution could be used in the form of eye drops.

(D) Ointment: 500 mg of an active ingredient according to the invention were mixed with 99.5 g of Vaseline under aseptic conditions.

(E) Tablets: A mixture of 1 kg of an active ingredient according to the invention, 4 kg of lactose, 1.2 kg of potato starch, 0.2 kg of talc and 0.1 kg of magnesium stearate was pressed to give tablets in a conventional manner in such a way that each tablet contained 10 mg of active ingredient.

(F) Coated tablets: Tablets were pressed analogously to EXAMPLE E and subsequently coated in a conventional manner with a coating of sucrose, potato starch, talc, tragacanth and dye.

(G) Capsules: 2 kg of an active ingredient according to the invention were introduced into hard gelatin capsules in a conventional manner in such a way that each capsule contained 20 mg of the active ingredient.

(H) Ampoules: A solution of 1 kg of an active ingredient according to the invention in 60 l of bi-distilled water was sterile filtered, transferred into ampoules, lyophilized under sterile conditions and sealed under sterile conditions. Each ampoule contained 10 mg of active ingredient.

(I) Inhalation spray: 14 g of an active ingredient according to the invention were dissolved in 10 l of isotonic NaCl solution, and the solution was transferred into commercially available spray containers with a pump mechanism. The solution could be sprayed into the mouth or nose. One spray shot (about 0.1 ml) corresponded to a dose of about 0.14 mg.

The invention claimed is:
1. A compound of formula (I)

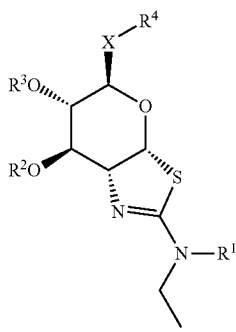

(I)

wherein
R¹ denotes Y, COA, COOA, COO—(CH$_2$)$_n$—Ar— or COO—(CH$_2$)$_n$-Cyc;
R², R³ denote independently from one another Y or SO$_2$Y;
R⁴ denotes Cl, Br, I, COOY, SO$_2$Y, CN, CAr$_3$, (CH$_2$)$_m$—Ar,

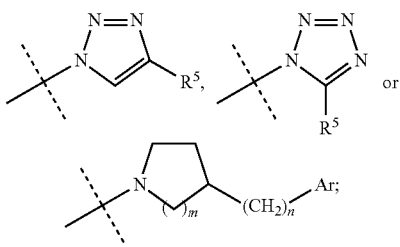

R⁵ denotes (CH$_2$)$_n$—Ar, (CH$_2$)$_n$-Cyc, (CH$_2$)$_n$-Het, (CH$_2$)$_n$—O—Ar, (CH$_2$)$_n$—CY(OH)—Ar, (CH$_2$)$_n$—CO—Ar or (CH$_2$)$_n$—NY—Ar;
X denotes CH$_2$, CO or CH(OH);
Y denotes H or A;
A denotes unbranched or branched alkyl having 1-10 C atoms,
  in which 1-7H atoms can be replaced independently from one another by Hal or in which one CH$_2$ group can be replaced by a —CH=CH— group;
Cyc denotes cycloalkyl having 3-7 C atoms,
  in which 1-4H atoms can be replaced independently from one another by Hal or which can be substituted by Ar;
Ar denotes an unsaturated or aromatic mono- or bicyclic carbocycle having 3-12 C atoms,
  which can be substituted by at least one substituent selected from the group of Hal, A, (CY$_2$)$_n$—OY, (CY$_2$)$_n$—NYY, COOY, CONYY, NHCOY, SO$_2$Y, CN and phenoxy;
Het denotes an unsaturated or aromatic mono-, bi- or tricyclic heterocycle having 1-12 C atoms and 1-4 N atoms,
  which can be substituted by at least one substituent selected from the group of Hal, A, (CY$_2$)$_n$—OY, (CY$_2$)$_n$—NYY, COOY, CONYY, NHCOY, SO$_2$Y, SO$_2$Ar, CN and thiophenyl;
Hal denotes F, Cl, Br or I;
m denotes 1, 2 or 3; and
n denotes 0, 1, 2, 3, 4, 5 or 6;
or a physiologically acceptable salt thereof.

2. The compound according to claim 1, wherein
R¹, R², R³ denote independently from one another H or A.
3. The compound according to claim 1, wherein
R⁵ denotes (CH$_2$)$_n$—Ar, (CH$_2$)$_n$-Cyc, (CH$_2$)$_n$-Het, (CH$_2$)$_n$—O—Ar or CY(OH)—Ar.
4. The compound according to claim 1, having sub-formula (IA), (IB) or (IC)

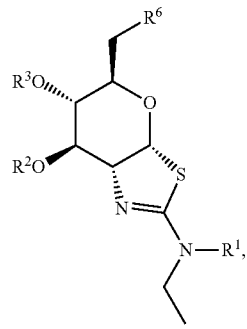

(IA)

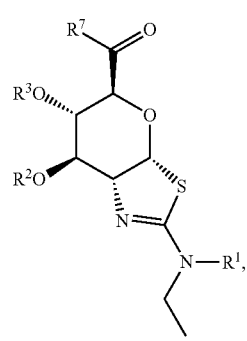

(IB)

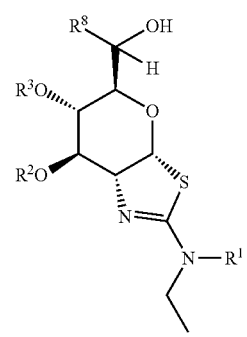

(IC)

wherein
R⁶ denotes Cl, Br, I, COOY, CAr$_3$ or

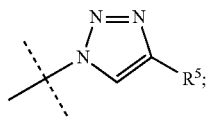

R⁷ denotes (CH$_2$)$_m$—Ar or

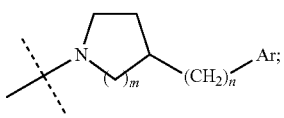

R⁸ denotes (CH$_2$)$_m$—Ar; and
R¹, R², R³, R⁵, Y, Ar, Het, m and n have the meaning as defined in claim 1;
or a physiologically acceptable salt thereof.

5. The compound according to claim 4, having sub-formula (IA-1) or (IA-2)

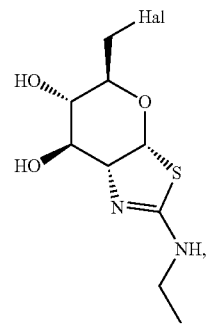
(IA-1)

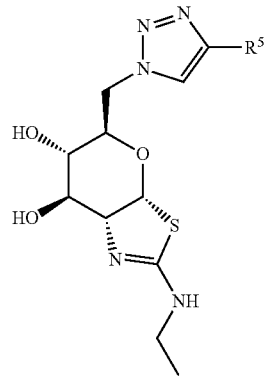
(IA-2)

wherein

Hal denotes Cl, Br or I; and

R⁵ and Y have the meaning as defined in claim 4;

or a physiologically acceptable salt thereof.

6. The compound according to claim 1, wherein

A denotes unbranched or branched alkyl having 1-6 C atoms,
   in which 1-4H atoms can be replaced independently from one another by Hal;

Ar denotes an aromatic mono- or bicyclic carbocycle having 3-12 C atoms,
   which can be substituted by at least one substituent selected from the group of Hal, A, $(CY_2)_n$—OY, $(CY_2)_n$—NYY, $SO_2Y$, CN and phenoxy;

Het denotes an unsaturated or aromatic mono-, bi- or tricyclic heterocycle having 2-12 C atoms and 1-3 N atoms,
   which can be mono-, di- or trisubstituted by at least one substituent selected from the group of Hal, A, $(CH_2)_n$—OY, $(CY_2)_n$—NYY, $SO_2Y$, $SO_2Ar$, CN and thiophenyl;

or n denotes 0, 1, 2, 3 or 4.

7. The compound according to claim 1, which is selected from the group consisting of:

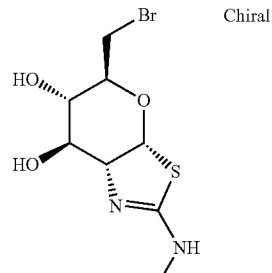
5

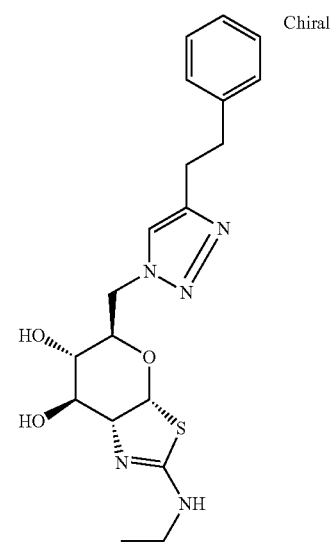
6

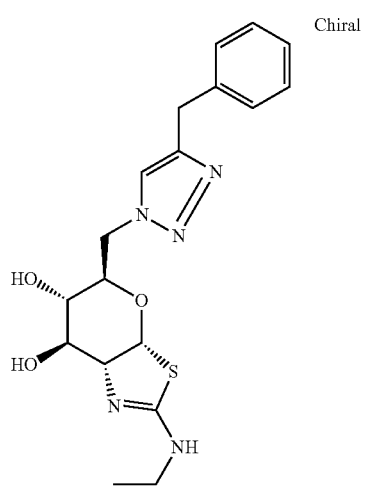
14

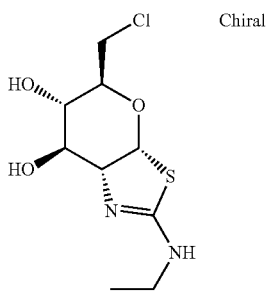
32

133
50
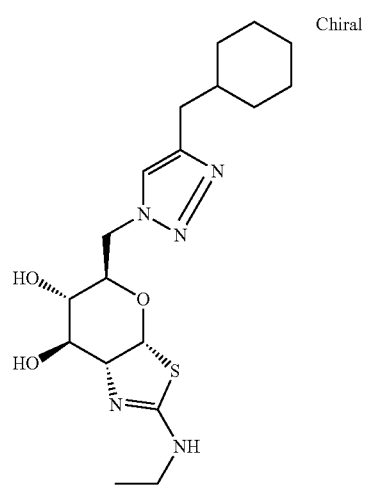
57
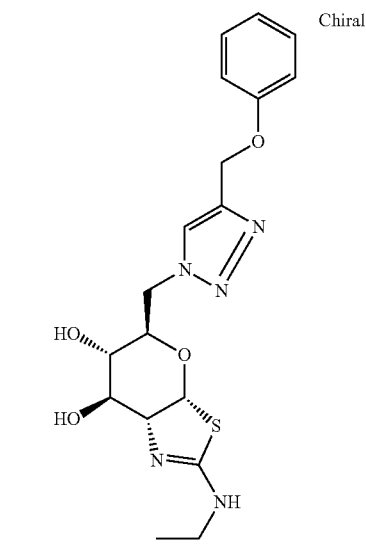
58
134
65
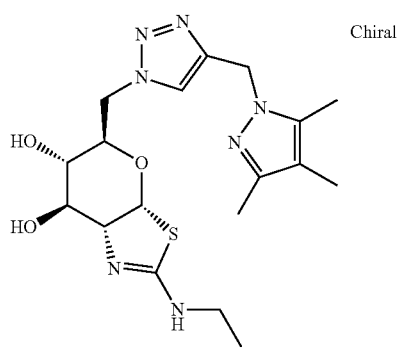 [SMILES: CCNC1=N[C@@H]2[C@@H](O)[C@H](O)[C@@H](Cn3cc(Cn4nc(C)nc4C)nn3)O[C@@H]2S1]
66
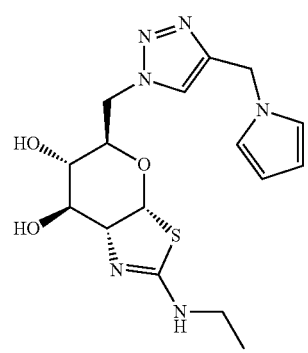
67
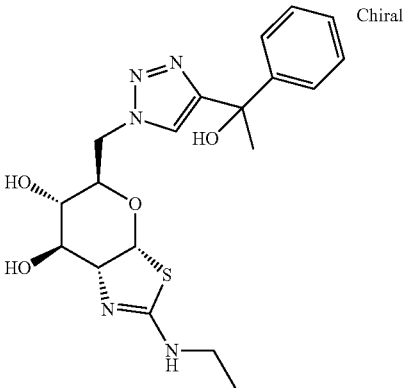
68
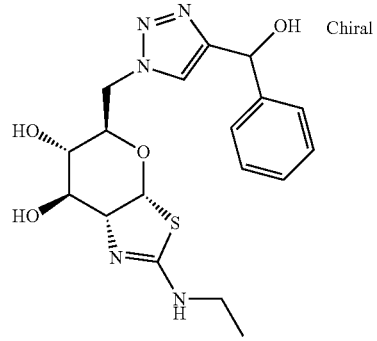

70 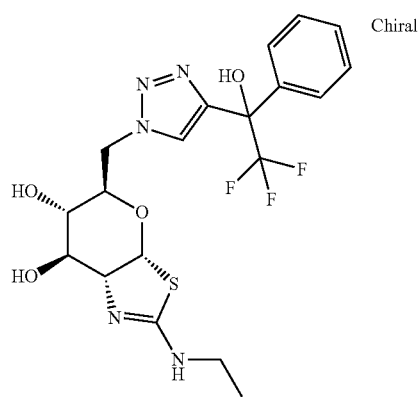
75 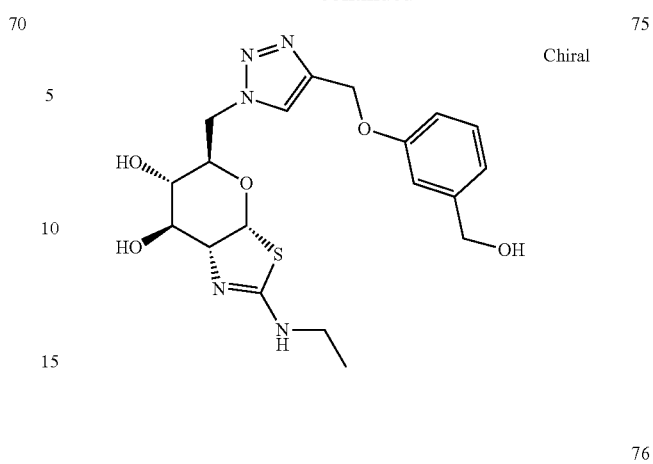
72 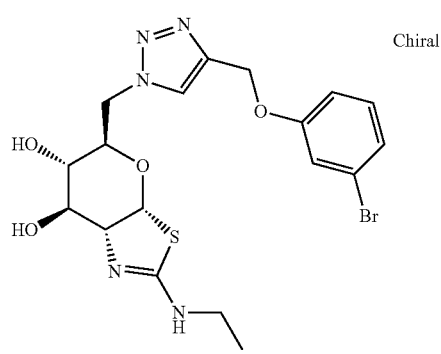
76 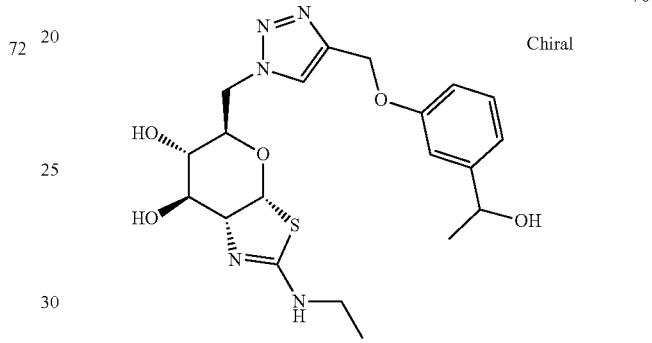
73 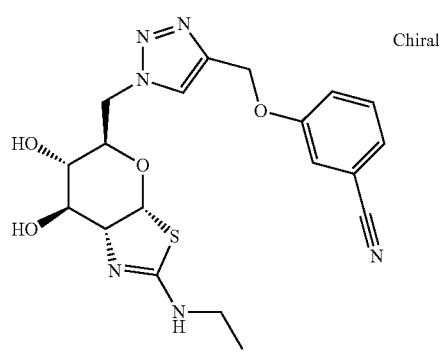
77 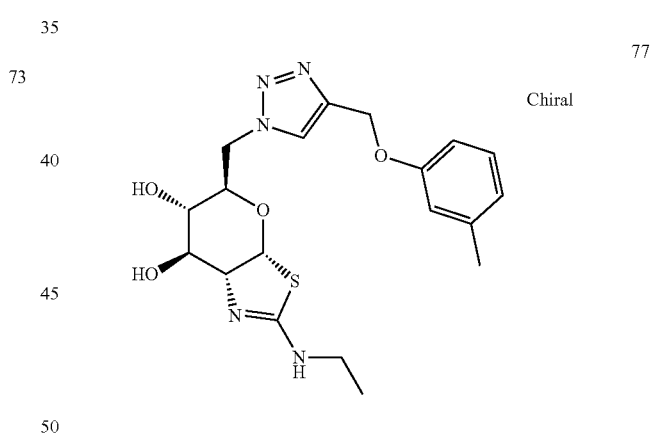
74 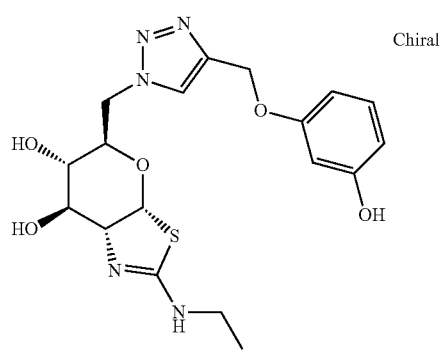
78 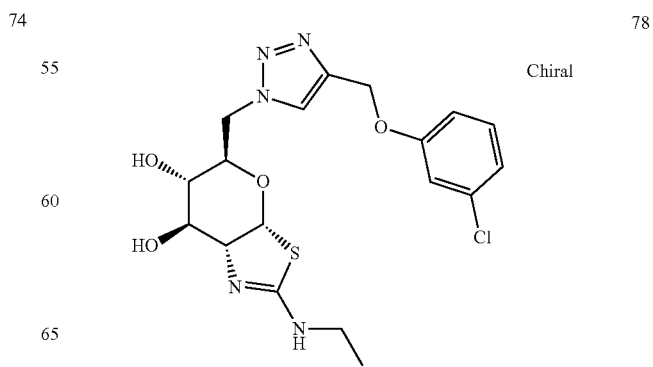

79
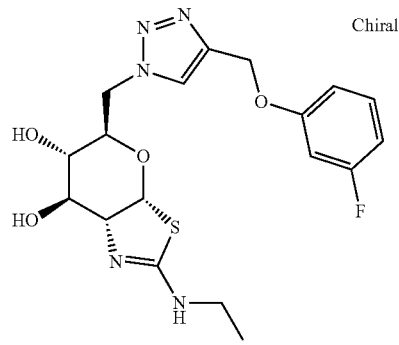
80
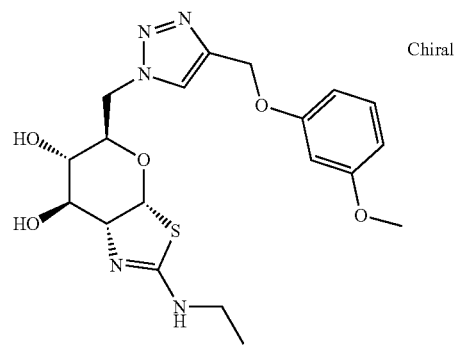
81
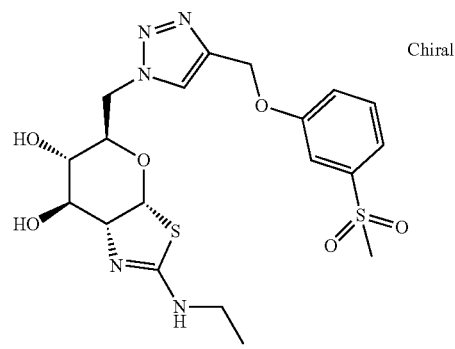
82
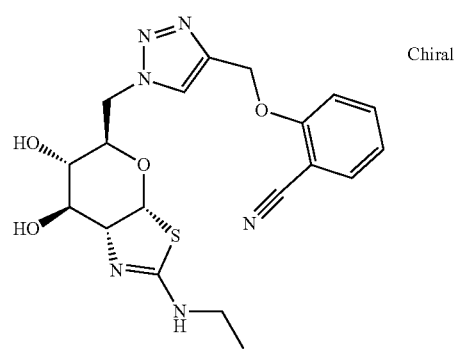
86
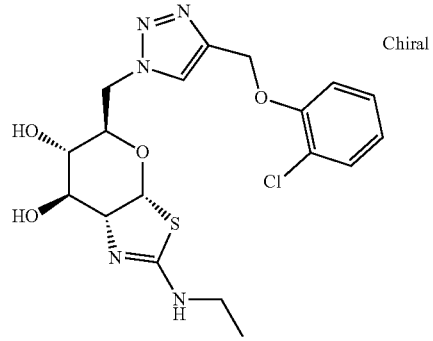
87
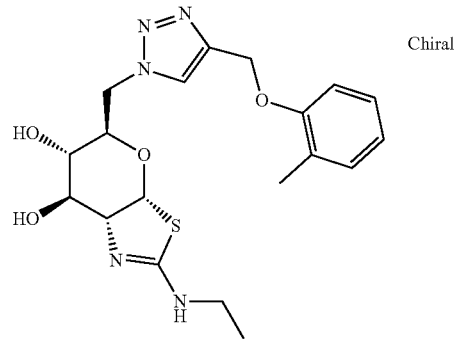
88
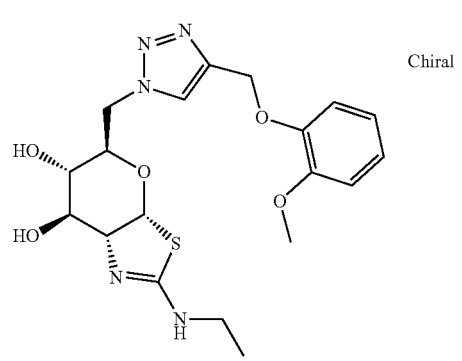
89
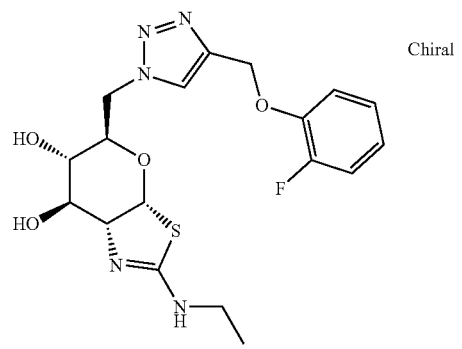

-continued

90 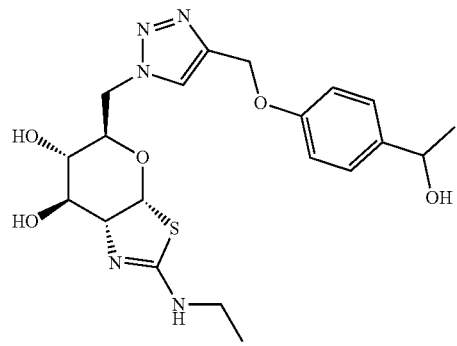

92 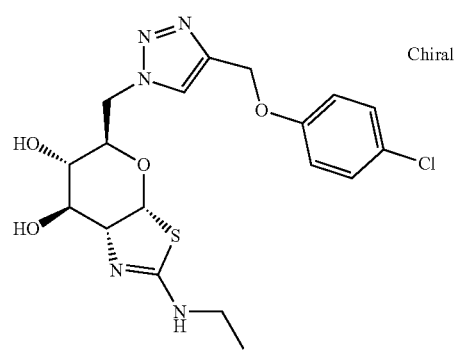

93 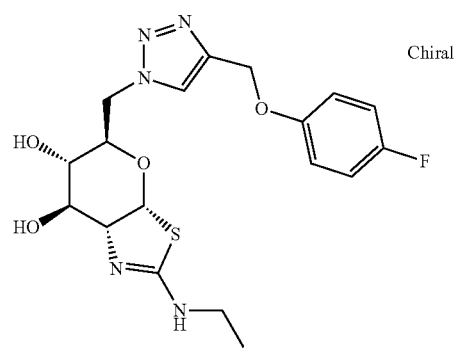

95 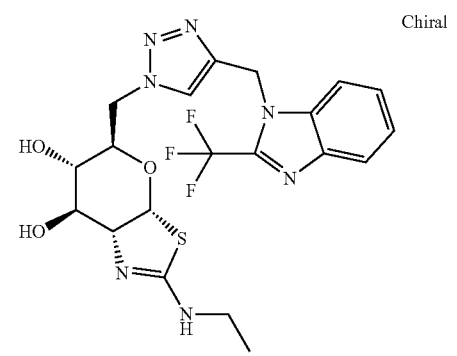

-continued

96 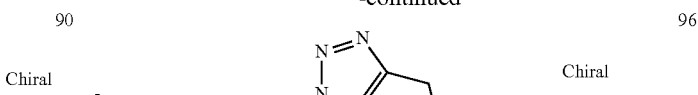

97 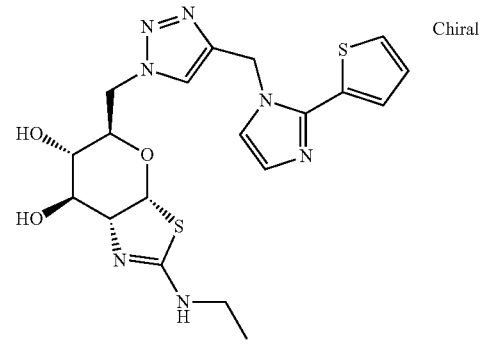

98 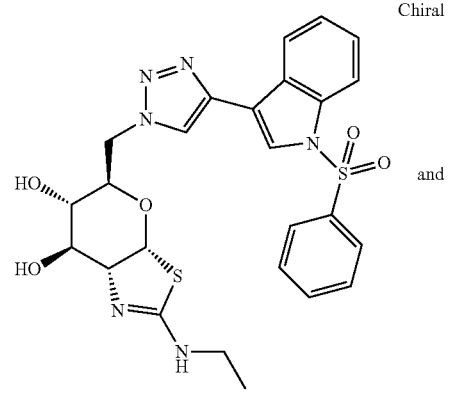

and

99 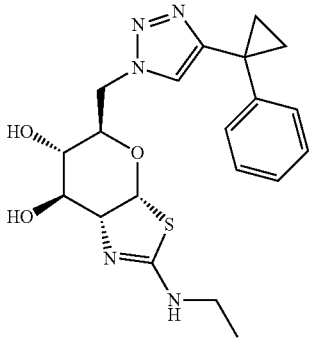

or a physiologically acceptable salt thereof.

8. A medicament comprising at least one compound according to claim 1 or a physiologically acceptable salt thereof.

9. A pharmaceutical composition comprising as active ingredient an effective amount of at least one compound according to claim 1 or a physiologically acceptable salt thereof together with pharmaceutically tolerable adjuvants.

10. A method for treating Alzheimer's disease, said method comprising administering an effective amount of at least one compound according to claim 1 or a physiologically acceptable salt thereof to a mammal in need of such treatment.

11. A method for inhibiting a glycosidase, wherein a cell expressing said glycosidase is contacted with at least one compound according to claim 1 or a physiologically acceptable salt thereof under conditions such that said glycosidase is inhibited.

12. The method according to claim 11, wherein the glycosidase is contacted with at least one compound selectively inhibiting O-GlcNAcase.

13. The compound according to claim 2, wherein $R^1, R^2, R^3$ denote H.

14. The pharmaceutical composition according to claim 9, additionally comprising at least a second active pharmaceutical ingredient.

15. The method according to claim 12, wherein the compound has an $IC_{50}$ of less than 0.1 μM.

\* \* \* \* \*